US009433653B2

(12) United States Patent
Yoon et al.

(10) Patent No.: US 9,433,653 B2
(45) Date of Patent: Sep. 6, 2016

(54) METHOD FOR PREVENTION AND TREATMENT OF *ESCHERICHIA COLI* INFECTIONS USING A BACTERIOPHAGE WITH BROAD ANTIBACTERIAL SPECTRUM AGAINST *ESCHERICHIA COLI*

(71) Applicant: iNtRON Biotechnology, Inc., Kyeonggi-do (KR)

(72) Inventors: Seong Jun Yoon, Seoul (KR); Soo Youn Jun, Seoul (KR); Hyoung Rok Paik, Jeollanam-do (KR); Jee Soo Son, Seoul (KR); Hye In Jeong, Seoul (KR); Sang Hyeon Kang, Seoul (KR)

(73) Assignee: INTRON BIOTECHNOLOGY, INC., Kyeonggi-Do (KR)

( * ) Notice: Subject to any disclaimer, the term of this patent is extended or adjusted under 35 U.S.C. 154(b) by 0 days.

(21) Appl. No.: 14/706,325

(22) Filed: May 7, 2015

(65) Prior Publication Data

US 2015/0322409 A1 Nov. 12, 2015

(30) Foreign Application Priority Data

May 7, 2014 (KR) ........................ 10-2014-0053909

(51) Int. Cl.
*C12N 7/00* (2006.01)
*A61K 35/76* (2015.01)

(52) U.S. Cl.
CPC ................. *A61K 35/76* (2013.01); *C12N 7/00* (2013.01); *C12N 2795/00021* (2013.01); *C12N 2795/00031* (2013.01); *C12N 2795/00032* (2013.01)

(58) Field of Classification Search
None
See application file for complete search history.

(56) References Cited

PUBLICATIONS

New Riverside University Dictionary. The Riverside Publishing Company, p. 933, 1984.*
Illustrated Stedman's Medical Dictionary, 24th Edition, p. 707, 1982.*

* cited by examiner

*Primary Examiner* — S. Devi
(74) *Attorney, Agent, or Firm* — Pearl Cohen Zedek Latzer Baratz LLP

(57) ABSTRACT

The present invention relates to a composition comprising the bacteriophage EK88P-1 isolated from the nature and having a broad antibacterial spectrum against *E. coli* as an active ingredient, and a method for preventing and treating *E. coli* infections using the said composition. The bacteriophage EK88P-1, the active ingredient of the composition of the present invention, has a broad antibacterial spectrum against *E. coli* and has the genome characteristically composed of the partial nucleotide sequences represented by SEQ ID NO: 1 to SEQ ID NO: 25, and also characterized by the bacteriophage belonging to the Myoviridae family according to the morphology that is composed of the major structural proteins in the sizes of approximately 49 kDa, 53 kDa, 94 kDa, and 103 kDa.

4 Claims, 3 Drawing Sheets

METHOD FOR PREVENTION AND TREATMENT OF *ESCHERICHIA COLI* INFECTIONS USING A BACTERIOPHAGE WITH BROAD ANTIBACTERIAL SPECTRUM AGAINST *ESCHERICHIA COLI*

BACKGROUND OF THE INVENTION

1. Field of the Invention

The present invention relates to a composition usable for the prevention and treatment of *E. coli* infections which comprises a bacteriophage isolated from the nature and having a broad antibacterial spectrum against *E. coli*, and a method for preventing and treating *E. coli* infections using the same. More precisely, the present invention relates to a bacteriophage comprising the partial nucleotide sequences represented by SEQ ID NO: 1 to SEQ ID NO: 25, a composition for the prevention and treatment of *E. coli* infections comprising the said bacteriophage as an active ingredient, and a method for preventing and treating *E. coli* infections using the said composition.

2. Description of the Related Art

*E. coli* is Gram-negative intestinal bacteria belonging to *bacillus*. Most of *E. coli* are residential flora which means they are not pathogenic bacteria, yet. But, *E. coli O*157:H7 or ETEC (enterotoxigenic *E. coli*) are pathogenic bacteria that cause food poisoning in human or diarrhea in animals such as cow, pig, and goat, etc. Pathogenic *E. coli* can produce heat-labile enterotoxin (LT) that loses its activity when it is heated at 60° C. for 10 minutes, or heat-stable enterotoxin (ST) that exhibits resistance against heat and is stable at 100° C. upto 30 minutes.

Among the pathogenic *E. coli*, ETEC strains have been an issue that cause serious problems in livestock industry, particularly they cause diarrhea in newborn piglets or weaning pigs. Particularly, *E. coli* K88 strains, *E. coli* K99 strains, *E. coli* 987P strains, and *E. coli* F41 strains are known as the major enterotoxigenic *E. coli* types.

Considering a significant damage in livestock industry by such *E. coli*, it is urgently requested to develop a method for preventing or treating *E. coli* infections. A variety of antibiotics have been used to prevent or treat such pathogenic *E. coli* infections. However, according to the recent rise of antibiotic-resistant bacteria, an efficient alternative is urgently requested.

Recently, the use of bacteriophages has drawn our attention as a new way of treating bacterial infections. Particularly, the reason of our high interest in bacteriophages is because bacteriophage-based treatment is a nature-friendly method. Bacteriophages are an extremely small microorganism that infects bacteria, which are called phage in short. Once bacteriophage infects bacteria, the bacteriophage is proliferated in the inside of the bacterial cell. After full proliferation, the progenies destroy the bacterial cell wall to escape from the host, suggesting that the bacteriophage has bacteria killing ability. The bacteriophage infection is characterized by high specificity, so that a certain bacteriophage infects only a specific bacterium. That is, the bacterium that can be infected by certain bacteriophage is limited, suggesting that bacteriophage can kill only a specific bacterium and cannot harm other bacteria.

Bacteriophage was first found out by an English bacteriologist Twort in 1915 when he noticed that *Micrococcus* colonies melted and became transparent by something unknown. In 1917, a French bacteriologist d'Herelle found out that *Shigella disentriae* in the filtrate of dysentery patient feces melted by something, and further studied about this phenomenon. As a result, he identified bacteriophage independently, and named it as bacteriophage which means a bacteria killer. Since then, bacteriophages specifically acting against such pathogenic bacteria as *Shigella, Salmonella typhi*, and *Vibrio cholerae* have been continuously identified.

Owing to the unique capability of bacteriophage to kill bacteria, bacteriophages have been studied and anticipated as a method to treat bacterial infections. However, after penicillin was found by Fleming, studies on bacteriophages had been only continued in some of Eastern European countries and the former Soviet Union because of the universalization of antibiotics. After the year of 2000, the merit of the conventional antibiotics faded because of the increase of antibiotic-resistant bacteria. So, bacteriophages are once again spotlighted as a new anti-bacterial agent that can replace the conventional antibiotics.

According to the recent regulation of use of antibiotics by the government, the interest on bacteriophages increases more and more.

Thus, the present inventors tried to develop a composition usable for the prevention or treatment of *E. coli* infections by using a bacteriophage isolated from the nature and displayed a broad antibacterial spectrum against *E. coli* strains including *E. coli* K88 strains, and further tried to develop a method for preventing or treating *E. coli* infections using the said composition. As a result, the inventors succeeded in isolating an effective bacteriophage from the nature that displayed a broad antibacterial spectrum against *E. coli* strains and identified the partial nucleotide sequences of the genome of the isolated bacteriophage that could distinguish the isolated bacteriophage from previously reported bacteriophages. Based on that, the present inventors developed a composition comprising the isolated bacteriophage as an active ingredient and further confirmed that this composition could be efficiently used for the prevention and treatment of *E. coli* infections, leading to the completion of this present invention.

SUMMARY OF THE INVENTION

It is an object of the present invention to provide a novel bacteriophage that has a broad antibacterial spectrum against various *E. coli* strains including *E. coli* K88 strains.

It is another object of the present invention to provide a composition for preventing *E. coli* infections comprising the isolated bacteriophage having a broad antibacterial spectrum against various *E. coli* strains including *E. coli* K88 strains as an active ingredient, and a method for preventing *E. coli* infections using the said composition.

It is another object of the present invention to provide a composition for treating *E. coli* infections comprising the isolated bacteriophage having a broad antibacterial spectrum against various *E. coli* strains including *E. coli* K88 strains as an active ingredient, and a method for treating *E. coli* infections using the said composition.

It is further an object of the present invention to provide a disinfectant for the prevention and treatment of *E. coli* infections using the said composition.

It is also an object of the present invention to provide a drinking water additive for the prevention and treatment of *E. coli* infections using the said composition.

It is also an object of the present invention to provide a feed additive for the prevention and treatment of *E. coli* infections using the said composition.

To achieve the above objects, the present invention provides a composition comprising the bacteriophage isolated from the nature and displayed a broad antibacterial spectrum against various *E. coli* strains including *E. coli* K88 strains as an active ingredient, and a method for preventing and treating *E. coli* infections using the said composition.

The isolated bacteriophage included in the composition of the present invention as an active ingredient is the bacteriophage EK88P-1 that characteristically displays a broad antibacterial spectrum against various *E. coli* strains including *E. coli* K88 strains and contains the partial nucleotide sequences represented by SEQ ID NO: 1 to SEQ ID NO: 25. The bacteriophage EK88P-1 isolated by the present inventors was deposited at Korean Collection for Type Cultures, Korea Research Institute of Bioscience and Biotechnology in Apr. 10, 2014 (Accession No: KCTC 12574BP).

The present invention also provides a disinfectant, a drinking water additive, and a feed additive for the prevention or treatment of *E. coli* infections.

Since the bacteriophage EK88P-1 included in the composition of the present invention displays a broad antibacterial spectrum against various *E. coli* strains including *E. coli* K88 strains, it is regarded as to be effective in preventing or treating various diseases caused by various *E. coli* strains including *E. coli* K88 strains. Therefore, the composition of the present invention can be utilized for the prevention and treatment of diseases caused by various *E. coli* strains including *E. coli* K88 strains. The diseases caused by various *E. coli* strains including *E. coli* K88 strains herein indicate all the symptoms accompanied by *E. coli* infections including *E. coli* K88 infections, such as death, diarrhea, and growth retardation, etc.

In this description, the term "treatment" or "treat" indicates (i) to suppress the diseases caused by various *E. coli* strains including *E. coli* K88 strains; and (ii) to relieve the diseases caused by various *E. coli* strains including *E. coli* K88 strains.

In this description, the term "isolation" or "isolated" indicates all the actions to separate the bacteriophage by using diverse experimental techniques and to secure the characteristics that can distinguish this bacteriophage from others, and further includes the action of proliferating the bacteriophage via bioengineering techniques so as to make it useful.

The bacteriophage of the present invention includes the bacteriophage EK88P-1 and its variants. The "variants" herein indicate the bacteriophages that have minor variations in genomic sequence or polypeptide coding genetic information but have the equivalent genotypic and phenotypic characteristics as the bacteriophage EK88P-1 of the present invention. The said variants include polymorphic variants as well. It is preferred for those variants to have the same or equivalent biological functions as the bacteriophage EK88P-1 of the present invention.

The pharmaceutically acceptable carrier included in the composition of the present invention is the one that is generally used for the preparation of a pharmaceutical formulation, which is exemplified by glucose, maltodextrin, lactose, dextrose, sucrose, sorbitol, mannitol, starch, acacia rubber, calcium phosphate, alginate, gelatin, calcium silcate, microcrystalline cellulose, polyvinyl pyrrolidone, cellulose, water, syrup, methylcellulose, methylhydroxybenzoate, propylhydroxybenzoate, talc, magnesium stearate, and mineral oil, but not always limited thereto. The composition of the present invention can additionally include lubricants, wetting agents, sweeteners, flavors, emulsifiers, suspending agents, and preservatives, in addition to the above ingredients.

In the composition of the present invention, the bacteriophage EK88P-1 or the variants thereof are included as an active ingredient. At this time, the bacteriophage EK88P-1 or the variants thereof are preferably included at the concentration of $1\times10^{1}$ pfu/ml~$1\times10^{30}$ pfu/ml or $1\times10^{1}$ pfu/g~$1\times10^{30}$ pfu/g, and more preferably at the concentration of $1\times10^{4}$ pfu/ml~$1\times10^{15}$ pfu/ml or $1\times10^{4}$ pfu/g~$1\times10^{15}$ pfu/g.

The composition of the present invention can be formulated by the method that can be performed by those in the art by using a pharmaceutically acceptable carrier and/or excipient in the form of unit dose or in a multi-dose container. The formulation can be in the form of solution, suspension or emulsion in oil or water-soluble medium, extract, powder, granule, tablet or capsule. At this time, a dispersing agent or a stabilizer can be additionally included.

The composition of the present invention can be prepared as a disinfectant, a drinking water additive, or a feed additive according to the purpose of use, but not always limited thereto.

Advantageous Effect

The composition of the present invention and the method for preventing and treating various *E. coli* infections including *E. coli* K88 infections using the said composition have the advantage of high specificity to various *E. coli* strains including *E. coli* K88 strains, compared with the conventional methods based on the chemical materials including the conventional antibiotics. That means, the composition of the present invention can be used for preventing or treating various *E. coli* infections including *E. coli* K88 infections specifically without affecting other useful residential bacteria, and accordingly has fewer side effects. In general, when chemical materials such as antibiotics are used, the general residential bacteria are also damaged to weaken immunity in animals with carrying various side effects. In the meantime, the composition of the present invention uses the bacteriophage isolated from the nature as an active ingredient, so that it is very nature-friendly.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation of Bacteriophage Capable of Killing *E. coli* Cells

Samples were collected from the nature to screen the bacteriophage having the capability to kill *E. coli* cells. The *E. coli* strains used for the bacteriophage isolation herein were the one that had been isolated by the present inventors and identified as an *E. coli* K88 strain previously.

The isolation procedure of the bacteriophage is described in more detail hereinafter. The collected sample was added to the TSB (Tryptic Soy Broth) medium (pancreatic digest of casein, 17 g/L; papaic digest of soybean, 3 g/L; dextrose, 2.5 g/L; sodium chloride, 5 g/L; dipotassium phosphate, 2.5 g/L) inoculated with *E. coli* culture at the ratio of 1/1000, followed by shaking culture at 37° C. for 3~4 hours. Upon completion of the culture, centrifugation was performed at 8,000 rpm for 20 minutes and supernatant was recovered. The recovered supernatant was inoculated with *E. coli* culture at the ratio of 1/1000, followed by shaking culture at 37° C. for 3~4 hours. When the sample contained the effective bacteriophage, the above procedure was repeated total 5 times in order to increase the titer of the bacteriophage. After repeating the procedure 5 times, the culture solution proceeded to centrifugation at 8,000 rpm for 20 minutes and supernatant was recovered. The recovered supernatant was filtered by using a 0.45 μm filter. The obtained filtrate was used in spot assay for examining whether or not the bacteriophage that can kill *E. coli* cells was included therein.

Spot assay was performed as follows; TSB medium was inoculated with *E. coli* culture at the ratio of 1/1000, followed by shaking culture at 37° C. for overnight. 2 ml ($OD_{600}$=2.0) of the *E. coli* culture broth prepared above was spreaded on the TSA (Tryptic Soy Agar; pancreatic digest of casein, 17 g/L; papaic digest of soybean, 3 g/L; sodium chloride, 5 g/L; agar, 15 g/L) plate. The plate stood in a clean bench for 30 minutes to dry. After drying, 10 μl of the prepared filtrate was spotted directly onto the surface of the bacterial lawns and dried for about 30 minutes. Following drying, the plate was incubated at 37° C. for a day. Next day, the plate was examined for the formation of clear zones on the surface of the bacterial lawns. If a clear zone was generated where the filtrate was dropped, it could be judged that the bacteriophage that could kill *E. coli* cells was included in the filtrate. Through the above procedure, the filtrate containing the bacteriophage having the capability to kill *E. coli* cells could be obtained.

Figure 1:
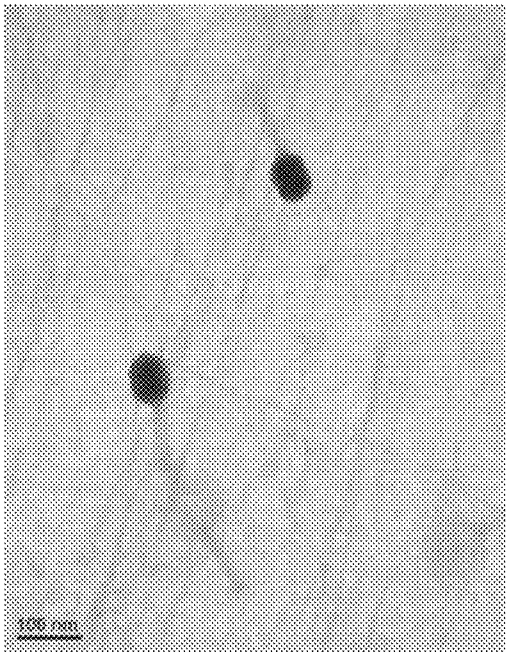
FIG. 1 is an electron micrograph showing the morphology of the bacteriophage EK88P-1.

Then, the bacteriophage was isolated from the filtrate confirmed above to have the bacteriophage capable of killing *E. coli* cells. The conventional plaque assay was used for the bacteriophage isolation. Particularly, a plaque formed in the course of the plaque assay was picked up by using a sterilized tip, which was then added to the *E. coli* culture solution, followed by shaking culture at 37° C. for 4~5 hours. Upon completion of the culture, centrifugation was performed at 8,000 rpm for 20 minutes to obtain supernatant. The recovered supernatant was inoculated with *E. coli* culture at the ratio of 1/50, followed by shaking culture at 37° C. for 3~4 hours. To increase the titer of the bacteriophage, the above procedure was repeated at least 5 times. Then, centrifugation was performed at 8,000 rpm for 20 minutes to obtain supernatant. Plaque assay was performed with the obtained supernatant. In general, the pure bacteriophage isolation is not completed by one-time procedure, so the above procedure was repeated. At least 5 times of repeated procedure, the solution containing the pure bacteriophage was obtained. The procedure for the isolation of the pure bacteriophage is generally repeated until the generated plaques become similar in sizes and morphologies. And the final pure bacteriophage isolation was confirmed by the observation under electron microscope. Until the pure bacteriophage isolation was confirmed under electron microscope, the above procedure was repeated. The observation under electron microscope was performed by the conventional method. Briefly, the solution containing the pure bacteriophage was loaded on copper grid, followed by negative staining with 2% uranyl acetate. After drying thereof, the morphology was observed under transmission electron microscope. The electron micrograph of the bacteriophage isolated in the present invention is presented in FIG. 1. From the morphological observation, the bacteriophage isolated in the present invention was identified as belonging to the family Myoviridae.

The solution containing the pure bacteriophage confirmed above proceeded to purification. *E. coli* culture broth was added to the solution containing the pure bacteriophage at the volume of 1/50 of the total volume of the bacteriophage solution, followed by shaking culture at 37° C. for 3~4 hours. Upon completion of the culture, centrifugation was performed at 8,000 rpm for 20 minutes to obtain supernatant. The said procedure was repeated 5 times to obtain a solution containing enough numbers of the bacteriophage. The supernatant obtained from the final centrifugation was filtered by a 0.45 μm filter, followed by the conventional polyethylene glycol (PEG) precipitation. Particularly, PEG and NaCl were added to 100 ml of the filtrate (10% PEG 8000/0.5 M NaCl), which stood at 4° C. for 2~3 hours. Centrifugation was performed at 8,000 rpm for 30 minutes to obtain the bacteriophage precipitate. The obtained bacteriophage precipitate was resuspended in 5 ml of buffer (10 mM Tris-HCl, 10 mM $MgSO_4$, 0.1% Gelatin, pH 8.0). This solution was called the bacteriophage suspension or bacteriophage solution.

As a result, the purified pure bacteriophage was obtained, which was named as the bacteriophage EK88P-1 and then deposited at Korean Collection for Type Cultures, Korea Research Institute of Bioscience and Biotechnology in Apr. 10, 2014 (Accession No: KCTC 12574BP).

Example 2

Analysis of the Major Structural Proteins of the Isolated Bacteriophage

Figure 2:
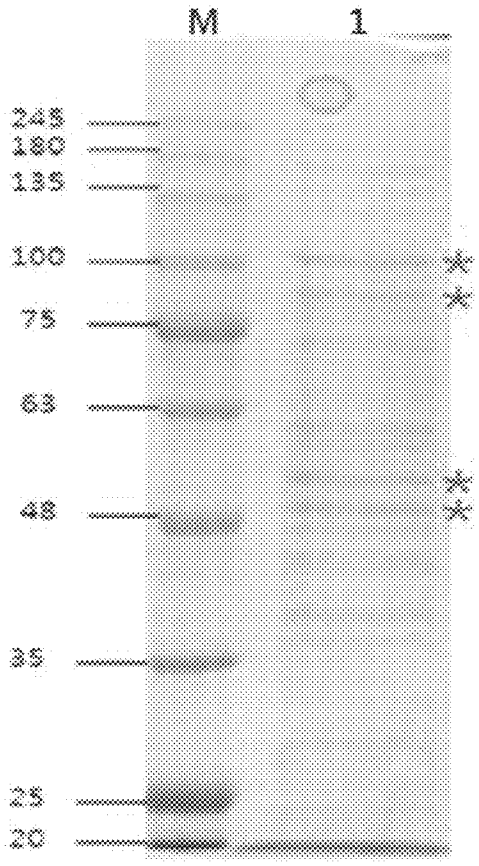
FIG. 2 is an electrophoresis photograph illustrating the result of one-dimensional electrophoresis performed for analysis of major structural protein of the bacteriophage EK88P-1, wherein lane M is the protein size marker and lane 1 is the protein sample of the bacteriophage EK88P-1. The major structural proteins are indicated by *.

One-dimensional electrophoresis was performed to analyze the major structural proteins of the isolated bacteriophage. To obtain the proteins consisting the outer wall of the bacteriophage, 200 μl of the bacteriophage suspension prepared in Example 1 was mixed with 800 μl of acetone, which was vortexed vigorously. The mixture stood at −20° C. for 10 minutes. Centrifugation was performed at 13,000 rpm at 4° C. for 20 minutes to eliminate supernatant, followed by air drying. The precipitate was resuspended in 50 μl of electrophoresis sample buffer (5×), which was then boiled for 5 minutes. The prepared sample was analyzed by one-dimensional electrophoresis. As a result, as shown in FIG. 2, the major structural proteins in the sizes of approximately 49 kDa, 53 kDa, 94 kDa, and 103 kDa were confirmed.

Example 3

Separation of the Bacteriophage EK88P-1 Genome and Analyzing the Characteristics The genome of the bacteriophage EK88P-1 was separated as follows. The genome was separated from the bacteriophage suspension obtained in Example 1. First, in order to eliminate DNA and RNA of *E. coli* host bacterial cells included in the suspension, DNase I and RNase A were added 200 U each to 10 and of the bacteriophage suspension, which was incubated at 37° C. for 30 minutes. 30 minutes later, to remove the DNase I and RNase A activity, 500 μl of 0.5 M ethylenediaminetetraacetic acid (EDTA) was added thereto, which was incubated for 10 minutes. The suspension was further incubated at 65° C. for 10 minutes and then added with 100 μl of proteinase K (20 mg/ml) to break the outer wall of the bacteriophage, followed by incubation at 37° C. for 20 minutes. 500 μl of 10% sodium dodecyl sulfate (SDS) solution was added thereto, followed by incubation at 65° C. for 1 hour. 10 ml and of the mixture of phenol: chloroform:isoamylalcohol (25:24:1) was added thereto, followed by mixing well. The mixture was centrifuged at 13,000 rpm for 15 minutes to separate each layer. The upper layer was obtained, to which isopropyl alcohol was added at the volume of 1.5 times the volume of the upper layer, followed by centrifugation at 13,000 rpm for 10 minutes to precipitate the genome of the bacteriophage. After collecting the precipitate, 70% ethanol was added to the precipitate, followed by centrifugation at 13,000 rpm for 10 minutes to wash the precipitate. The washed precipitate was vacuum-dried and then dissolved in 100 μl of water. The said procedure was repeated to obtain a sufficient amount of the bacteriophage EK88P-1 genome. The nucleotide sequence of the genome of the bacteriophage EK88P-1 obtained above was analyzed by Next Generation Sequencing (NGS) at National Instrumentation Center for Environmental Management, Seoul National University. Briefly, DNA fragment was fixed on the slide, followed by bridge amplification to form DNA fragment cluster. Then, SBS (Sequence by Synthesis), that was a nucleotide synthesis reaction, was performed by using the cluster as a template along with four different fluorescent-labeled nucleotides. This method is unique by the following characteristics: wherein DNA sequence is not amplified in a reaction solution like other methods but amplified on the slide where DNA is fixed with DNA bending to form sequence clusters. The formed cluster proceeded to sequencing group by group, and the obtained results were converted into each read sequence information, followed by analysis. 25 contigs in different sizes were obtained. The finally identified contig sequences of the bacteriophage EK88P-1 were presented by the nucleotide sequences of SEQ ID NO: 1 to SEQ ID NO: 25. These sequences were the partial nucleotide sequences that constitute the whole genomic sequence of the bacteriophage EK88P-1. The bacteriophage EK88P-1 was distinguished from others even with these partial nucleotide sequences.

Example 4

Analysis of the Characteristics of the Bacteriophage EK88P-1 Genome Using PCR

To disclose the characteristics of the genome of the bacteriophage EK88P-1, polymerase chain reaction (PCR) was performed. The primers used for the PCR were prepared by referring the partial nucleotide sequence represented by SEQ ID NO: 5. The primer information is listed in Table 1.

TABLE 1

Primer information

| PCR reaction | Primer | Sequence |
|---|---|---|
| PCR 1 | F-1 (SEQ. ID. NO: 26) | TATCACCCATGTTCCACGCT |
| | R-1 (SEQ. ID. NO: 27) | TGGTATTACTCGTCCGCAGT |
| PCR 2 | F-2 (SEQ. ID. NO: 28) | CCAAGTGCCAGTCCTAAACG |
| | R-2 (SEQ. ID. NO: 29) | ATGGGTCGGGTTACTGGTTC |
| PCR 3 | F-3 (SEQ. ID. NO: 30) | ACCCAATCTCCTATTCTGTCCA |
| | R-3 (SEQ. ID. NO: 31) | TGACTGATATTGATTCTGGCGA |
| PCR 4 | F-4 (SEQ. ID. NO: 32) | GGTTTCAACTCGAGCAAGGG |
| | R-4 (SEQ. ID. NO: 33) | TCGGTTGTATCTTGGGCTGA |
| PCR 5 | F-5 (SEQ. ID. NO: 34) | CGGAATTTGTACATCACCGCT |
| | R-5 (SEQ. ID. NO: 35) | CTTGATACGCAGGACCAAGC |

PCR was performed by using the genome of the bacteriophage EK88P-1 prepared in Example 3 as a template with Maxime™ PCR PreMix Kit (i-Taq; Cat. No. 25026, iNtRON Biotechnology, Inc.) according to the manufacturer's protocol. GenePro PCR machine (BIOER) was used as a PCR machine. PCR was performed as follows; predenaturation at 94° C. for 10 minutes, denaturation at 94° C. for 1 minute, annealing at 56° C. for 30 seconds, polymerization at 72° C. for 1 minute seconds, 30 cycles from denaturation to polymerization, and final extension at 72° C. for 4 minutes. Then, the reaction mixture rested at 4° C. The PCR product was transferred onto 1.5% agarose gel for the conventional electrophoresis. The gel was observed by Molecular ImagerGelDoc™ XR+ (BIO-RAD).

Figure 3:
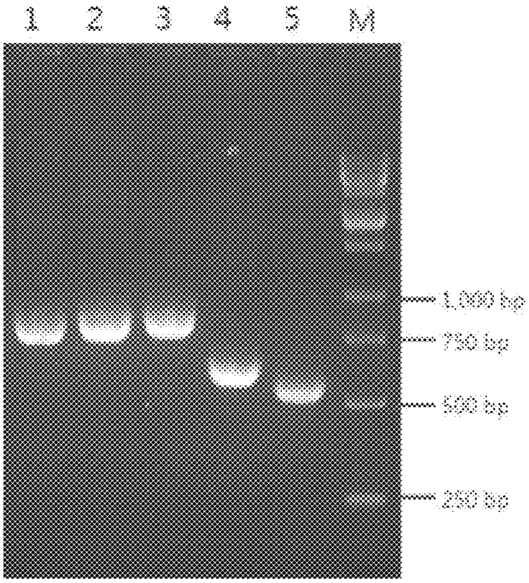
FIG. 3 is a photograph illustrating the result of PCR using the genome of the bacteriophage EK88P-1 as a template, wherein lane 1 indicates the result of PCR with the primers respectively represented by SEQ ID NO: 26 and SEQ ID NO: 27, lane 2 indicates the result of PCR using the primers respectively represented by SEQ ID NO: 28 and SEQ ID NO: 29, lane 3 indicates the result of PCR using the primers respectively represented by SEQ ID NO: 30 and SEQ ID NO: 31, lane 4 indicates the result of PCR with the primers respectively represented by SEQ ID NO: 32 and SEQ ID NO: 33, lane 5 indicates the result of PCR with the primers respectively represented by SEQ ID NO: 34 and SEQ ID NO: 35, and lane M indicates the DNA size marker.

The results of the PCR are presented in FIG. 3. An amplified PCR product in similar size to 834 bp which was the theoretical value was obtained from "PCR 1". An amplified product in similar size to 885 bp which was the theoretical value was obtained from "PCR 2". An amplified product in the size around 893 bp which was the theoretical value was obtained from "PCR 3" and an amplified produce in the size around 645 bp which was theoretical value was obtained from "PCR 4". In the meantime, an amplified product in the size of about 562 bp which was the theoretical value was obtained from "PCR 5". When the primers listed in Table 1 were used, the amplified products respectively in the sizes of 834 bp, 885 bp, 893 bp, 645 bp, and 562 bp were produced, which was the bacteriophage EK88P-1 specific characteristic. This characteristic alone could distinguish the bacteriophage EK88P-1 from previously reported bacteriophages.

Example 5

Investigation of *E. coli* Killing Ability of the Bacteriophage EK88P-1

Figure 4:
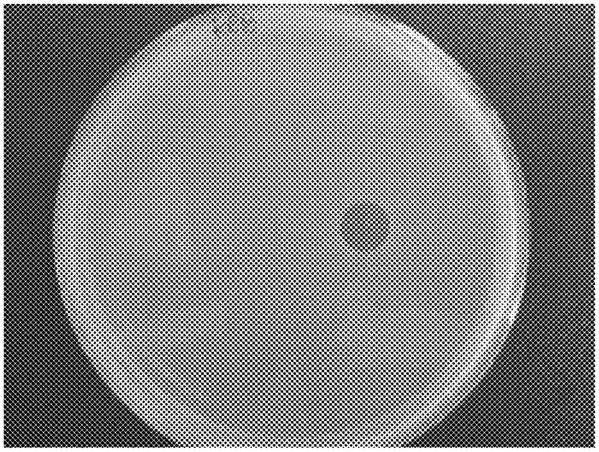
FIG. 4 is a photograph illustrating the capability of the bacteriophage EK88P-1 to kill *E. coli* cells. The clear zone in round shape is the plaque generated by lysis of *E. coli* cells on the dish.

The *E. coli* killing ability of the isolated bacteriophage EK88P-1 was investigated. To do so, the formation of clear zone was observed by the spot assay by the same manner as described in Example 1. Those *E. coli* strains used for the killing ability investigation were total 10 strains which had been isolated and identified as *E. coli* strains previously by the present inventors. Particularly, two of each strain of *E. coli* were used, which were two of *E. coli* K88 strains, two of *E. coli* K99 strains, two of *E. coli* 987P strains, two of *E. coli* F41 strains, and two of *E. coli* F18 strains. The bacteriophage EK88P-1 demonstrated *E. coli* killing ability to all the *E. coli* strains used in this experiment. The representative result of the *E. coli* killing ability test is shown in FIG. 4. In the meantime, the activity of the bacteriophage EK88P-1 to kill *Enterococcus faecalis, Enterococcus faecium, Streptococcus mitis, Streptococcus uberis*, and *Staphylococcus aureus* was also investigated. As a result, the bacteriophage EK88P-1 did not have the activity of killing these microorganisms.

Therefore, it was confirmed that the bacteriophage EK88P-1 had a broad antibacterial spectrum against *E. coli*, suggesting that the bacteriophage EK88P-1 of the present invention could be used as an active ingredient of a composition for the prevention and treatment of *E. coli* infections.

Example 6

Preventive Effect of Bacteriophage EK88P-1 on *E. coli* Infections

100 μl of the bacteriophage EK88P-1 solution ($1\times10^9$ pfu/ml) was added to a tube containing 9 ml of TSB. To another tube containing 9 ml of TSB, 100 μl of TSB was added. The *E. coli* culture was added to each tube to prepare bacterial suspension of $OD_{600}=0.5$. Then, the tubes were transferred in a 37° C. incubator, followed by shaking-culture, during which the growth of *E. coli* was observed. As presented in Table 2, the growth of *E. coli* was inhibited in the tube added with the bacteriophage EK88P-1 solution, while the growth of *E. coli* was not inhibited in the tube not added with the bacteriophage EK88P-1 solution.

TABLE 2

| Inhibition of *E. coli* growth | | | |
|---|---|---|---|
| | $OD_{600}$ | | |
| | 0 min. | 15 min. | 60 min. |
| (−) bacteriophage solution | 0.5 | 0.8 | 1.4 |
| (+) bacteriophage solution | 0.5 | 0.4 | 0.2 |

The above results indicate that the bacteriophage EK88P-1 not only inhibits the growth of *E. coli* cells but also can kill the bacteria. Therefore, the bacteriophage EK88P-1 can be used as an active ingredient of a composition for preventing *E. coli* infections.

Example 7

Therapeutic Effect of Bacteriophage EK88P-1 on *E. coli* Infections

Therapeutic effect of the bacteriophage EK88P-1 on the pigs having *E. coli* infection was investigated. 4 weaning pigs at 25 days of age were grouped together; two groups of pigs were raised in a pig pen (1.1 m×1.0 m) for 14 days. Heating system was furnished and the surrounding environment was controlled. The temperature and the humidity of the pig pen were controlled and the floor was cleaned every day. On the $7^{th}$ day of the experiment, all the animals were orally administered with *E. coli* K88 cell suspension using an oral injection tube. The *E. coli* suspension administered above was prepared as follows: *E. coli* was cultured in TSB medium at 37° C. for 18 hours and the bacterial cells were collected by centrifugation. Saline (pH 7.2) was added to the bacterial cell pellet to make cell suspension at a centration of $10^{10}$ CFU/ml. From the next day of the *E. coli* challenge, the experimental group pigs were orally administered with the bacteriophage EK88P-1 ($10^9$ PFU/pig) via the same way as used for the above administration twice a day. The control group pigs (bacteriophage solution non-treated pigs) were treated with nothing. Feeds and drinking water were equally provided to both groups. After the challenge of *E. coli*, all the animals were observed every day whether or not they experienced diarrhea. The observation was performed by measuring the diarrhea index. The diarrhea index was set as follows according to Fecal Consistency (FC) score (normal: 0, loose stool: 1, moderate diarrhea: 2, and severe diarrhea: 3). The results are shown in Table 3.

TABLE 3

| Fecal Consistency score | | | | | | | |
|---|---|---|---|---|---|---|---|
| Days after *E. coli* challenge | 0 | 1 | 2 | 3 | 4 | 5 | 6 |
| Control group (− bacteriophage solution) | 1.0 | 1.5 | 1.5 | 1.25 | 1.0 | 1.0 | 1.0 |
| Experimental group (+ bacteriophage solution) | 1.0 | 0.5 | 0.25 | 0.25 | 0 | 0 | 0 |

From the above results, it was confirmed that the bacteriophage EK88P-1 of the present invention could be very effective to treat *E. coli* infections.

Example 8

Preparation of Feed Additives and Feeds

Feed additive containing bacteriophage at a concentration of $1\times10^9$ pfu/g was prepared using the bacteriophage EK88P-1 solution. The preparation method thereof was as follows: Maltodextrin (40 weight %) and trehalose (10 weight %) were added to the bacteriophage solution. After mixing well, the mixture was freeze-dried. Lastly, the dried mixture was grinded into fine powders. The drying process above can be replaced with vacuum-drying, drying at warm temperature, or drying at room temperature. To prepare the control feed additive for comparison, feed additive that did not contain the bacteriophage but contain buffer (10 mM Tris-HCl, 10 mM $MgSO_4$, 0.1% Gelatin, pH 8.0) only were prepared.

The above two kinds of feed additives were mixed with feed at the volume of 1000 times the volume of feed additive respectively, resulting in two kinds of final feeds.

Example 9

Preparation of Drinking Water Additives and Disinfectants

Drinking water additive and disinfectant are different in intended use but same in the composition, so they have been prepared by the same manner. Drinking water additive (or disinfectant) containing bacteriophage at a concentration of $1\times10^9$ pfu/ml was prepared using the bacteriophage EK88P-1 solution. Particularly, to prepare drinking water additive or disinfectant, the bacteriophage EK88P-1 solution was added to buffer solution which is $1\times10^9$/ml, which was well mixed. For the comparison, the above buffer solution itself was used as the drinking water additive (or disinfectant) that did not contain the bacteriophage.

The prepared two kinds of drinking water additives (or disinfectants) were diluted in water at the ratio of 1:1,000, and then used as drinking water or disinfectant.

Example 10

Effect on Pig Farming

The effect of the feeds, drinking water, and disinfectant prepared in Example 8 and Example 9 on pig farming was investigated. Particularly, the investigation was focused on mortality. Total 30 pigs were grouped into three groups, and each group was composed of 10 pigs (group A: fed with the feeds of the present invention, group B: provided with the drinking water of the present invention; and group C: treated with the disinfectant of the present invention). The experiment was continued for 4 weeks. Each group was divided by two sub-groups comprising 5 pigs each. The sub-groups were divided according to the treatment of the bacteriophage EK88P-1 or not (sub-group-①: treated with the bacteriophage EK88P-1; and sub-group-②: not-treated with the bacteriophage EK88P-1). The pigs used in this experiment were weaning pigs at the age of 20 days. The pigs in each sub-group were separated each other and raised in a separated room placed at a sufficient distance from each other. Each sub-group was divided and named as shown in Table 4.

TABLE 4

Sub-groups of pig farming experiment

| | Sub-group | |
|---|---|---|
| | Treated with the bacteriophage EK88P-1 | Not-treated with the bacteriophage EK88P-1 |
| Fed with feeds | A-① | A-② |
| Provided with drinking water | B-① | B-② |
| Treated with disinfectant | C-① | C-② |

Feeds were provided according to the conventional feed supply method as presented in Table 4 with the feeds prepared in Example 8. Drinking water was provided according to the conventional water supply method as presented in Table 4 with the drinking water prepared in Example 9. Disinfectant was treated to the pigs three times a week with taking turns with the conventional disinfectant. That is, on the day when the disinfectant of the present invention was sprayed, the conventional disinfectant was not treated. The results are shown in Table 5.

TABLE 5

| Group | Mortality (%) |
|---|---|
| A-① | 0 |
| A-② | 20 |
| B-① | 0 |
| B-② | 40 |
| C-① | 0 |
| C-② | 40 |

From the above results, it was confirmed that the feeds, drinking water, and the disinfectant prepared according to the present invention were effective in reducing the pig mortality. Therefore, it can be concluded that the composition of the present invention can be efficiently applied for the improvement of productivity of pig farming.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A method of treating or reducing mortality due to *E. coli* diarrhoea in a non-human animal subject, the method comprising the step of spraying on the non-human animal subject or administering orally to the non-human animal subject a composition comprising as the active ingredient an effective concentration of the isolated bacteriophage EK88P-1 having the genome composed of nucleotide sequences set forth in SEQ ID NO: 1 to SEQ ID NO: 25, wherein the bacteriophage EK88P-1 has a broad antibacterial spectrum against *E. coli* and is deposited under the accession number KCTC 12574BP.

2. The method of claim 1, wherein the composition is sprayed on the non-human animal subject in the form of disinfectant.

3. The method of claim 1, wherein the composition is orally administered to the non-human animal subject in the form of a feed additive or drinking water.

4. The method of claim 1, wherein the non-human animal subject is a pig.

* * * * *

SEQUENCE LISTING

```
<160> NUMBER OF SEQ ID NOS: 35

<210> SEQ ID NO 1
<211> LENGTH: 29227
<212> TYPE: DNA
<213> ORGANISM: Artificial Sequence
<220> FEATURE:
<223> OTHER INFORMATION: partial sequences of Bacteriophage EK88P-1

<400> SEQUENCE: 1

gcaaaaattg cagcaaagat aaattttttc atgataatct cctcagtagt ttatgtttat      60

agtatctcaa ttttcaacaa aagtaaacac tagtagaagc aaacagacaa attacaataa     120
```

-continued

```
ttggtgattt cagtttcatt cttctcctcc atgttgatga acatattctt tttcaagtct    180
agagcacaag ttttcatatt caactaataa aaatgaatca agtgcgttat ttctatgctg    240
acaccgttct tgtaaagaat ccatctctga acgttgttct tgtgttaata attgataacc    300
tgatacttta gacattttat tctccattta ctcgtttgtt ttgataggtc tataataaca    360
tgtttaaaac aaaagtaaac tattttattt cctcaagttc gttaatcaat aaaagttctc    420
tgacgctaaa aacaaagaaa aatgtgttcc catcaaccag aacatgaccg ctaatagaac    480
accctctgcg gaatttagaa acttcacaat ctagaactgt aaagggtttt aatcctatga    540
ctttagctgt gcgtctattc agttcacaac cactcgcgaa tttttccaaa tcttcttctg    600
atttaaactg atattctcta ttaactagca tcattttctt ttctccgcga ttagctgata    660
gaattactat aacacaactc tatcagcttg taaactacta ttttaaaact tctgtataat    720
cacatgttac aaactgtttc tctaacttga cgattttacg aaagtatctt ttgcattgac    780
gaatctgtcg cttcgtaggg cgcacagcaa acttaataaa ttccactcga ccaaatggag    840
ggctttcttc tgccggaata tctaatacta attcccacgt atctgcaata agtgctttga    900
attgagtatt tttcctgacg ttatatggag taggtttaaa taaaacaata tgcatattat    960
cctcggcaat ccacttcgca tactttcttg tcatcaatga aagctttaac tagcgcttta   1020
ttaacttcag catattgatt agtagcccat tgaacgtcat ctttcatcat tgtggtttct   1080
ttagtaaaca tgctttcatt cttaaaccac cccataaaaa ctacctttac caattccata   1140
acaatctccc catttaacca acaagactac tataccatag tctcgtcagc ttgtaaacta   1200
aaattttaat tcatttgcca aagcatctaa ctgagctcga gtcgattcgt ttctttgata   1260
gcgattctgc tcagcctgaa tctgctgtga acctgctact tcgttcactt cagttggagt   1320
agaatcttgt tcaatttcta cccatttctg atttcctttt tgaacaccca tcaaaaactt   1380
attccattta ttcttatcac catatcgtga tttgatttgc ttaatgagtt gttgttcagc   1440
agctgctaac tcctcggttt caatgaccgc aagcataaaa tcagctgtcg ctggaagacc   1500
agcagattct gcgatatcac tcatgttaac atcggaagag tcccaagctt gtttaccaac   1560
ctgtgctgca gtccaaagaa cagtttcagt ttcaacagcc agagcacgca attcttctgc   1620
gatggcttta acagttgtgt aactattttc tgaataaact ctaatgcggc aagatttaca   1680
aatacctaga tagtcaacaa taatgattgt tggaacaaaa ttcttcttga gctttaattc   1740
atttaaaagt gatcgaaatg tattagcgtc tgctccacca gtaggatatt gcttaacgat   1800
taaacgacca agggtagatt tctcacgcca tttttccatt tttcctttat attcagcgta   1860
agaaatatgt ccatcatcaa tatcgtcaag agaaacatcg agcatgttag catcaatacg   1920
tttagcacag acttcttctg ccatttccat ggagatataa agaacgttat gaccaagctg   1980
caaataatct gctgctaatg aacaaagtcc taatgattta ccaacgttaa cgccagccat   2040
taaaacgttc agtgttccag tctcagctcc gcctttagta attttgttta gaattctgag   2100
tttaaatgga accttacgag ctttattcat ataagatagc caacgtgctt cgtagtcatc   2160
catccaatca tgaccaacgt agctatcaaa tgaaattgat aatgcttgcc gcatgatgtc   2220
aggaatagca ccaacatccg gcattttctt atttcgtttt tccggaggaa gctcagcatt   2280
agtttgaatt tcaattattt tagacgtagc attaaacatc gccctttgct gaacatattt   2340
ttctgtttct tttactaacc agctgtggtc ttctggagaa tcggctagtt ttgaaataag   2400
tgtttttaca ccagaatatt ctgtttcagt aaatgaacta ttttctaatg caacatttaa   2460
cgcattaata gatggaacgc tatgatactc attaacatga gatttaatta atttgaatgt   2520
```

-continued

```
atttttagct ggaccacttt caaaatattc tgaatccata tatggccaaa cttttgaaaa   2580
ataagcttga tcaaatatga gatgagaaag aataatttct accacactta ctccttaaaa   2640
gaatttaaat tttttctttg accttttatt aaatgcatct tgtagttgca ttgtaataca   2700
tttttctaca tgaggagcta actcagcttt tctttcttgg tcaagaacag caaagtccat   2760
tacaaccttt ccatcaaccc aatctaattt tgtcacatac acaatgtgtg tagaaccatc   2820
ttctagttta atgacaatct cctggataac attttccatg gcagatttaa ttatcttaag   2880
agactcgtta aaaagacgtt cttttctttc ttcttccccc tccgaagagg gggattcatc   2940
gataatttct agatctaagt ctaaatcatc tttattcatt aaattcttcc atatcactta   3000
actgttcgag gtcagtttct aaatcagcag ctgatttact tttactttct ggagatttaa   3060
atttttcaac ctttgagtta atcaattcat caacttcagc ttcaataatt tcattactat   3120
caatagcacc taactgataa gcacgtttaa tagcatctcg gaatggttga tgcttaaata   3180
aaggacccca gaatgtagtg cagttagtat cttttgcacg ccaagatttt tcttcgcgaa   3240
tcatctcgcc ggtttcttca tcaagaaatt cacgagcata ccagccattt ttaggtttta   3300
ccacgaatcc taattctaga gccatatcta acaatccaga ataaggatcg ataccaccgt   3360
caaatttaac atcaataaaa aatttacttt tttctttaac ggtacgagat ttttctacat   3420
ttagaacaaa ttgataccct tgaagatcag aaccatcttt aatctgacgt ttaccgataa   3480
tgaatacagt atcagccgaa tacattacgc ctgtattgtg tgtaacgata ccattttcta   3540
aaacataatg ctctacgtca gcaacagaca aatcatagac ttctttttta ccaacagatt   3600
taacagattt aattttcata ctttaccttg tgtttcgtag tagctagttt caatatacat   3660
atttcatgaa agcataatct tgattgtcgc gttcattcca aattctttta ccatatcttc   3720
gaatgtagtg cgaacccgta aagaactcgc attggaatgc cttaaccacg tgcatctact   3780
gcataagccc atccttttgt gttagcttta attttgttga taattgtgtt aggattaatt   3840
cccagcgctc ttgcagcagg tctgacgccc cggtattcaa taccgtttat gataacgcct   3900
ttttgtctag gatgagaatg ctttaatctt ttctttgctt tttctgatat ttcattaatt   3960
gtttctttgg tgtgtttctt accatagaac ccattgtttt ctccggtaat accttctgat   4020
atgtgcttac ggtgttcatc agaagatttc acgccttttg tgacgccaac atacacacca   4080
gatttaacaa gcggatggtt tctttcaaga cgaatacatt tacctgttat atgatgcttg   4140
tatgatgcaa aatcagcatt agcatatgaa ttatgtccac aagcataatc caaattaaaa   4200
taatctggat ttgttttaac gtttacttgt ttctgataga aattttcgcg ctctagcagt   4260
ttagcatgtt taatatcatc atattgctcc agtatttcaa cagtaacatt attgataaaa   4320
tcatgatatc cgggatatct cgatgagcca tagtactcgc gaccacgggc gtcaataatc   4380
ttaccgtcta cataagaagc atttgtcttg cttcctatgt agtaatacgg cggagtgccg   4440
tttttaattc tatcgttgaa cacaatttta tagacaaaat tcatatgggt acctcaaaaa   4500
tatacattag tccggtaccc atatttatta ccttacaaca caatccattc cagctactaa   4560
atctttagct tcaacccaag ttggaatgtc tttaaccatt accaggaact tgtgggtatc   4620
tgaagtagtt actttataac cgtcttcgaa ttcaatttcg aaacattcag gagtaccttc   4680
agccagagtt tctgggtccc aaacataagt tacttcatta tcaccgacca tggttttaac   4740
acgttcacct ggacgaatat cttcaactgc tttagtagaa ccatcggaca tctggatttt   4800
agtaccagca ataacacaac cacctgtcat cacggtttta ctaaacattt caattgtttc   4860
```

-continued

```
aattgtatgg ttaaccgcaa cacatggaat atttttaatg ctaaaataag gagtaacaat   4920
acggaataat gacttcagtg atttagcacg agtcatatct gccacagatt tttcattcaa   4980
ggcatcttcc gtttctttct tagaagccat attaccaatt gagtcgatga atacaataac   5040
cttttcacca cgctcaatag cttcaagctg gttcaccata tcaattttca gttgttcaac   5100
tgactgaatc ggcgtatgaa ttactcgttc cgggtcaact cccatggatc gcaaataagc   5160
tggagtaata ccaaattcgc tatcatagaa tagacaaacc gcgtcaggat atttgttcaa   5220
atacgctgca accatagtca aagacatatt tgatttaaag tgtttagaag gccctgcgaa   5280
aatagttaaa ccagactgca taccgccatc aatcgcacca gaaatagcaa tattaagcat   5340
tgggattttt gtacgaatta catccttttc attaaagaat ttagatgtag tcagttcagc   5400
agtcatttta gaagtggaag ctttaatcaa acgggatttt aaatctgcaa tagacattca   5460
tttttccat aggcatcatt atattttcct cactggttaa agatagagta attataacac   5520
aataaattta ggcattaatc aactgctatt ggatgaatag cattaaactt atgaaatgct   5580
tctgattttt ctttacgcga aacacacatg cgaagaacct ttaatggctc gtcttcttca   5640
cccaacgatt ttcgttttc aatattcgat gttttccaac gagcttgctc tggaaactct   5700
ctattgattt gttcaagcgc tctattatgt ttagaattac tacgaattga actacaccca   5760
ccgggagcct gtgattttcc agatacaact agatatttga acaaggccaa atgtggataa   5820
ccttgattaa ttaaattgag aaatgcatac atatcttcgc ataaatcaat ttttccatac   5880
ccaatttgtt ctgtcgtaag ttttccgagg tcataccatg tattcgtgaa tccatatgag   5940
ttttcacgat aattacccca agatgaagta attttaaaaa ttggtagacg agcatgacca   6000
tgataatacc cgcaatccat ggcatcttca acgtattgaa tcaattcata gaactgttca   6060
cgagttaatt gattaatttt atctacacgg cgtttatcgt ctctctttcg tattgaactc   6120
atacgaatag tagtatcatc atcaatcatc cagattcgtt gacctgcata catatcagta   6180
attgctttac gagtaccggc aattccgttt acatcatcag gaatagttac aattttagct   6240
ctagacccat aagcatcata ataagctttt tcttcgtgtt cacgcactac aatatggggt   6300
tcataatcag tcggaaacat atcaagggca gaaactgccc ctacacgttg atagcttgga   6360
attacgaatt gaatcattta agtgccttac atttgtcaaa atggtatctt gtcatatttg   6420
gcccacgtcc ttttagtccg caatgcggac atatttttc tatcaaatta tgaggttttc   6480
ctttacgatt tttagacatc gtttctttaa ttattttagc tttttctgcg ccaaaaattt   6540
cttcataagt tttaccagaa ttttcctttg ctcgatttat aattccatat gcctgctcat   6600
ttttaccata cattggatta ccttcgcctt tcattctttt agaatgatca ggacgcttga   6660
ttccacgaaa ggcatttccg cacttatatc tttcttctgg agatagtttt ttaccgtaca   6720
ttccatttaa tttgcctgga aaacttcctc cccatgcttc attctttaaa ttatatgaat   6780
ccggacaatt agcagcatct aaacaagtta aaataatttc ttcaacctgt ctaaacattg   6840
gtccttcata taatatttct ttattaaagg attttattcc atatttcttt ttagcatgtt   6900
gccaaactac acccgaacca tcataattcg ggttgtgacc atcatgactt cctatatacc   6960
actttttagt tttaggatgt ttatacttat aaacatgtgg cacatttact tccattttcc   7020
agtataatcc tttttagcaa tatgagtttc accggtgttc caccaatggt caactaaata   7080
aaactgattt tcgtacacat gaagacttcc aacgttccat ataatagaac ctgctttata   7140
ttgccgcgat gggtcgcctg cattcaaatc agatactaat ttatctagta cgtatttttg   7200
ccaagcataa tcattacgat agcctgccca gcaatcattg cttctcatgc taacaaccgc   7260
```

-continued

```
attgattttc ttgtcacgaa ttaagtattg tactgtattc gtacacatga aatctgacat   7320
accatcttta ttatagtcaa attgcataga tggacgagta taaatcatga taccacgtcg   7380
agaatcagga ttttgaccaa gttcagctaa acacatatca tactgggcat agttatcttc   7440
tgaccagata gcccaaccat aattcgagtt aatttcacct ttagaagatg ctacttgttg   7500
ccaaatcttc ggtgtttcac ccggaatatc tttaacgaac aagctcttag atttatacca   7560
ttcaagttca cgctgaatgt attcatcatt aagagcgcca aaaataaacg gttcatctgc   7620
tacaaatgat gcgccaataa tttcaatagt tttaacgcca gttttatcaa ctacgaaatc   7680
tttttccttt aatgcaagcc ccaaatgaag acggatttct tcaactgtca tagagtcact   7740
aatcatttaa acctcaattg atacattcat atttaacttg taacagtaat aaactccaac   7800
ctaaaacaat agttggaatc ataagaggaa ccgttacact atagtatata cttattataa   7860
ccatcaagat taaaagcaat gctgctataa ttttgctttt cattccttct ctctgatgat   7920
aattacctga tttggctgcg cagacttttt agtttcacct gcaattgacc aaataaatgt   7980
aataaaccaa ccaataattg accagttaaa cagtaaagat gtgaaaaaga ttcctactgt   8040
tgattttgac ccacgcatca aagcaataaa ccatggaagc gtgtatataa taatagccaa   8100
cacacccgaa actaaaacca taaaaattga acctgctact aaagtttcca tgtttcctc    8160
acttagtcaa attttttaca catgaattat aagaattcac tacatactcc atcggagcat   8220
ttttacctgt gcgccattgg taattattag cccaatttgc ccaaagttca gcgcagtaat   8280
tttcaatttt ttcttcgcgt gtaattacat ccgaattacg atatgcttga gcggattcat   8340
ctggacgaat agcctcgtca aaattcgcct gcatttgttc tactgtctgt tttggagctt   8400
ctttataaca cttgacatta ggattataaa atttgcttga acagtttaca atttttcctg   8460
catcagactg atttactacc ggtccttgag ctacacaacc agtaagacct aatgcaataa   8520
ccaaaatagc gattttcatt tcattctcca aatccgtatc agttgatagt tgtatagtac   8580
catggaagaa cagggatgta aactgttttg tgaaaaaatt tttagggaat tcaaagggtc   8640
cagaatcatc tgtttttcat aagtatagat ttatattact tgtatgaaaa agggacccgg   8700
aggtccctag atttattcta tcagccaaac aggaagtcta acgaagcttt ttcttcatag   8760
tccataccag ccgattcaca catacccgca agcggtttaa caaacgattt ttggaacaaa   8820
gttgagtagt caatccaaga tagtacatca gaacgaattt cttttggaag ttctgtaccc   8880
gatggccaag caatgcactt gtcaccaaat ggatttcctt cacgtaatgg aagaaccatt   8940
actttatttc catccaaaat tggagctaca cccagaccac taacagctcg acgataagtt   9000
agcacaccgc gaatatggaa cgggcattta aatcctggcc aacctttatc atcatatttc   9060
gctatatcgt tcgcagtttt tacttcagca ataactttat agtcaagttg acgatattct   9120
ttctcgaagt tcttgtagta ttcttggaca gactcttcac cttcttgaag aatacgacga   9180
atactttctt cgagagcttc ttgcactgct tttggtgttg aactctgctg agtttccata   9240
cccatgattt ttagatgcgg ttcagcaaat cgtttatctt ccatatcata aacgttcaga   9300
gcataacgct ttttcgcttt ccaaaatcca ccaacgccct ttgaaccaag tggagggcaa   9360
gaaatagctt cacggtccat atgcatcaga tgctcgcggt tattcatata atcacataac   9420
tcacgatatg caacatcaat cataggttcc atctttttct taccgaactg attcatgaat   9480
tcaactaaat cattttgttc tttaaagcgg tcaagaccta ctttttcaat aactttatct   9540
acacagacat ataccgaatc agtatcacct gctgcgatga aatcttcacc atcagttcca   9600
```

-continued

```
cacaccttat tcaggtattc attaatttta cgagcaatcc actgaatacc gacttgacca   9660
aaaattgtga tagcagtagc atttcgcaaa tcatagtaac ggaaatgaat attaccaaga   9720
gcaccataaa gactgttgat aagaatttta cggttcagct gatttgtgtt agcaagtgta   9780
gcagcttttt cacattcttc aatcaaacta ttaagaacag attcagtgta attcgataat   9840
tcgtttaaga aatcatcact gaacttaaca tatcgttcaa cttctggttt agttgagcaa   9900
gaccctgcac ctttcataat aatcttttta atagcttcgg cattcatttc ttcagcgaac   9960
atttctttt tccaatcttt acgctggaaa aatactttag cgatttcctt tggaatgata  10020
ccttcttggt gcttatcata catccatcca ttcggagagc aagaatattc atcacttggc  10080
ttaggagctg ttcctgcgat atattcatga attggatgaa ctttaaactg cccacgaata  10140
gtctcaggac taatgttaac ctgacgaata atgctaggat acagagacgt caagtcaaaa  10200
ctcataatgt atcgacgagc aatcggttta ggttcaaaca caaatgcgcc tggaaaactc  10260
tgtttaacgt gcgaaccttg ttgaggaata accttatgtt cacctttcag cgagttaaaa  10320
ataatagcat cccaagtttt aataggactc attacaccag aaaaaggcat tttagcgtaa  10380
taagacatac ttaaaactag atcgataaac ccacgaattt tatcaattgc ttgaactgat  10440
tctacgtcaa tgatgttata actaatgtat cgttgatgat tagtctcacg aagtttatta  10500
ataggaccat cgtacggcaa tttacctttt ttggtttcat gttgagcaac tgattccaaa  10560
gagaacgatg gcaaattagt aaatgcgaac ttcttgtata aatctaaata atcaagaata  10620
gatacgccat caatagaata aatttctttg ctaccgtaca tattttgaat tagtttagat  10680
tttactcgac cgattggaga gaagcgtttc atactgcgtt caccgagaac cattttaaca  10740
cgattcatga tatacggaac gtcaaatccc tcaatattcc aaccggtaaa aatagcaggt  10800
cgtttctgtt cccagagatt aatatattcc atgagcatat cacgctcatt atcaaatggc  10860
atataaatta ctcggtcaag aatttcttga ggaacttcat caccaccttc acagtcaagc  10920
ttagcagcta actttgcatc ccattttgat actgaaccgt acattgaatt caacaaatca  10980
aagacgtaaa aacgatcgtc aattgaatca taatgagtga tagcatcaat ttcatattct  11040
gctttcattg ggtcaggaaa tttatcacca gtaacctcaa tgtcgcagtt agctacacga  11100
acaaattttc ggtcataaac aatttctgaa ccatatgtat cactgatata agcgagttta  11160
aaatcgttca taccgagagc ttcgagaccg atgtcttcca ttcgtttcat ccaatctcgt  11220
gcatctttca ttgatggaaa tttttgagga gcacaatttt taccataaat gtctttgtat  11280
tttgactctt ccttacagtg cctaaacata gtcggaagat attctacttc acgagtacgt  11340
tcctttccat tttcatcaat ataacgttca acaatgttat ttccgactgt ttcaatagag  11400
atataaaatt ctttcataga tattccttag tttatagccc gagttattag gctcttgata  11460
tattatactc caaataaggg gccgaagccc cttgcttaat taccaatcgt atatttagga  11520
acgagtttcc attcatgttt ttgtttaaaa gaaataactc ggaagttatt agttaaatct  11580
ttcataaaag ttctttgacc gggaacgatt tcaatcagtc cccaatcttc taacagccat  11640
gcaatcgaat cacgacgaac ttcatcttct tctgtcattt caacttgacg gccatccata  11700
cgaagcattt ctttaaaatg aacgatatag tatagtcctt ttttctgaag aatatgacag  11760
gactgataca gaactttatc tttattatta gcaattccca tacgagtcaa agtttctttt  11820
actttcagaa aatcttcagg ttttttaaga gtaatttcaa tcattttacc attccaatgc  11880
tagttttttg agttgtttct gttcttttac gttcttagtc acttctttca aaaaatcatc  11940
cgtgactaat cctttaagtt cttttaatac taaaggtagt tttccatttt tagtaagaat  12000
```

tgatttatag ttaattgcat catttgtgtt aacttgatac cgcttagcaa gtaacttaat 12060
aatcaatact tcggtggaat cttcaactag ttttgcccat ttaccatatc ttttaccacg 12120
aggaacagca gccatcagat aattaaaatg ggcttcatcg cttaagcctg atccaattaa 12180
attcatagca tatacagctg gcatgcactc tggaaattgt gataatgcat tttcaaccat 12240
gaattttgaa taatcttttt gagcaataga gcatttagtt ttattattaa tagctccaat 12300
tatttcaaaa aattcatttt cagctttttc tttaaaagaa tcagcagcgg attggacagc 12360
tgtccaatct tttgaatacc aagcaacttg atgctcgttt aattgaatat catcttcaaa 12420
taagctcata tcacttccac tgcatttcgc atgctaattg aatgaaaaga taagctaaat 12480
gtaattcagt attagctgca ataccatgat actgattatt ttcgccgaca atttcgtaca 12540
tacgaataat actctgtgga gttacacgtg aatagatttc ttcggcaagt ttacctacga 12600
accacgaata atcagctgca tattttggtg ctaaagctct gagctgttta acatctttat 12660
ttttgagaga ttcaagaaca tcatcaatag caccacgatc gttagtaacc agtgataaaa 12720
taccagcatc caaaacacct ttagatgaat aactatcgag ctcgccaata gttttacgaa 12780
aatcaggaaa attcttttta accaaagctg ctacaacttt catatcagct atagcaattc 12840
cttcatgctt acagatttca gtcaatcgac gaatcatctg cttcatcatt tcaattttat 12900
cttcatcagt cggttgaccg aatgtaataa ctcggcagcg cgactgaagc ggtttaataa 12960
taccatcaat attgttagca gtaataataa tgctgcagtt tgaactataa gcttccataa 13020
aggaacgaag atgtcgctga gactctgcta accctgaacg gtcaaattca tcaataacga 13080
ttactttttg acgaccatca aatgaagctg cactagcaaa attagtcaaa ggaccacgaa 13140
cgaaatcaat tttacagtct gatccattca caaacatcat atcagcattt acatcatggc 13200
acaatgcttt tgctacagtt gttttacctg ttcctgaaga aggagaatga agaataatat 13260
gtggaatctt acctttactt gtaatagatt taaaggtttc tttatcaaag gcgggaagaa 13320
tacattcatc gatagtagat ggacgatatt tctgttcaag aatgtgttct ttttcattta 13380
cagtaatcat aatttcctca ttcaagtttt agtgtaaatt ataaagggcc gaagcccttt 13440
attaaaagtc gtgggtagaa tcagcttcaa gagctactac ataattcgca tgttcacctt 13500
caaatttagc agcgccttgt ttaccttttg cccagagcag aagtttataa tttcctggtt 13560
gcattttcat atttgccata ttgataatga aattaaatgt attttcacca tcataatcac 13620
caagagtcaa agaatattta acacgggtca aagcagaatc ttctacttta ttaaaaccgt 13680
taattacgat tttaccttct tttactgtga tagcaattgt atcaatctgc agaccgcgag 13740
atacacgcaa tagctgttga aggtcttcag ctttaatttc ggtaacaaca gatgctaccg 13800
ggaatggaat cggtttatta ggagcaacta ctgtactcgg atcggctgct ggccaaaaaa 13860
ttgttgagcg agcatcagca attttaatat taccatcttc tgactgggaa atttctgcat 13920
catcattaac taaagacaga ataccgagaa aaccgttcaa atcgtaaatt gctacatcaa 13980
aatcaataac gtcagaaata tttgcttccg cataagttgt accattaact gcgcgagtca 14040
taataaattg accggattta agcataatac cggagttaat agtagcgaaa tttttcaaaa 14100
tattcagtgt atctttagac agtttcatgt aatttccttc aattcaaatg agatttaatt 14160
ttataactaa tttaataaag caattaacga ttaaaatcgg cagcaattgt ttccgcaaca 14220
agttgagcag caacaattag acgttcatct gcattaccac aataatcgtc ttcaaggcgt 14280
tcaccacatg aagtcataat aaatttagca ccagcattta gagattctgt agtatgtttg 14340

-continued cgcattagtt caatccattt attacttact tcacgatcga tagcttcata atacgcatga 14400
cgagcaggtg cagatttaat tttattctga ataacttcca tcgcgttatc agaaagagac 14460
aaaacccatg ctcgacgaat tttattttgg ttttgtggat ttgattcaga acgcacgtgt 14520
tttggctgaa tatcttttac atcaacagta taattcacag taattttagt cataatacgc 14580
ctttagtcat aataatcagt aacagtccaa gcttcatttc tattggacat tatttttgta 14640
tattctgatt taaatgcatt cctaagcata gattcagtaa ctatatgctc ttcattagaa 14700
aaattatttc tcagaatata tcgttttatt tcaggaatag ttaatagatg ctgtccagtt 14760
gaatattcca tgtttttcct ccatagagat tatactctaa taaattaaag cataatctct 14820
tataaattaa accattacag taaatcgacc aactttcttc atttgaagat gctgaccata 14880
tgcttgtggg tcgtggtctc tatgtgaaat aacaaaaaca ttagtatttt ttaaactatc 14940
taaaatagtt gaaatagctt ttacaccttc aacatcagtt gctgaatcaa aaacttcgtc 15000
aagaattaac gtgtttattt taacacctga aactttttca gcaatatcac gccaagtaaa 15060
taaaagagca atatcaattc gtgctttttc gccttgactg aatgaagcat aactaaaatc 15120
ttcacgaccg cgggatttaa ttgtctcatt aaattcttca tctaatgtaa acacataatc 15180
agcttccatt attttaagat aatggttaat ctgcttatta aataatggaa tgtacttttt 15240
aatgatagca cctttaatac cagaatcttt gagcatatca gtcaaaattc ctctgtggta 15300
tttttccatt actaaattag tttttgtctt aacaatttta tcaagttctt cttgaagcag 15360
tgctatttca tcagcatggt caataaactc agatgatgct tttctatag ctgctttaac 15420 ttttttagct ttatctaccg tcgtgattag agattgcttt ttattgcgaa tatcattcgc 15480
caacgtctgc tgggttttaa tattatctcg gtattcatca acgagaactt ttaaattatc 15540
acgatgtgtt gaaagctgtt caaacgaatg cgtgcattca gaaactttat ctttaatttt 15600
agaaacaact ttatcaccgg aacttaattg tgacaaacaa gttggacata atccaccttc 15660
gtgatacata ttaatgactt tattatacga gtcaattttt gatttaatta aaaatgcttc 15720
ttgaccgatt ttattaaatg catcagtcgg gtcttcatcc aaaacaatat taactaatct 15780
ttcattagct tcttctattt ccgattttaa cgttctagct tcttttgcca aatcatcata 15840
catattctgt agacgagtaa ggttatcacc agttaatttt ttctggcgtt caacgttatc 15900
attatatatt ttaatttgtt ggataatact atctttttta acatcaagca cttggttttg 15960
tgaatttaat tcacgtatta gtgctttatt aagcttatcc atttcagcta atgttcctac 16020
ctcgagcagg tcttcgacaa gctttcttct tgcaggagtg gataggccca taaaaggggt 16080
atatccagcc gtgccgagga cgacgatctg tttgaaactg gcatatgaca ttccgataag 16140
ctgttcaaat tctgcttgga aatctttact gctggcagat tcattaagac gtgtaccgtt 16200
aacggtgatt tcgaaaacat ttggtttttg tcctcttttg atatagtact ttttctcatc 16260
atattccatc cacagttcaa ctaaaagttc tttcttattc gtgctgttta ttaattgacc 16320
tttctttacg tcacggaatg gcttgccaaa aagcccaaat gtgatggctt ctaacatagt 16380
agacttacca ccgccatttc gcccggtaat aagagttttt tgaaccttat ctagttgaat 16440
gtcaatagga tttccaccta ctgacattat attttgatac ctaactcggt ttagtttaaa 16500
attcttcaca aaagattcct tttaatgtat cttttagacc attctatcat atcatcataa 16560
tctaaaaagt attcatcaaa ttcagccatg caaacaacgc cttgtgctgc ttttgatgtg 16620
atataaatta ttccaacata tctagaatct tcttcggtgt aatcaatatt tgctatgaat 16680
tcatcattaa tgtcaaatgt cgaaaacttc acagtatgca tccttaatac aagatacagc 16740

```
catatcttgt aatgatttag gtgtgtcatt atctaaaatg ttgaagttaa aagatacagc  16800
ccagtcagtg cagaccgtaa cctttttaat ataattatct tcaacctcta gcggttcaaa  16860
ccaatattca ataatttctt tatgcccaat atcatctttt acttcgcatt caaaatgctg  16920
actcatcata acatttttaa attcatcaaa agtcattgtg ttgcctctac atataactga  16980
tttgcatatt gaataagtgc ttcgcgatca gaatcagtga tgtctggaat tgcattaatg  17040
tattcttcca tcaacgtctg aagagattga acttccactt cttcgttatc atctgactcg  17100
acagagttat caatctttga cacaactcgt aatgaatgca caactttttc tagttcagat  17160
tcgaacttcg ttagattttt gtctacttca gttactataa cacgtactga tagatttgta  17220
aaatctttat agtcaatttt tcccttaaat ggatattgaa ttcgacgatg ccaggtggtg  17280
ttgtttggaa taaattccat tcgttctgtt tctgtatcaa acatccagaa cccacgaggg  17340
tcattctcgt cacctgcagt tagtgtccat ggtgtcccaa tatatctgac gttagcagcc  17400
tcagagatag tatggaagtg accagaccac acctctttat aagtcttaag gaaatcaggt  17460
tcaagaccgt gagatttcat tcctttataa aaataaaatc cattcagttc ccagtgacca  17520
acacaaaaag aagcagatga agttttaata tgttcaagaa tttcaccagt attttcttca  17580
cacatccaag gaattaaatc aatcaaacat ccgtcaaaat ctactgtagt aggcttatca  17640
tatactttaa cattaggata tttagccaaa agctcagtag aagcatttgg agttaaagta  17700
tttttaaagt gcatatcatg gtttcctaca acagtatgta gggtaatacc agcatcatca  17760
agcatttgaa ctatttcacg agcgaactcc atagttttat gcgtgatcgc ttttcgcaca  17820
tcaaaaatat cgccgtattg aatccataca gtaattccat ttttcttaga atattctatt  17880
gcttgtttaa ttccatccag ctgaatagat tgaacccact catcatcggc tttaacacct  17940
aaatgccaat cacctaaatt taaaattttc atatatcaag aaccgtcatt gaaatgcaaa  18000
ataaaattat tgaaataaat ccatctggag tgctaaagaa cccaatccaa catgctctag  18060
tgaatagata aaacgcgaga aaaagtatca catatccaag aaatatcatt atatcaaact  18120
ccgtataaag ctaaagggcc gaagcccttt attttgtaat aatgtcaaac tgttctttaa  18180
agcagaagct tgaatcttga tgctgataca aaaattcata agctttttcg cgttcacggt  18240
cataaagagc tcggtcagat gacagttctt taatacgctc aaatgttgat tccatgtcat  18300
tttcatcaaa ccaaacgata ccgctatcgt gtgaaattag cggagtatta tcaacacgga  18360
attttaaatt ttcaccagta gatttccaaa atactggaat tgttccgcac gcgccaagct  18420
cgagatgagt atattctaaa gaacgttgta gatatttttt gtccaactta ctcaactgat  18480
aaccaaatcc ggatttactc atgcgttcaa gcatttcgct atttacataa cggtcaagaa  18540
tttgcgttgg caaattagga gcaattttaa tttggtctac ttgatgaaga cgataatact  18600
cgtatggaat tcctttttct ttaataggaa tgaacgcagg agaacgttcc agaccttcca  18660
taatagtact tagcccagca ggtttaagat gtttttcgtg aaaatcaaac atctgataaa  18720
aacctttcca tgtagtcgta cgaccaatcc aacggttgac attcatgtta atttcagaaa  18780
catctttcca gtaggttgat cgaactttcg caatatccat aggaggctga aagttgtata  18840
cggtcggtgc ttcttcaata tcatcaaaca gtgaaacagt ttctggatac cattctttca  18900
tcagaacttt attaaaatcg ccattatcag aatgactaaa aataacatca gctcgacgaa  18960
cagtttcttc taatcccaaa tttcggcgca aagaaagaga agaatggtca tgttgataaa  19020
ctacaacacg aactgaaggt ttaatgttat caataatttt tttatagtta ttaatagtgt  19080
```

cttcttcgac tgaagtagca ggaactgaat tgataattag aatatcacaa tcatttacca 19140
gcttaagcgt tttatcgtat tcttttgcca ataaaactgg aattgaaaat gacttataat 19200
catgcgcgca attacgagta aatgatttat ctttagcata aaccaaagtt acttcatgac 19260
catttttaat aaaccaatca cgttgctcaa gagaaaattt agttacgcca caaccttcaa 19320
gacctcgagc cataaaaatg catactttca tttaatatcc tcattgtttt ggtttatttt 19380
accaaaaatt tataaagcaa tataggagcc gaagctccta tccgcataat acaccataca 19440
gaggctcatt agagcttcta aattttatac gtttatgtgt tatagttcct tctgctttag 19500
ctttatcatg agactcttta aagcgcctca tcatttctac tttagaggaa cgaattttat 19560
tataatctat ttcacaagtc tgggcgttca tctttcacag ttgccaccat tttttgactt 19620
gataggaatc aacccacact ttcatattag ggtctgctct tacaatagga ggattaactt 19680
ctttaattga actatcgtgg tattcttttt cagaaatttt cacgcaaaga tgaccattca 19740
aagattcagt aaatcctgca ttaattttaa gacgcttgaa ttttacgtgt gtaagcatca 19800
atcatatcct caatctgtga tctagtagtc ttccaaagaa tactaatgag ttcatcgtta 19860
tatggctgtt ttagaatatc ccgacttttc ttgatagcat attcgtattg agcaaaatta 19920
ttgttttcag ctgcaatctg agcgtgctta taaagacggt tcagttcgcg tttattttta 19980
gacaataact tatttgcttt tctttctgct tcaagacggt tcttttcttc aatagaagaa 20040
ataagctttt ccacttcatc attaatttcg ggtttatcag tcatattatt tctctaatat 20100
aaaataaaaa tcatcatctg ttaaatgata ccgatagttt aattctacac cattagattt 20160
aaaagcggta tcatacggat tttctggatc aatatcaatg tcaagagcta aaacttccct 20220
gagatacatt ttaagtaaat agggaatagc ttcaacttca ggtatttctt ccaagaatcc 20280
ggagaggtta atcgttagcc tcatataaaa aatccaaact aggagaatcg tctacaacac 20340
ttttcttttc agcccccggt gttctatagg ttgattcttc gtaatgcgtc attttatcgt 20400
agatgtcttg aataaaagtt tcatctacta acgcaaccat atcgtcgtca cgactgtcat 20460
agacattgtg aacgaagtaa ctgtatttct ttgcaacttc cttacgttct tttttaatac 20520
gttggacgaa tgcattaaaa caagcttgag ttatatatgc atgtgggttt ttatatttcg 20580
tttcatcaaa attgtgaagc cctttaatag aagcttctat accgtctgca atcatttctt 20640
gtttccagga ttgggtgtat cctgaaaagt tgaaacgttt agataagcct tctgcaataa 20700
gcataatggc taatccgata gtatcattct ggcgaactac tttatttggg tctttattat 20760
ttgctaattc tgttttccaa tcaataatag cttgtaaaag ctctttattg tttacgtaat 20820
tatatttagg cttagtttct gacattttca cctcttagct caattcatag atctattata 20880
ttataatatt tgaagatcta tcttaaagca tagaggatat cagttatcta agtaagcagt 20940
atgcttggaa cactttctcc atcatctttt taaattcatg aatatctatg taatgatcat 21000
taatatcagc gcgatataaa aagtctaaaa actttttatg ggtattagaa tatttacttc 21060
cagttaattc agaaacatgg ctttcccaat atccaacacc agttttattt gggaaaaatg 21120
aaattttcat gtattggtca acatagaaaa taccaaaatt ttcaatagca atagaaatat 21180
taattaattt catacattca tcaacttagc cgcttcaaga gctgcatcta gtgaatcaaa 21240
ctggtcaacg tattcaatca attcgccata attggcatat aaccaccatt ggctaaattc 21300
atactcaagg atgaatccat ttccttcaat ttgagttaaa ccaatgccgt ttgtatttac 21360
ttcatatccg gcaagacgca aatcgttaat aagagcttcg ttcataatta tgccttagta 21420
attttcaggt cagcaaattt tttcttgcgt tgatttttca tacgacgaat agttttatcg 21480

```
gaaatttcat gtttttgata agatttagat tctacaccaa aagctttaac atcaaattct  21540
gacaagatat attgaaccaa caattcacgg acagtattgc gtccaatctt ctgatcattc  21600
tgtttcatca tctgatgaag ctctttttcc catttatcca aaatttgagg agttacaata  21660
tcgccttttt ctagcaaaga aactacttta tcatatgcgt aagaattaat gacgttttta  21720
atttgaatag tcatacatta tcctcaattg cgttaaaatt ttattatcca aaaagggccg  21780
aagcccttag ctaaactgtt tggcgccctt ccagccttcg tacatcattg cggctgatat  21840
taatattgct cctgagcaac ttgaatattt gtgattccaa aaccagttta gaaaaacttc  21900
gtcatcaata ccttgggcta tcatattttc aaagaactga cgacgagctt cagcaattcg  21960
ttgcgataat ttagattcag gattcattta aattttccag ttaccatttt catcaataaa  22020
tttaatccag tcatttactg accacttggt cgtatcgccc tttggagcaa catttaaagt  22080
gtataatcct tgtttaaaaa gcattcgttt gatattcata ttttcctcag ctgtaacgat  22140
agcactcgtt tgatttacgc ttagcaactc gttgagaagt attataatca aaatcatcgt  22200
caatgtaaac tgatttttc aactttctta cttcaccacg taattggcga tttagctcat  22260
ctttaacttc tgaatcaatg cctttcattc tacgccattt atcagagcga aaaatgtttt  22320
cgaccatatc tttatgactt acaccatcag gagctttacg ctttccgaaa tagtcataat  22380
cacgaacttt caagtcttta cgacgatacg ttttacccat ggagtttaat ttccttagca  22440
actgaactaa atacagcacg gtcacaaatc atgtgtttat gtaacttaag tataagataa  22500
taaacttcaa aaccgtttac ataagtaaca cgaacaacat taccattaat aaaataatat  22560
tgtccctttt taatttcttt atcaaccaca accatatcaa atcctcaaag gcaattcatg  22620
tgttaataat accacagttt gaacttcttg taaacaactt tgtgaaaatt attttaggga  22680
atgataagaa gggaacgata gcttagaatg gtaatataca gaatgtgaga aagaaaggcc  22740
cagagggccc gtcttagtct tctatgatat ctctatcata tccaagtgaa atgagagttt  22800
ctttgaagtg tttaatgttc ttttgtctag aatcattaat gaaaatgact ggataacgaa  22860
tgttaagaga tgtaaatcca gcgcgtttag caagagatac aatcagtgga cgatcatact  22920
cgatcttacc attatttgta ataactttat agaaagtaaa aggagcattg agctccttta  22980
gaagttttgt aactgattga catccaggac aacgaccaac ttcatctgga attccataga  23040
cttcaatctt attctttaag ttcgagtttt gttccacgag aaataattcc ttgataagcc  23100
caatatggcg ggttaacaga atcatcgcca gaattttctt caggaaaata aacctggata  23160
acaaatccag attcatcaaa ggtaaaataa accgtaggta attcacctaa caattcagca  23220
cgattattaa tttcttcgag ttctcgttca cgtccggccc aaaaactagg atttagacta  23280
cattcataga aataatagtc attaccgaac atatcaaaac cattccaact ctctaccaca  23340
taccgctcaa aactaatcat aattaagcct ttttatcaag aacagaattc agtttgttag  23400
taattttatc cagacgctca ttgaactcgc tagaagacag tcctttttct ggagaaatta  23460
agctaatcac gaaaaatata gcaataaaag gaataagaaa aatagctcca actgccataa  23520
acaaaaagaa tgttacggtt gtaagaaaat cagctaaacc tttacgaaat ttatacatat  23580
ttacccttaa ttgattaacc aagcattgat aagcactaaa ctatattgcg aataaaattc  23640
tggaccaaaa tgaaaaatca tatcatttat agtgtccata atataattca atttaatcat  23700
gtttccacac cccatcggta tttgaccaaa gtcgctgatt atctgatcct cgccacagct  23760
ttttggtcgg aagatttttc tcatacttcc catcaataat aacatcaaca tatttaagca  23820
```

-continued

```
tttctagttg tttaatatct tcaaacttat atcctgtcca caaccaaatg cttttattgg  23880
gataaagatt ttttactgtt tgaacaatgc aatgaataac atctcggtta tcaggataga  23940
gagggtctcc tccagttata gttaatcctt ctatataatc attattcaaa cattcaatta  24000
attgttctag tgtttcacca gtgaatggaa caccatttct agcattccat gttgatttat  24060
tataacaccc ttcacattta tgcaaacaac ctgtaacgaa aagaacgacc ctgcatccag  24120
ggccattcac aaaatcacag ggataaaatc tatcataatt cattggtgtt taaccctatg  24180
catgatttct ttatttttgc ctagattaaa tccgcgttca ttcggatttc ccaaataacc  24240
acaagttctt cttattgtgt tcatcttttt aggatcagtt tctccacaaa tagaacaaac  24300
aaatccgttt tcagtaggag tcatttcatg agtgcttcca cacgtaaaac atttatctac  24360
tggcatgtta acaccaaaat aatctaaatg ttgtgcagca taatcccata cagcctcaag  24420
accttttagg ttatttttca tatcaggaag ttcaacataa gaaatgtgac cgcctgttgc  24480
aatgaaatga tatggggctt ctcgagaaat cttttcaaac ggagtgatat tttcttctac  24540
tgaaacgtgg aaactattag tgtaccatcc tttatcagta acatccttta cacttccata  24600
tttctcagta tcaagtttac agaagcgata gcacaggttt tcagcaggag tagaatataa  24660
gctaaaagca aaaccggttc tttcagtcca ctgcttaaga cgagcattca ttttagtcaa  24720
aatttcctgt ccaatatcac gaccgacaag aatattcaat tcgtgaatac caatgtatcc  24780
tagggacact gaacttctac cgtttttaaa taactcaatt atgtcatcat caggtttaag  24840
acgaaccccg aatgcacctt cttggtaaag aataggagca acagtcgctt taactccttt  24900
taaggaacta attctacaca tcaaagcttc aaaacataaa tccattcgct cattgaataa  24960
ttcagtaaat ttctgttcat tgaattgtgt tccaatataa gaatctaacg caatgcgagg  25020
aagattcagt gttacaacgc caagattatt acgtccatca agaatttcat taccagtcga  25080
atctttccat acactcaaga aactacgaca acccatcgga gaaacaggaa tagatgaacc  25140
agtgatagct ttattgttct tagctgaaat aatatcagga tacattcttt tgcttgcgca  25200
ctctagagca agctgcttaa tatcatagtt cggatcgtct ttataaagat taacaccttc  25260
ttcaacgaac ataacaagct tagggaaaat aggagttatc ccatcacgac caagaccttt  25320
aatacgattt ttcagaattg ctttctgaat cattcgttca gtccagtcag ttcccgtacc  25380
aaatgtaatt gttacaaaag gagtttgtcc gtttgaactg aaaagtgtat ttacttcatc  25440
attatattca gcatgagtcg caaattcatg cccgtttata tgaaacaaca aaatttggat  25500
agtccataga tatgcaacgt tcttttatag tgctaggatg aaaatttagc gctttagctg  25560
cttctatata agacgtatac ttaataccgt caacaaccac atattcagga actttatgaa  25620
tagtagtctt aatactcaaa acaagaggat gagtttcgac ttcactttca gtgcaattta  25680
aatattccgc tgctttttta aaacttctaa aagttttatt tttaagcttt atcgatactt  25740
gtttttttact ttttcgacta ttgatattat tttgcacatg ttccttagat cttccgtttt  25800
tagcataata ttcagctaca gaagatttta tattgttttt atgatattcg gataacactt  25860
taccccttatg agcatctctt aatttttgaa tatgttcttc agtatccgga tgcttataaa  25920
actttttacc gcctatggat ttatttaaac attttttgct ataaaaatat ttacgtatga  25980
cctcttcttc atgttttaat gcatctttat aactatcaaa tgtttttaaa attatccatt  26040
tagtaggtgt atcagttttt aagcgttcat ttatatactt agatgacgtt gtgtaagttt  26100
tccagtttgt gggcttgttt ttaattgttc taaatttttt ataaccgata taaatgtcgc  26160
cattagaaaa cttaactaag tatgtaaatg cgtctttatc ttttatttta gtacaacgtc  26220
```

```
tttttatcca tttcattgtt tcacctcgta ttcataagat aatcttattt atacaagatg  26280
actgctgcat gtcgccatgc agattagact atatcttcat ctttcgatgc cggccgtttc  26340
gaatagcatt agcttctatt ctacaccgct acattcatca cggttagtcg ttaggcattt  26400
agttcaaaag aacatttagc acgggattgt ctactagaga ggttccccgt ttagaccggt  26460
tttacatgag cctgaattaa attaactcat acgcttggaa tgcatcgtat acatcttttt  26520
ctgttttgga ttgagcataa ttcaacgcat cagcgatttg ccatttttct gcatcctcaa  26580
tatgttttgc ataggtgcgt ttaacataag gagaaagtac tttatctaca ttcgcaaaag  26640
tcgttccgcc atattggtgg gaagcaacct gtgcagtaat ttgcgccata attgcagtag  26700
caacaccgat tgatttagga gtttcaatct gtgcattacc gagcttaaat ccgttctcaa  26760
gcattccttt taaatctact aaacaacaat tagtaaaagg caatgatata ctgtaatcta  26820
aatcatgaaa atgaattaat ccaacattat gggcatttac aatatgactt ggaagaatac  26880
gacaagcgat atgtttagaa acaataccgg ccattaaatc tctttttgtt ggaaagacgc  26940
gagaatcttt gttggcgttt tctgtattta attctttatc tttatttgaa ataaaattta  27000
aaacatcttt ttctaaagac ataattctaa tttatccttt tgaaattctt cgtctaaata  27060
tgggttccaa cccatttaa accttttgat gaaattatca attctaaatt tcggtaagtt  27120
taaatccgca aaaatagatg atttactttt aaaatctgga cctaaataat catataaaat  27180
ttctgcgtat tttaaccata atatacaagt accagattta attgcgttcg gagttttcca  27240
aggttttaca ccatacatcg gatttccact tcctttatgc ctgatagaag atgaaattcc  27300
aattttaatt ttagcttcct ttgtatgcga aaatccacga tgcggatttt ctttccagta  27360
tttttagaa gcttctgata ttttctttct ggctaaatta gtatgatgct ttccataaaa  27420
tccatgattt ttgcctttat tacaatttct tttaatcatg gttattgatt gcttttctct  27480
agtttcttta gaaggagaaa taccatatgt cgtaaatttg ccatcagcat atgctaaatt  27540
aaaatactct ttattccata catctttttc tatattcttt tgaaattcag cttcaatgct  27600
agttatttgt tcatctccga ctaattgaaa atataatatt tcaactttcg gcgtttcttt  27660
caataaggct ttttgaaatt cggaagatga cgaagacgaa taataaaatt taccattttt  27720
atcaataata ttcgttccgt caaaagtgca attggtttta cttccaatgt aataatatgg  27780
tggggtttta gcattaattc tattaataaa tgatagttta tatactacat tcattttaaa  27840
ctctttctaa gctgcttctt aaatgaagct attaattgtg ttttagtgtc agattcatta  27900
tattcaaatc ctctttgaag catctcagcc atcatttcct cttttcctaa acgagaaaat  27960
tcctttgatt tatctccaac gaagttaggg tgaatattat tttgggtgta atcggatttt  28020
aaataagtaa gtaaattttc tagccattca agataatcaa caccttgtcc ttttaagcca  28080
gaacgattaa atttatgttt catttgacct tctgcagcat tgcagagatt acagagcaat  28140
ccacgtacct ttccagcttt cggtccattt aattcatggt catggtcaag atgattagct  28200
tgaacatcag gatttaattc tcgttggcaa attaagcatt taccgttttg tgcattataa  28260
aatttttgtt tttcttcttt gtataatttg ccagtcaata acataataaa acccttacct  28320
tgaatagata agggtattta ttattttcaa gtattaaaat gctcggtcag aaaaagaaat  28380
ttgagtttca agccattcaa tatattctgc cgcagcttgc atcaaatttc cttcataacc  28440
atcgttattt tcttgtgcag ctaatttagc taatgcatat gaaatgcgtt caccttgaaa  28500
agcggcttta ggtttatgaa tagcttgatc aactcgttct acaacttctt caatttcgcc  28560
```

-continued

```
attttctact gattcagtat tccataagca ccaataggca gttggcttat cgtagatgtt  28620

aataatcttt ccatcagaaa gttcaatttc aataattcca atatcaggtt ctatatcatc  28680

ttcacattct tttacaagtt cacgaacttt aaatacagta cctgcgctaa gttccggcca  28740

gtaattacac agctctttat cagcacgatt aattctaaac cacttatcta ctgtaatcat  28800

gtcccatctc catatcaatt atgtcattta ttataggttc attatatact gtttcttcat  28860

cagtgtaaac cggttcttcc ggctctggct ctacagtttc ccatctaacc gcccaccagg  28920

gtttaactcc gaagcttatt aagttcttca taatcaatcc aggattctag tcctgatggc  28980

aaatcagatt caatttccca aagaagttct tcaattttat gaagacgatc taattcttca  29040

gcaggaatag taaccattga cggagctctt gctacattaa tatcgtaaat catatttacc  29100

ccagtttgac catacaatcg ccatatttcc atttagaaat agacttttca ccgttagaat  29160

aataaacttc gagtttagca cggttatttt taatttgaat aaccttggct gtcatcaaag  29220

ttccata                                                            29227
```

<210> SEQ ID NO 2
<211> LENGTH: 545
<212> TYPE: DNA
<213> ORGANISM: Artificial Sequence
<220> FEATURE:
<223> OTHER INFORMATION: partial sequences of Bacteriophage EK88P-1

<400> SEQUENCE: 2

```
tattctggta gaaaatacac gccttcaatt ccagatgcca gtaaacttcc taccgacaca     60

attaaaatga ttgatcgcat actagaccaa tctaacagca tttataaaga aatgcctcca    120

gccattcaaa gcacgataga tgatattact gggatgtttt accagagtaa gtatcttctt    180

tccctcgaat aacattagtc tccttcggga gactttttc attttaccgg tttacttttc     240

gtttgagccg tggtactata caaccatcgg ataaagagga gaacatcatg aaaattgaag    300

cacttaatca agaaggaaat atctacgtca tcattaatgg tgattttttc gtcgacatgg    360

atgaagttac tagtgaagaa cttgtagaac ttcttaagaa acgttataat atgtgtgatg    420

aagttgcaac tcacatggcg tgtgcaatat tctctctttc atatgtggtg gaataatgat    480

tagtatcgaa caagcggata agattaaaga attggtagct ttaattcgta aagcagatga    540

ggaac                                                                545
```

<210> SEQ ID NO 3
<211> LENGTH: 4686
<212> TYPE: DNA
<213> ORGANISM: Artificial Sequence
<220> FEATURE:
<223> OTHER INFORMATION: partial sequences of Bacteriophage EK88P-1

<400> SEQUENCE: 3

```
gaacttgaag ctaaagttga taatgcttta gaagcgttag atatgtttct tgatgaaatt     60

atcgatcata atacgagagt ttaagtatgc taacacgtga acagtttgaa aaaatcatta    120

aattagcacg tgatattgaa atagattcat atcaattagc agttgagcat tgtgaaggat    180

attcatacga cggtatagaa gcagctaaaa aggatttgga taaatccaaa gctaagttag    240

ttcaatacct tgaaatgatt aggtggaata atgaaaactg aaaagcagat gtttttaatg    300

aaactaattg aagaatatgc taatgcagtt tctgaatatg agtattctgc tcgggaaaga    360

ggtacagctt tcgcaaaaga agaaatgaaa atcatggttg atgctcacac aaagcttcag    420

aattttattg aaaacgtcat ttaatggttt acaagttggc aaggttatgg tatagtaatc    480
```

```
ttgtcaactg tcaaggagaa gagaatgaaa attttgtttg ttgtgtatgt gatgattcaa    540
tataattacc caatgtttac ttataatctg gtgaacaaca ttattgatat tgaaacgatt    600
agtattagaa gttagttcac tttttggtga attggctata gaaaaagtaa ataatatgta    660
tcgtttgacg caagaagacg atatgctata ttttacgcct agcgaaatta ttcatttaac    720
ccaaattgaa aaaccttaca ctgataaaat tgtaagcatt aatgatgagc ataaaattca    780
tttctattct ttatgcccag gatttaatat tgaaagcgag tcaatatgct tatcaattaa    840
taattgggat aatttttataa cttacattaa atatttttat tattctaatg aaagaaaaca    900
tagtttaaaa tggcttaaaa attgcaatgc tattattact aacgcttgcg atcagaatga    960
tgaaattgtt ttaaatgtat caaaatgcta tgaagaagga gatgtcttaa ctattcgtca   1020
aattgatgat tctcgagcgc atattgtcac atttaccaaa gacgaagcta ttgcgttaaa   1080
gacttatctc gattctgtta ttccaactat gatttcaaag tgaggaaata tgtttatttc   1140
aagtggaaca gacatgtgtt ataaatgcaa agcaaaatta aatgagacga agaaccaatg   1200
aattatacta aagtatataa taatttaatt aagaaaggaa aactcagaaa attagataaa   1260
tctaaattaa atttttatac ggaaaagcat catattattc catcttgtat tggtggtaat   1320
gatgattctg ataatctagt tttattaaca gctagagagc attttatagc ccattggctt   1380
ttagctaaaa ttcattataa ttcgcctgga ttaatttatg catggtggtc attttataat   1440
tttggagaag attctttagg aagaaatctc aaattaactt caagaggata tcagttagtt   1500
agagaaaaat tttcaaaaat acattctaat acaatgaaag aaatgtggaa gtctaatgaa   1560
tacagagaaa aacgttcgat aacattaagt cttcctgaaa taagggctaa aatttcagaa   1620
tcccagttag aagcacaaaa caaaccggaa gttaaagaaa aaatatctaa aggggtgaaa   1680
gctgctttta aacgaccggg agttaaagaa aaacactctg ctgcagtcaa aaaatctttg   1740
aataattttg aaactaaaaa gaaacaatca aattcatcta aaattagaca aagaactggt   1800
aaacattggc aagactatga cttactttat aagttatgga ttaaattaaa tagacctaaa   1860
cgtgggtcat tcggaactta tataagtaaa ttaggatatc caaaatctaa ttatcatcga   1920
ttgattgtac aatttaatga agattatgaa aggtctaata atgaaaactg tagttaagtc   1980
ttattttggt agtcatcttt atggaacttc tactccagaa tctgatgtag attttaaaga   2040
aatctttgtt cctcctgctc gcgacattct tatcggaaat gttaaagagc atatgagtaa   2100
aaacactaac aacacatcat ctaaaaacac taaagatgat attgaccatg aactatatag   2160
tcttaaatat ttctttaaat tagcagcaga tggtgaaact gtggcattgg atatgctcca   2220
tactccacct gaactggtag ttaaatctga tttacctgat gtatggaaat ttatccaaga   2280
caatcgttca cggttttata caactaacat gaaatcctat ttaggatatg tccgcaagca   2340
agcttctaaa tacggtgtca agggttctcg tttggccgca ttacgtgatg tattgaaagt   2400
agttaatcaa atccctgacc agtgggttga ttaccaagaa gacggttcca ttaagcagcg   2460
tcgcactaaa gttgaagata ttaagcatcg tcttccagaa aacgaattct gtgaatgggt   2520
gttccataat catgagaaaa caggcccgca aacgttctac actgtgttgg gtcgtaaata   2580
tcagacaacg ctttctctta ttgagcttaa gcagtcactg aacaaattag atgctgaata   2640
cggtgaacgc gctcgtaagg ccgaagccaa tgaaggtatt gactggaaag ctctgagcca   2700
tgcttgtcgc ggtggactcc aactattgga aatttacaaa actggtgact tggtttatcc   2760
acttcaagac gctccattta ttctcgacgt gaagttgggt aaacatccat ttaaaacagt   2820
```

-continued

```
tcaagagttt ttggaagatg tggtcgatca agtagaagca gcatctactg aagcttctaa   2880

gaacggtatg cctaaaacag tagacatgag tttctgggat gacttccttg agaaggtcta   2940

tcttgaaaac caccgaagtt attataaatg atagggagcc ttcgggctcc ctttttttatt  3000

tcaaaaattt tttcacaaaa ctgtttacaa gcataaagct ttatggtact atacaactat   3060

caactgatac ggatttgggg aataaaatga aaactacgtt aattgaagta aaaaagttga   3120

ttgacacaga agaaatttca gcttattttg aaaatttctt agaagatgca actgaagata   3180

acgcagttta tctcgctcag aaaattatag aaacatattt ggagcagaat caatgacagt   3240

ttacgtagat gttttaatga atcatggatg gaaacttcgc ggtcatccaa ctaaaaattg   3300

tcatatgttc actgatggag atattgaaga gcttcataaa atggcagaag caataggaat   3360

gaaacgttct tggtttcaag ataaacgcat taaacattat gacttacatg ctcggcgacg   3420

ccaaaaagcc gtagaacttg gagctgtaga agtatctcgt cgcgaagcag taaaaatttg   3480

gcaaacatta aaataaattg tttacagtag ggtagtagtg tgatactatt accctatcaa   3540

aacaaatgtg aaattggaga ataaaatgaa aactgtaact atcaataagg gtatctactt   3600

tggtaaagaa atctctggaa cttttgagct cttaggtgaa tggttccctg ataatgctcc   3660

ggtagatgca caaggagatg gcaaagtttt tgttgaaatt gacggtaaac gtcgtggtgt   3720

ttgggtttac aaatcagaca tttcatatga tggtgtaaaa gttgaagaag ttaaagaatc   3780

gtatgaagat atgaaaaccc gcattaataa aagatttaat gttatgggaa tgatgacgaa   3840

tggtattatt aacggaaaca ttcgttcatt aattatctct ggtgcggcgg gtattggtaa   3900

aacgtattct ttagataaag ctttgaataa agcaaatgat aatggataca ttgaatataa   3960

aagcattaac ggtaaaatct ctggtatcgg tctttatgaa cagctctgga ataatcgtga   4020

agagaattct gtccttttga ttgatgatgt ggatgttttc tctgatatgg acattcttaa   4080

tcttctgaaa gctgctctgg acactggaga gacccgtaaa gtctgctgga gcactgcatc   4140

ttcttactta gaagaaaaag gcattgagcg tgagtttgaa tttaaaggaa cgattgtttt   4200

tatcacaaac gttgacattg accgtgaatt agaccgtggt actaaacttg ctccacattt   4260

acaagcatta gtgtcccgct cagtttattt ggatttgggt gttcacgcta atgaagaaat   4320

tatggtaagg gttgaagatg ttattctttc aaccgacatg atgcaaaagc gcggtctttc   4380

tgatgaagaa acttataaag cattatcatg gatgaaagtc aatgttaacc gtttacgcaa   4440

tgtttcactg cgtactgcac tttatcttgc tgactttatt atgactgaca aaaacggttg   4500

gcaagaaatc gctgaggtta ctcttctgaa ataaattcat aagaggcctt ctaagacaaa   4560

aaggcagttc agaaatagat tatatggact gccattaaaa agatgactag aattaaactg   4620

gtaaatggag gtaatgatgt tatactcaaa ggctcgtgaa atttacgaaa ctaaaattaa   4680

agaagc                                                              4686
```

<210> SEQ ID NO 4
<211> LENGTH: 2468
<212> TYPE: DNA
<213> ORGANISM: Artificial Sequence
<220> FEATURE:
<223> OTHER INFORMATION: partial sequences of Bacteriophage EK88P-1

<400> SEQUENCE: 4

```
aaagcctatc ccaaaatttt agaaatagat aaaaccacta ccgagtacgg ttctcgtgat     60

aaattaggcg atatgtctat tgtttttaaa cacagtccta caggatttgg tatatgctat    120

aacctttata cgcaatacga accgggtcct aatcttgatt atggtgcttt agtaaactgc    180
```

```
atgatagaat taaatctaca ggcagaaacc cttttgttta aaccagtaat ttatattcca    240
cgcataggtt gcggtattgc tggcggtgat tgggataagg tttctaaatt aatcgacatg    300
tttactcctg atattgattt aatagtggtg gattatgaaa gcacattacc cgcatccgtt    360
tgaccctaaa aacaaagcag aaattattcg tcaatgggaa cgcatttgtc gtactaaatg    420
cccaattaat agtccgcatg atgtagataa agactacatt ggaacattcg ttgaatatac    480
ctttattgat aagaaaggtc gtaaacaaca cgtagaagaa tattgcttaa aggttacatg    540
gttatgagcc aaactagtat tcttaaaaat gcccattgtg aaaagtgtaa atggcctgtt    600
gtttttgctt tatgtaatga tgaaatggcc tgtgatttcg actattggtg ctattgttct    660
aataaaggat gcatcaatca taaaggtgaa ggattttatt caggatttta tccttatcct    720
gatttcgtta aagaaggtaa accaaaatga atgatgattt aaaatatcaa ttattacgtg    780
aacttgatgt tttgattgaa ctttctgcac aaaaaggatt tataattgga tcgggtcaaa    840
aagaccccaa cggtcattca atcgtagcgg ttatgaatca gaaacgagtc attttaaaac    900
ttttggggat tgacatactg tgagcctaag caaagaacaa aaagataaat tgtttgagct    960
tatccatgaa cttctagatg agcatacaga agcaaacacc ttttatgatg aatacggccc   1020
gctatctccc gaacagcaag aagaatttgc tgaccggttt gataagaaag aaaacgaatt   1080
aatagcttat gtgaatacgc tttaagaagg tgatatggcg agtttaattt ttacttatgc   1140
agcaatgaat gctggaaaat ctgcttctct tttgactgct gcgcataatt ataaagaacg   1200
tggaatgagt gtattagttc ttaagcctgc tattgatact cgcgattctg tctgtgaagt   1260
cgtttctcgc attggaatta aacaggaagc gaatattatt acggatgata tggatatttt   1320
tgagttctat aaatgggctg aagcacaaaa agatattcat tgtgtatttg tagatgaagc   1380
ccagtttta aaaactgaac aggtgcatca attaagccga attgtcgata catataatgt   1440
tcctgttatg gcttatggtc taaggactga tttcgctgga aaattatttg aaggttctaa   1500
agaacttttg gcgattgcag ataaacttat tgaactaaaa gcagtttgtc attgtggtaa   1560
aaaagcgatt atgacagctc gattaatgga agatggaaca ccagttaaag aaggtaatca   1620
aatctgtatt ggtgatgaaa tttatgtttc tttgtgtaga aaacattgga atgaattaac   1680
taaaaagctt ggttagtaca aaagttataa ataggtttat ctaactaaag gggtatatat   1740
gctacaatta actgaaaagc aacttcgcaa tcttactgtt cttcaattag atgaaattcg   1800
tagggaagtt ggaaatatca tttcagcttt gcgtcgagaa gtatcgctca accaatctcc   1860
ggcagactat actagattgc gaaattttga aaaatacctt gataaagtta aggccgtgca   1920
tcggcataaa gtaaatacag gacaaaaatg ataggaggcc tttatggcct taaaagcaac   1980
ggcactattt gccatgctag gattagcgtt tgctttatct ccaccgattg aagcgaatgt   2040
cgatcctcat tttgataaat ttatggaatc tggtattaga catgtttata tgctttttga   2100
aaataaaagc gtagaatcat ctgaacagtt ctatagtttt atgcgaacga cctataaaaa   2160
tgacccgtgc tcttctgatt ttgaatgtat agaacgaggc gcggagatgg cacaatcata   2220
cgctagaatt atgaacatta aattggagac tgaatgaaat tcagcgactt ttcacaaagt   2280
ggaaaacctt caaaggcaga tgaatactta ggtttattaa tggctgcaca agcttatttt   2340
cattctgcac attttgaaac taaaagttat gctagacaca aagcatacga ttttattttc   2400
tccgagttgc cagatttgat tgataaattt ggtgagcaat atttggggta ttctggtaga   2460
aaatacac                                                            2468
```

<210> SEQ ID NO 5
<211> LENGTH: 13192
<212> TYPE: DNA
<213> ORGANISM: Artificial Sequence
<220> FEATURE:
<223> OTHER INFORMATION: partial sequences of Bacteriophage EK88P-1

<400> SEQUENCE: 5
aggctttcag cataattctt tgcgaattcg cagtcttcac aattatctaa tgcttcccag 60
aattcatcat ataaagcatc aaagataagt cctaaacgaa cttcagcgtc tttgatagca 120
ttcactttac cgattttctc ttcagtgtgc ggcttataac ctttaatatc ttcaatcata 180
ttttacttcc tcaccagtac ataaatcata ttcaactaaa cgaataggtt catgaatgcc 240
atatccttga acagaaattt ctgtcgtagg ataaattcca ctaatatcac ccatgttcca 300
cgcttcatta aattgctgtt cgcctgaatt actaaaccat tcggcgaaag catttagcac 360
atctttagaa ccttcaataa ttatctttgc cattacagac tctcagtaaa ggtacgagcg 420
ataacgtcgc gctgctgttc cggagtcaga gagttaaagc gaactgcata accggataca 480
cggatggtta gctgcggata tttttccgga tgcttaactg catcttccag agtttcacga 540
cgcagaacgt taacgttcag gtgttgacca ccttcaattt taactgtagg ttgtgtttca 600
atttcaattt cacgggcatg caaaccatag aaaatttctg ggtctacaaa agagtcctct 660
ttaaaggttt tagaaacaat aattcgcgct tgaataccat cttcaaaata aatagtacct 720
ttatgtgtgc cttcaagaat ttgatatgct ttcatataaa cctcaattag aaaataaatt 780
tatccaagat tgttctttaa ttaaaaatgg ctcagaatca tatgccatta aactctgtgt 840
gattagtcct ttaaaaggcc catcaataaa ttccatagta aaatatggaa ttttattcat 900
tagccgtgca ttaggagccg tgcacaaaac tctgcatcct ttgaatacgc ctttttgtaa 960
tttgtattgc ttaggataaa attcgctcaa aatgttattt tttgctaaaa tttcaaaatg 1020
attcaccaat ttatttttaa tagtttttgg cgaaaaatag agatattcga aaagctgagt 1080
gtctgtcatc attgcattcc gattacgaaa aactgcggac gagtaatacc accaatgcaa 1140
catttactat tacagcagta gtgtacagtg tcaatatgga cactataaat cttatccata 1200
tcaggagatt tgacaggctc atcaattata tacaaaattc gcgaaagcga taaacctctg 1260
aacttgcttc ctttattacc gataaaacta cggacagaat cagtaaataa acgaaaacgt 1320
atatcatcat tagaataacg cgaaaattcc tttttaatgt tatttgcaga aattttagcg 1380
taagctgaag tattagaaag aacaataact gttccaccgt catacaacca attagcggca 1440
aaattagtta ctgcagttga tttaccggat tgacgtccac catctagtcg aagtgtgcaa 1500
tactgcttaa gtaagtcttc aaatggcggg atataatcgt ttttacaaat ttcttctact 1560
ctagcatcag aatggtgtgt aaaagcattc atcagggata gataaggacc agttaaaaat 1620
gttctcattt cttctctcta agtttgggcc attccgtggc gcatgaattg tccatttctg 1680
tatttacccc tccaagtaat tatgaatata ctatcacaat tccaagagaa agtaaacagc 1740
tttatagatt tttatacgcg tcccaagtgc cagtcctaaa cgtagcaatg actcgttttg 1800
cgcgattagg tgtttgatta taccatctac ttttagctaa gttaactgct gcttcatccc 1860
agcgtttttg ttggagcata cgtaaagaat tagtaaatcc tgctacgcca gtttctccca 1920
tttggaaaac catgttaatc aatgcacagc gccgaacagc atcaagagaa tcataaactg 1980
gttttaattt agcatttctc agaattccgc gaacagcagc atcaacatcc tgattaaaga 2040
gtttttcagc ctcatctttt gtaattacac cattgcaatt acgcccaata gctttatcta 2100

```
attcagattt agcaacatta agtgatggac ttttagtaag caaatgacca atgccagtag   2160
tgtaatagcc ttctgtgtct ttatagattt taagtctaag accttcatct atacgtaaca   2220
tttcaaatat attcataata cctcctaagt atttatagaa ggtatttata aattaaaaga   2280
ggttgttcat tattcggtaa agtgaaggac ccatcacata ttgccactga gtacgaggaa   2340
taagagcaaa agcgtccatc tctggaatca taacaccatc tttattttca aaataagact   2400
cgcaatggca atttctaaac atctcatgct ctactggaat cgtataataa aatagctgta   2460
agtctttatt actagaatat ttaaatacac ctaggtcttc tagaaggtct ggattataat   2520
tgctaaaacc ggtctcttct aagcattctc tttttgcagc ttccagtgca ttcaaatcag   2580
aactttctac acgtcccttt ggaatatccc agcgatgtgc catcattcca ggcttacgag   2640
aaccagtaac ccgacccata aataaatctt tatcttctgt catgaagata ataccagctg   2700
ataatgtttt cattttaatt tcctgcattc agtgataaag ttatttaaat tttgagcata   2760
tttcttttca tcataaatct tttgctgtct gcgtaaacgc catggcattt caatgaacac   2820
acgccatatt cctgataata ctgctgctgt aaaaatatta acaagtatag ttaaaagaac   2880
ccaatctcct attctgtcca ttggattttt tataaaaaaa taaaatacga atgatgatat   2940
aggaagacta atgatatacc acagaagaac cttcttatct gtgaaccaat cagcatttgt   3000
taacttagcg cgaccatttt gaatacacac gaatttatca tctgttacag taaatggctt   3060
agctgcttga taccccattc taaactccct aattaatcgt ttctttgtat cttcggaaca   3120
accattccaa tcaactctat caactggaat gccatcatcc ccatcgtcta agtcatacca   3180
gcgagttttt aaaatcatct gattttcctg caatcactca caaactcttt cattgcttca   3240
ttttcaatat aagaaatgta gctattatat tcttttaatt gtattttgta atcctttttt   3300
ctttgccaat ttattttaaa gttatcataa tgaaaatata aaatgatacc aaagaatgaa   3360
aacaatgaaa taattttagt ataacaaagc tcactccaaa cttctattat atctactgtg   3420
ccgtcgatgt ttaaaataag acagtcaatt aacaatccaa aaagactacc cgcaagagct   3480
gcagccaacg ccacagcaaa aattaaaaat gactcagaaa acgaatattt gactttattt   3540
agttttggct tttgcatcgt gattccttaa caaatttcat aatttcatca aattcatacg   3600
cggcaagttt aagctgatgt tcatttttaa tctttttaca ctgtgctttc caatcacgta   3660
cacgtttacg ataatgtctt ccttgatacc aatatcctat ccaatttaca ggtactaata   3720
aaagtggaac tattaatgga agaattagca ttaacacaag tatttcgcca gaatcaatat   3780
cagtcataac atctaaaaca cctccaataa tcaatagaat tacaaatgat atgagtataa   3840
caggacctat taacacatca gtaggaatta tctggcgctt taattcatac tttaagggtt   3900
tacttggaag atacattgat ggctttgaca tattctctac attccttaac aaatttttct   3960
agtaataaat cactttcaaa attaggattt tccactaatt tatcaaaaag atcatcaaca   4020
atattcaaga tatttctttt actaagaata cgtttatttt catgcttcgt ttcagaatca   4080
actataagag taaagaaata tttctttccc tgaaatttta ctgtagtatc aatatagaat   4140
aaatttgact tttgtaagtt acgtttaaac catgcgtcac ttaaactata aacaccgaga   4200
taatcaaaat cgtcgtttaa ataacatact gtccattcag gagaaatgaa atcagtaaat   4260
tcaacatcaa aatcacacgt caatgaatga attgattcaa tactgttaat aagtattcca   4320
ggacgtatta aagacttttt acctctggaa aatcttccag aaagactttc attagtttca   4380
tatgaagaac cccaataata attacgccct tctgccatac gtttaagaac atttagtaat   4440
```

-continued

```
tggtctggaa catcaacttg tctttggaat tcttcaaaca ttgaattgaa atcactttgc   4500
attttcattc ctatttactc caagtaatag gggccgaagc cccttatcat tatttcagag   4560
aattaatgta ttcctggaca tcggcagagg tggtttcaac cccagaaata ttaccattaa   4620
aggtttcaac tcgagcaagg gtatcttcaa tatcaacctt agtcagtgct gcaatttcaa   4680
ctacatcatc ggcagtacta attccaaggg catttgctgc acgagtttca cggatatatt   4740
ccaatttaac tgcaagttct tggcgagcat catctaactc aactactttc ttggcgattt   4800
caattcgcat ttcagcatac ccatcagctt tagtagtcaa ctgctcagct gttcgacgat   4860
atagtaaacc gagtttagcg tgcattgtta catcttgacc ttcagaaaga agcttgcgaa   4920
tttcacgctc ttttgattcg gcctgtcgat tcttttcgac aataagttca cgaatacgtt   4980
tttcttcatt aatagattta acagaagcag tttttaggtc tttaatttta tcaagtagtt   5040
ttgctgctgc agcagtatac tgttcttcaa cagatagatt tttagccata gcagaaccaa   5100
gtttagtgcg aataaactca acaattttct tcagtgtgtt catagtattt cctttagtta   5160
attaagggtt ttataatcca tgggagtatt atactccgga taggttgtaa actatttcaa   5220
catcgccttt tgctgcttta taaccttcag cccaagatac aaccgagttt ttatccgaag   5280
attcaaattc tggcattggg ctttcgccaa tgttcacgca gtatgtttct tcattttcgt   5340
caaaccaaat aattaaagta gtcatttatt tctccgtttt ctgtatttgt tttgataagt   5400
ctataataac accgtccttg gtgtttgtac acaattattt catattattg aaatattctt   5460
ctgcgatttc gtcgttatca tggtaaactt tagaagacag tttaacataa ccttcagcag   5520
tgaacatgtt aatcacaacc tttacagtat accactgacc atcttcatta cccattactg   5580
cgtaagtttc aaacatcgga tgatcaggac cgataacttt aatatcattc actgtacgac   5640
caaaatcttc tgaaacacat ttcataaaga agttgaacag ttcaccgtaa ttatccattt   5700
cattctccaa gttgttttct gtatcagtag ttggaagaac agggatgtaa acagttttgt   5760
gaaaaaattt ttaaaaagtt ttagggaatt ctagggcagg gaggggaaat caaaggatag   5820
gataatatat tataaagggt ataaactaaa tgatgtctag agaggcccgg aaaggcctag   5880
ataccaaaaa gccctatcat ttagataggg atttaaaatt atttacctag tttagttatt   5940
atagcttcgg cagcagcttt tagcttagat gcagtgttaa tacgattttt aatttcagta   6000
tacgcatcgc caagaacatc aaggctatca gaataaacac ttacactatt gcgttcgcta   6060
tttgaaatag aacctttagt tttacgatca aaatcggtat acacgtcttg aagatcgcgt   6120
gctgccttct ttgcatcatc caatgcatca agagctttat tcaaagcatt aacgtatttt   6180
ttagtatcga acatattctt agaaattttg acaggtgcgc gttcaggagt agctaaggca   6240
gatttaggaa cctgtttacc agatgccagt ttcttagaaa ttttgaaaaa tgctttattg   6300
aaattatttt cttgactcat cgtaaaagaa ctattatcga tgttatacat ttcaatagct   6360
ttagctttcc acttaagaaa atcgccccgg tcttttgggt ccaagtggaa gaatacttta   6420
gtaagatctg cttcagatgg taattttgct gcttcggtta aaaattcggc ataggttttc   6480
atttaaaatc cttgaaataa tttattggtt attaattatt tattatccgt aacagcattc   6540
tctgtgttat tcaaactaaa aagccccaac ctttcggcta gggctaagaa tgttatttga   6600
tttgtttagc agaccaaatg cggtctttaa taatttttttg gaggtcttca acatactcta   6660
ggtcatgagc atgtggatta tctttgaaac tatgagctcg cgcaagtttc tggccttcgg   6720
tcttaattat caaaagttct ttaagaattg cttcatacct agagataatt cctttagcaa   6780
tattttttc ttgtgctgct ttagggtcag ccttaggagc aggtttacca gaaggttttt   6840
```

-continued

```
cgaaagccgc accagtagca accaggcttt tccaggcggt ggtaacatag ttacccacaa   6900
agccttcagc tctcatatcg tcatagaact tgtaccgaga ttcgtcagaa gcatctttat   6960
aagaatattt accagcttta atagcagcag ttgctacagc gcgaacatct gaagcggatg   7020
cttctgtcat taaaaattga gcataagttt tcattgttat ttcctatgtt aattaactca   7080
tctatttata ccaaaaagcc ccaacctttc ggtcagggct aagccttgcg gcaaccttgt   7140
cggggttcca cctgctaagg caagtgtttg tacgaaacgc cgggattcga acccggttat   7200
taagtagttg acgctactca atatttttaa aaggccatat ctcgaccata tccgaacgtt   7260
ccgtcaaaaa cgctactcgg cttacggcaa agatatttcc tcgaatcgat aattcggtgc   7320
gccgtttctg ctgtgatata agagggcatc aacaaatcat aaaaatttat taacacaatt   7380
ccttactcag ggaacatcag tccgacgact tgccggtagc gacccggctt cttgtctggt   7440
cgaggcagaa ggattctaac cttcaaccta cggattagaa gtccgttgct ctatacaatt   7500
gagctatgcc ccgtaattaa aatttcattt ttcgaccttt aaaccatcct tctggaattg   7560
ggtcagtttt cttaatacgt ttagaaactt tttcatctaa tgaatgaatc cacatcatac   7620
caaattggga attcttttcg ccctgttggt gtttatttct ggcgtgagat tctttcattt   7680
tattttccta attaatttg atgagataat agtaccacaa ccctatttaa aagtaaactc   7740
attttaaata aattgcgtat tttttataac ccgctgactc atgacgaaga cccttatcat   7800
tagcaaaacg ctcaatgttg ttaatttgat tctggtcaag ttcagagatg tcaaacacga   7860
aaaagttacg tttgttacca actgttacat agtcagttaa atcaatatca tataggtaat   7920
tgatgtcagc aatcaaagtc ttgacagctt tgctaatttt tactttttcg ttaaaagtag   7980
cttcattgat aaattcttta aatgttttca ttttattctc caatcactca tttgttttga   8040
tagggtaata gtatcacaac taaaaccccg tgtaaataac tttgtgaaat tattttaaat   8100
catctgccca atcgagttta agaggctctt tgtattcacg atctaatacg accggaattt   8160
gtacatcacc gctaaatgat aagggtccaa cattataaga caatgttata tgcggtgtgt   8220
aatcatcaaa atcatgtgta gcacctagtg cccgcgcata catgtgtcga cagcgcagat   8280
attcagaatc tagcacaagt acaagagtcg atccatcttg tgttttccat acttctaaat   8340
gtccagaaga agctacttca aaacttccac ttgatggaac atatggaaca tttactctcg   8400
aataacatat agtcgaatga attttttctc taggaactgg attaggaaca cgtaaagagc   8460
gctggagttc ttccagcgcg tcaagtgtta attctgaaaa cttagctgct acataaagac   8520
ccgttgaaaa gtctttaaat tccattattc ttcatctttt gcttcatctg cagattcagc   8580
agtaagattc ttaacagctt caacgatttc ttcaactttg atggtatcgc cagtgatacc   8640
tactacacga gcaatttcag ccaaagttcc ttgcagaatt ttggattctt ccatcagacg   8700
agccgcttgg tcctgcgtat caagaatacg agatttcaga gttacgattt cagcagacag   8760
tttttgttca atagtttgtt cagacattat agtaccttta gtgtattttt aattttagaa   8820
aaaagttctt caagagaacc atcgtttgta attactaaat cgccatcacg aattggcaat   8880
ccagcttctg taatatgagt atcattggat ttttgaccag gacgaactac atgaattact   8940
gtagcaccca tcgccctagc cgcatccatt tcatgatctt gacgagtatc aggaacgata   9000
taataatcat aacctgagtt aaatttatca agataatcta aagcaaataa ttttacccaa   9060
tacatgcggt cgaagttatt aacaatcaaa tccgtaccta gggcttgcat cagacgacgg   9120
actgaccatt gatcttcaat attatttata acgtcaataa tcttgttaaa tgctacggaa   9180
```

-continued ttaactgatt cttgtccttc gtcatcaaaa aaaacaaaca cgcctttaat tgggctttta 9240
ctattaagat agcaaaatgc ttgttccata atcgtaatta cttctaattt agtcagattc 9300
aaattagtct cacgatcata gtcaattcct tcaaactctt tacgagttaa acaaggatag 9360
tcagtgtttg ctgcgaatac accccatgca taagccaatg catctttaat aggaccagca 9420
agttgatatt tagctgcaga ataattattc atgataaaat ctgcagtagt atcttttcca 9480
ctacgcttta caccactcaa aaagattagt ttcatatgtt tctcctcaaa tttagttaag 9540
attataacac atgaaactta agcattaaac ttctgctata attttaccat ctttttctac 9600
ttgaaaatac gtataaggaa tcgttgctgt acatactaaa gctgggtctg aatcttcagt 9660
gtagctaaat tctacttcag acaggtcaga aacccaaggc ttataaaagt ttattgacat 9720
cacgatttca gttttactgt tatctaaaat gtaaagcgta atgtattcag gacctgtttt 9780
ttgggcagta ttttcgcctg taagatagtt actagttcct aacatccatt catacattcc 9840
tatccacgac ttaagctctt catcaactat aaatctcacg atgagtggat cgtactcaaa 9900
tgtaactcct ggacgctgtg ctcgacccag tccaaatggc ccagtcacag tatcagtaac 9960
aggtatccta attcccggaa taggaactga ctgagcattt aaagtaaaag cagatgtagt 10020
attactatgt ggtattgata ctacaaagtt agttgtattt gcttggttaa aaatttgttg 10080
cagagcttgt gacatatatt cctcataatg ctttataaat gttggtggta taatgggtct 10140
aagtcccttc cattcaattc caattagaac aaacaataga aaagaatgga agataataga 10200
attaatttat tagacttctt aaacgagcag aagtcataaa tggaaatttt tctaaagttg 10260
gctttcgcca atatcttgga tgacaagttg atttaaaatc aagaacaatt ttctttgctt 10320
catcaatagt gttaactcca aagttatcta acattatttt cttttctttt tcccaccgtt 10380
tattagctaa agcagattga agctttttgt ttttaaatgt gtcatttttt ctagaatgag 10440
ttgttccttg tgtcggactc catcctcttc ctaaaataaa tccctcagga attatatctc 10500
catcatgcaa ttttatacat cttttaccat tattataata ttttcgtcca gtttgtgtat 10560
ttgaaatatt atttgcatgt tttctttttta accaaccata aactttatta tttctcctaa 10620
catatttagt tgaaaccgtc atttttatgg ctgcataaga taattttaaa gaatttgggt 10680
gtatttttac taatagctga tgtgcaacat aatgctcttc tggagttaaa tcaaccaagt 10740
tagaagcatc attactaccg cctaaacatt tcggaataat atgatgtctt tctttatatc 10800
cagtaagggc tctattgcga gccctatcaa ttagtgaatt ataaattttt tcataattca 10860
tcgtacattg ccccaaactt tgtttgcaga gaaacgtttt cctttggagt agaagctttg 10920
gagtggcatc aacacaacgt tcgcccagtc tttcggggcg atttcaacaa ggctacccat 10980
aatattaccg ggtatatatg ccttaatcat ttggtctgca cccctaaatc ctttcacttg 11040
actccaatca atttttaatt tcgttttatt agtaatagta ggtgtatttg aatattgctt 11100
taaaagctct tctagaaatt gctgacgagc tttaggtgga atatagtgca agtttaatcc 11160
gtacattaaa ttatgcttac ctaaaccaag gtaaattatc aaaggaaatt tatcccagta 11220
aggaagagtt tccttgtgtt tagcatcata agcaaaagca tatattcgtc ccggctgcgg 11280
gcgaataact ttatgtcctt ttacttgctt aatagtttca gcaaaccact ttctggtttt 11340
attattaatt gctgcgcctt cattacgaat tttatcacgc aatgtttgtc tgaatgaatt 11400
tatcataagc agttgtcttt cttgcttatt gagtttattc attggttttg attcaaattt 11460
ttgaatcttt tcagccgttt taattcctga agcatatttt gacattgctg aagtaaacgt 11520
agagtatttg attcctcttt cttcagcaaa ttgctttcct gtcattcctt ttgctttggc 11580

-continued

```
cttttgtat tcaagaccta tctgaatcca tttcttttcg tttaatgatt gcttaacctt  11640
tggaacttgg ggagtgcttt cattaattat ttgaaaaata gccattatgc cccttaaag  11700
ccaagagctc gtaatccatc ttctgttaga attctaaatt ttattccacg cttttcagct  11760
aacgattgtg ctgctttcca tttatcagtg ttaacagaat atgtataaat ttcattcata  11820
aatcttttct tcgctgcggt tgttagatgt gctggtttaa ctggtggttg tgtttctttt  11880
ttaggtttta tttcaataaa aaattcttgt ccagaagaat ctttcatcca aatatccatg  11940
aagtatctac gtttttccc ttctgcatta caaaaataag gaattactgc tgtttcacta  12000
ccccatgcaa taatttctgg atttttatct aaccattcaa aaaagaattt ttcccaattt  12060
gatctatacg taattttttt agggtcacct ctgtattttg atatattttt aggaacccat  12120
tttccagaat atgccattgg attctcctta taaatagata atatatttat aaacaggagg  12180
gcccatgctc tttacatttt ttgatccgat tgaatatgcg gccaaaacgg tgaataaaaa  12240
cgcgccgact attcctatga cagatatttt tagaaactat aaagactatt tcaaacgcgc  12300
tcttgcggga taccgcttac gtacttatta tattaaaggt tcaccacgcc cggaagaatt  12360
agcaaatgct atatatggaa atccacagtt gtattgggtt ttattgatgt gtaatgataa  12420
ttatgatccg tattatggat ggattacttc gcaagaagct gcttatcaag catctataca  12480
aaaatacaaa aacgtaggtg gagaccaaat agtatatcac gtgaatgaga atggtgaaaa  12540
attttataat ttaatatcat acgatgataa tccatatgtt tggtatgaca aaggtgataa  12600
agctagaaaa tatcctcaat atgaaggagc acttgctgcg gtcgatacgt atgaagctgc  12660
tgttcttgaa aatgaaaaac ttcgtcaaat aaaaataata gcaaaatcag acatcaattc  12720
atttatgaac gaccttatac gtataatgga gaaatcttat ggaaatgata agtaataacc  12780
tcaactggtt tgttggtgtt gttgaagata gaatggaccc attaaaatta ggtcgtgttc  12840
gtgttcgtgt agttggtctg catccacctc aaagagcaca aggcgacgta atgggtattc  12900
caactgataa attaccatgg atgtcagtta ttcaacctat aacttctgca gcaatgtctg  12960
gaattggagg ctccgttact ggtccggtag aaggaactag agtttatggt catttttttag  13020
acaaatggaa aactaacgga attgttcttg gcacgtacgg tggaatagtt cgcgaaaaac  13080
ctaatagact tgaaggattt tctgacccga ctggacagta tcctagacgt ctaggaaatg  13140
atactaacgt attaaaccaa ggcggagaag taggatatga ttcgtcttct aa          13192
```

<210> SEQ ID NO 6
<211> LENGTH: 660
<212> TYPE: DNA
<213> ORGANISM: Artificial Sequence
<220> FEATURE:
<223> OTHER INFORMATION: partial sequences of Bacteriophage EK88P-1

<400> SEQUENCE: 6

```
tccaactgat gataatccaa atatgtcaat ggctgaaatg cttcgccgtg atgaaggatt    60
aagactaaaa gtttattggg atactgaagg atatccgaca attggcattg gtcatcttat   120
catgaagcaa ccagttcgtg atatggccca aattaataaa gttttatcaa aacaagttgg   180
tcgcgaaatt actggaaatc caggttctat tacaatggaa gaagcggtaa ctttatttga   240
gcgtgatttg gctgatatgc aacgtgacat taaatcacat tctaaagttg gcccagtttg   300
gcaagcagtt aatcgttctc gtcaaatggc attagaaaat atggcattcc aaatgggcgt   360
tggtggcgta gctaaattta acacaatgtt aactgctatg ttagccggag attgggaaaa   420
```

agcatataaa gccggtcgtg attcattgtg gtatcaacaa acaaaaggcc gtgcatcccg 480
tgttaccatg attattctta cagggaattt ggaatcatac ggtattgaag tgaaaacacc 540
ggctaggtct ttgtctgcaa tggctgctac tgtagcaaag tcttctgacc cggctgaccc 600
tcctattccg aatgattcaa gaattttatt caaagaacct gtttcttcat ataaaggtga 660

<210> SEQ ID NO 7
<211> LENGTH: 1367
<212> TYPE: DNA
<213> ORGANISM: Artificial Sequence
<220> FEATURE:
<223> OTHER INFORMATION: partial sequences of Bacteriophage EK88P-1

<400> SEQUENCE: 7
gaagtatcac cgtcaggaag aagaacaaga aaaactgttg ataatttgta tgatataaca 60
aatgctgatg gtaatttttt agtagccggc gataaaaaga ctaacgtcgg tggatcagaa 120
atttattaca acatggataa tcgtcttcac caaatagatg gaagcaacac aatatttgtg 180
cgtggcgatg aaactaagac agttgaaggt aatggaacta tcctagtcaa aggtaatgtt 240
actattgtag ttgaaggtaa tgctgacatt acagttaaag gagatgctac tactttagtt 300
gaaggaaatc agactaatac agtaaatgga aatctttctt ggaaagttgc tgggacagtt 360
gattgggacg ttggtggtga ttggacagaa aaaatggcat ctatgagttc tatttcatct 420
ggtcaataca caattgatgg atcgaggatt gacattggct aatatacttc caatgagcgc 480
tgatttagga gaatccatgg aaggttcttc tatcgacgtc acctttaccg ctcaattaga 540
aacaggtgaa acgttagtat ctataaatat aactagttac gaagaaactc ctggggtttt 600
aatagaagaa aatcgtttat atggaacgta tgaatctgta tttggatttg gaaatgatgc 660
gttgaaatat cgtttagata atgaatttaa aaccgctgct tcatgggaag accttccaac 720
tgattctaat actcagttat atttatggaa agctcctcaa aacctccaga agacattcac 780
ttacgaagta acattaatat atgactacca agaacaaagt gaatccggag gttctggcag 840
taattctagg tcatcttctg atactactga accgacgaat cctccagctc caataagaaa 900
aactcttgtt aaaaattaca caaaaactat agttggaaat tggagtcgtt gggctaataa 960
attgagaagc tatgtgtatg agaggccata aatgtcagga ttaagttatg ataagtgtgt 1020
tactgccggc catgaagcat ggcctccaac ggttgtgaat gctacacaaa gtaaagtatt 1080
cactggagga attgctgttc tcgtagcagg tgatccaatt acagaacata cagaaattaa 1140
aaagccatat gaaacacatg gcggagtgac acaacctaga acttctaagg tatatgtcac 1200
tggaaagaaa gctgttcaaa tggctgatcc aatatcatgc ggtgatactg tggctcaggc 1260
atcatctaaa gtattcatta aataggattt aaaatggcaa atacccctgt aaattatcaa 1320
ttaacaagaa cagcaaatgc tattcccgag atattcgtcg ggggtac 1367

<210> SEQ ID NO 8
<211> LENGTH: 1820
<212> TYPE: DNA
<213> ORGANISM: Artificial Sequence
<220> FEATURE:
<223> OTHER INFORMATION: partial sequences of Bacteriophage EK88P-1

<400> SEQUENCE: 8
ggatatttac ctacttcaaa atcggctgct caaactgaaa ttatgctaac ttgtacagat 60
gcattgaata gaaattacat tactattcct cgtggtactc gctttttagc atatgcaaag 120
gatacttctg ttaatcctta taactttgta tctaccgaag atgttattgc tattcgcgat 180

```
aaaaataacc aatattttcc gcgtttaaaa ttggcccagg gacgtatagt aagaactgaa    240
atcatttatg acaaattaac acctattatc atttatgaca aaaatataga tagaaaccaa    300
gttaaactat acgttgatgg agcagaatgg attaactgga caagaaagtc aatggttcat    360
gctggttcta catcaacaat ttactacatg cgtgaaacta ttgatggaaa tactgaattt    420
tattttggtg aaggtgagat ttctgttaat gcggcagaag gagcattgac cgctaattac    480
attggaggtc ttaaacctac ccagaactct acgattgtta ttgagtacat cagtactaac    540
ggcgcagatg cgaacggcgc agtcggattt tcatatgcag atacattaac aaatataact    600
gtcatcaaca ttaatgaaaa tccaaacgat gacccagatt ttgttggggc agatggcggc    660
ggtgacccag aagatattga acgtattcgt gaattgggta ctattaaacg tgaaacccag    720
caacgctgcg taactgcgac tgactatgat acattcgttt cagagagatt tggttctatt    780
attcaagcag ttcagacttt cactgattct actaaacctg gttatgcatt tattgctgct    840
aaacctaaat cagggctata tttaactact gtacagcgcg aagatattaa aaattatctc    900
aaagactata atttagctcc tattacacca tcaattattt ctcctaatta tctttttatt    960
aagactaatt taaaagtcac atatgcttta aataagctgc aagaatccga acagtggctc   1020
gaaggtcaaa taattgataa aattgatcgt tattataccg aagatgtaga aatttttaat   1080
tcatctttcg ctaaatctaa gatgttgaca tatgtagatg atgcagatca ttctattatt   1140
ggctcatcag cgacaattca aattgttcgt gaagtacaaa acttctataa aacgcctgaa   1200
gcaggtatta aatacaataa tcaaataaaa gatcgttcta tggaatctaa tacgttttca   1260
tttaattccg gacgaaaggt tgtaaatcct gatactggtt tagaagaaga tgtattatat   1320
gacgttcgta tagtatcaac agaccgagat tctaaaggaa ttggtaaagt tattattggt   1380
ccatttgctt ctggcgatgt tacagaaaat gaaaacattc agccatatac aggcaacgat   1440
tttaacaaat tagcaaattc tgatggacgc gacaaatact atgttatcgg cgaaataaat   1500
tatccagctg atgtgattta ctggaatatc gctaaaatta atttaacatc tgaaaaattt   1560
gaagttcaga ctattgaatt atattctgac ccaaccgatg atgttatctt tactcgcgat   1620
ggttcactga ttgtatttga aaatgactta cgtccacaat acttaactat cgatttggag   1680
cctatatcac aatgacagta aaagcacctt cagtcactag tctcagaatt tccaagttat   1740
ccgcaaatca ggtgcaagta cgctgggatg acgttggtgc taatttctac tattttgtag   1800
aaatcgctga gacaaaaaca                                              1820
```

<210> SEQ ID NO 9
<211> LENGTH: 1128
<212> TYPE: DNA
<213> ORGANISM: Artificial Sequence
<220> FEATURE:
<223> OTHER INFORMATION: partial sequences of Bacteriophage EK88P-1

<400> SEQUENCE: 9

```
tgggaatatt tgtggtcaga gatatataaa agaaacattt atttaaatgc tgacaaacgc     60
gatgctgttg caagattttt tgaatcacgt agctatgatt tttattccac taaaggaatt    120
gaagcatcat acaaatttct ttttaaagtt ctttataatg aagaagttga aattgaaatt    180
gaatctgggg ctggtactga atatgatata atcgttcaat ctgattcttt gaccgaagac    240
ttagtaggac aaacgattta taccgctaca ggaagatgta atgttactta tatagaaaga    300
agctattcta atggtaaatt gcaatggacc gtgactatac ataatctttt ggggcgttta    360
```

-continued atagcagggc aagaagttaa agcagaaaga cttccaggtt tcgaaggcga aattattcgc 420
ggggttaaag gaaaggattt gcttcaaaat aatatagact atattaatag aagtagatca 480
tattatgtaa tgaaaattaa atccaattta ccttcttccc gctggaaatc tgacgttatt 540
cgttttgttc atccagtagg atttggattt atagcaatta cacttttaac aatgtttatt 600
aatgttggtt taactcttaa acatacagag actataatta ataaatacaa aaactataaa 660
tgggattctg gattgcctac tgaatatgct gatagagtag ctaaattaac tccaactggt 720
gaaattgagc atgattcagt aacaggcgaa gcaatttatg agcctggccc aatggccggt 780
gtagaatatc ctcttcctga tgactataat gctgaaaata acaattcaat atttcaaggt 840
caattgccgt ctgaacgacg taaattaatg agtcctttat ttgatgcatc tggaacaaca 900
tttgcgcaat ttagagattt agttaataaa cgtctaaaag ataatatagg aaatccaaga 960
gaccctgaaa atccaacaca ggttaaaata gatgaatgat tcaagtgtta tctatcgtgc 1020
gatagttact tcaaaattta gaacagaaaa aatgttgaat ttttataatt caattggaag 1080
tggtccggat aaaaacacta tctttatcac atttggaaga tcagaacc 1128

<210> SEQ ID NO 10
<211> LENGTH: 3888
<212> TYPE: DNA
<213> ORGANISM: Artificial Sequence
<220> FEATURE:
<223> OTHER INFORMATION: partial sequences of Bacteriophage EK88P-1

<400> SEQUENCE: 10
tatcgttgtt tagatgttcc tgacacagga atgtgttcaa ttgagtcttt aactaataag 60
gatgaatgcc ttaagttagg tggaaaatgg actccttctg ttaggtcaat gactcctcct 120
gaaggtcgag gagacgcgga aggaacaatc gagcctggag acgggtatgt ttgggaatat 180
ctttttgaga ttccgcctga tgtgtctata aatagatgca cgaatgaata tatcgtggtt 240
ccttggcctg aggaattaaa agaagacccg actagatggg gatatgaaga taatctcaca 300
tggcagcaag atgattttgg attaatttac cgtgttaagg caaatactat ccgttttaaa 360
gcatatttag attcagttta ttttcctgaa gctgcactgc ctggaaataa aggatttaga 420
caaatatcaa taatcacgaa tcctcttgaa gctaaagctc atccaaatga cccaaacgtt 480
aaagctgaaa aggattatta tgatccggaa gatttaatga ggcattcggg cgaaatgatt 540
tatatggaaa ataggccacc tattatcatg gcaatggatc aaacagaaga aatcaatatt 600
ctgtttacat tttaacttaa gggagcccat gggctccctt tttctttata aatactataa 660
actcataagg aaaccgctat gttcattcaa gaaccaaaga aattgattga taccggcgaa 720
attggtaacg cttctactgg tgatatctta ttcgacggtg gtaataaaat taatagtgat 780
tttaatgcaa tttataatgc gtttggcgat caacgtaaaa tggcagtagc aaatggtact 840
ggagcagatg gtcaaattat ccatgctact ggatattatc aaaaacactc tattgcagag 900
tacgcaactc cagtaaaagt tggcactaga catgatattg atacctctac tgtaggtgtt 960
aaagttatca ttgaaagagg cgaacttggt gactgcgttg aatttattaa ctcaaatgga 1020
tctatatcag ttactaatcc tttaacgatt caagcgattg attcaattaa aggtgtttct 1080
ggtaatttag tagtaactag cccatatagt aaagtaactt tacgctgtat ttcatctgat 1140
aattctactt cggtttggaa ttattctatt gaaagtatgt ttggacaaaa ggaatcacca 1200
gctgaaggta catggaatat ttctacatct ggatcagttg acattccatt atttcatcgc 1260
actgaataca atatggctaa attgctagtt acatgccaat cagtagatgg aagaaaaatt 1320

```
aaaacagcag aaataaatat tcttgtggat actgttaatt cagaggtaat ttcttctgaa   1380
tatgctgtca tgcgagttgg gaatgaaacc gaagaagacg aaatcgctaa tattgcattt   1440
agtattaaag aaaattatgt aacggcgact ataagttctt caactgtcgg tatgagagca   1500
gcagttaaag ttatcgctac gcagaaaatc ggggtggctc aataatgaaa caaaatatta   1560
atatcggtaa tgttgttgat gatggtaccg gtgactacct gcgtaaaggt ggtataaaaa   1620
taaatgaaaa ctttgatgag ctttattatg agcttggtga tggagatgtt ccatattcag   1680
ccggtgcctg gaaaacttat gatgcttcat ctggtcaaac attaaaagct gaatggggaa   1740
aatcatacgc tattaatacc tcttctggaa gagtaactat aaatcttcca aaaggaactg   1800
tcaatgatta caacaaggta attagagcta gagacgtatt tgctacatgg aacgtcaatc   1860
cagttacact agtagctgct tccggcgata cgattaaagg ttctgcagta ccagttgaaa   1920
ttaatgttca attcagtgat ttagaattag tgtattgcgc cccaggacgt tgggaatatg   1980
tcaaaaataa acaaattgac aaaattacca gttcagacat tagtaatgta gctcgtaaag   2040
aatttttagt cgaagtccaa ggacaaacag actttttaga tgttttccgc ggaactagtt   2100
ataatgtaaa taacatcaga gtaaaacatc gtggtaacga attgtattac ggcgatgtat   2160
ttagtgaaaa cagcgatttt ggctctccgg gcgaaaatga aggtgaatta gttcctcttg   2220
atggatttaa tattcgatta agacagcctt gtaatattgg tgacactgtt caaattgaaa   2280
cgtttatgga tggcgtatca caatggagaa gttcatatac aagacgtcaa attagactgt   2340
tagattcaaa attaacgtca aaaacttctt tagaaggaag catttacgtt actgatttat   2400
caacaatgaa atcaattcca ttttcagctt ttggattaat tccaggtgaa cctatcaatc   2460
ctaattctct tgaagttcgt tttaatggaa ttttgcagga attggctgga acagttggaa   2520
tgccattatt tcattgcgtt ggtgccgatt cagacgatga agtagaatgc tctgttttag   2580
gtggaacttg ggaacagtct cataccgact attcagttga aactgatgaa aacggcatac   2640
cagaaatttt acatttcgat agagtatttg agcatggcga cattatcaat atcacctggt   2700
ttaataatga tttaggtaca ttattaacaa aagatgagat tattgatgaa actgataatc   2760
tctatgtatc gcaaggacca ggagtagata tttctggtga tgtaaattta acagactttg   2820
ataaaattgg ttggccaaat gtagaagcag ttcaatccta tcaacgcgaa tttaatgctg   2880
tttcaaatat ctttgatacg atttatccta tcggaactat atatgaaaac gctgttaatc   2940
caaataaccc tgttacatat atgggattcg gctcatggaa attatttggg caaggaaaag   3000
ttttagttgg atggaatgaa gatatttcgg accctaactt tgctctaaat aacaacgatt   3060
tagattcggg tggaaatcct tcacatactg caggcggaac aggtggttct acttctgtta   3120
cattggaaaa tgctaatctt cctgcaactg agacagatga agaagttcta atagttgatg   3180
aaaatggatc agtcattgtt ggtggatgtc aatacgatcc agatgaatct ggtccagttt   3240
acacgaaata ccgtgaagct aaagcatcta ctaactctac tcacactccg ccaacatcaa   3300
taactaacat tcaaccatat attacagttt atcgttggat aaggattgca taatgagttt   3360
acttaataat aaagcgggag ttatttcccg cttagccgat tttcttggtt ttagacctaa   3420
aactggcgac atcgatgtaa tgaatcgtca atcagttggg tcagtgacaa tttctcaatt   3480
agcgaaagga ttttatgaac caaacgtaga atcagctatt aatgatgttc ataatttttc   3540
tataaaagac gttggtacaa ttattactaa taaaactggt gtttctcctg agggtgtttc   3600
tcaaactgat tattgggcat tttcgggaac tgtaacagat gattcgcttc ctcctggttc   3660
```

```
tcctgttact gtgttagtat ttggtcttcc agtttcagca acaactggaa tgacagctat   3720

tgagtttgtc gccaaagttc gtgttgctct acaagaagct attgcgtcat ttactgctat   3780

caattcatat aaagaccatc caacagatgg tagtaaatta gaagttactt atttagataa   3840

tcaaaaacat gtattaagca catattctac atatggaata actatttc                3888


<210> SEQ ID NO 11
<211> LENGTH: 3970
<212> TYPE: DNA
<213> ORGANISM: Artificial Sequence
<220> FEATURE:
<223> OTHER INFORMATION: partial sequences of Bacteriophage EK88P-1

<400> SEQUENCE: 11

gcacaaactg taactttaga taatcagcag actcctacag tattttatca ttttgagaga     60

acagcatgag taataataca tatcaacacg tttctaatga atctcgttat gtaaaatttg    120

atcctaccga tacgaatttt ccaccagaga ttactgatgt tcaggctgct atagcagcca    180

tttctcctgc tggcgtaaat ggagttcctg atgcatcgtc aacaacaaag ggaattttat    240

ttcttgccac tgaacaggaa gttatagatg gaactaataa taccaaagca gttacaccag    300

caacgttggc aacaagatta tcatatccaa acgcaactga aactgtttac ggattaacaa    360

gatattcaac caatgatgaa gccattgccg gagttaataa tgaatcttct ataactcctg    420

ctaaatttac tgttgccctt aataatgcct ttgaaactcg tgtttcaact gaatcaaaga    480

atggagttat taaaatttcg tcattgccgc aagcattggc aggtgctgat gatactactg    540

caatgactcc attaaaaaca cagcagttag ctattaaact aattgcgcaa atcgctcctt    600

ctgaaaccac agctaccgaa tcggcccagg gtgttgttca attagcgaca gtagctcaag    660

ttcgtcaagg aactttaaga gaaggctatg caatttctcc ttatacgttt atgaattcat    720

ctgctactga agaatataaa ggcgtaatta aattaggaac acaatcagaa gttaactcga    780

ataatgcttc tgttgcggtt actggcgcaa ctcttaatgg tcgtggttct acaacgtcaa    840

tgagaggcgt agttaaatta acaacaacag ccggttcaca gagtggaggt gatgcttcat    900

cagccttagc ttggaatgct gacgttatcc accaaagagg cggtcaaact attaatggaa    960

cacttcgcat taataacacg cttacaatag cttcaggtgg agcaaatatt accggaacag   1020

ttaacatgac cggtggttat attcagggta agcgtgttgt aacacagaat gaaatagata   1080

gaactattcc tgtcggagct attatgatgt gggcggcaga tagtcttcct agtgatgctt   1140

ggcgcttctg tcatggtgga actgtttctg cgtcagattg cccattatat gcttctagaa   1200

ttggaacaag atacggcgga agctcatcaa atcctggatt acctgatatg cgtggtcttt   1260

ttgttcgtgg ctctggtcgt ggctctcact taacaaatcc aaatgttaat ggtaatgacc   1320

aattcggtaa acctagatta ggtgtaggtt gtaccggtgg atatgttggt gaagtacaaa   1380

aacaacagat gtcttatcat aaacacgctg gcggatttgg tgagcatgat gattctggag   1440

cattcggtaa tacccgtaga tcaaattttg ttggtacacg taaaggactt gactgggata   1500

accgttcata cttcaccaat gatggatatg aaattgaccc agcatcacaa cgaaattcca   1560

aatatacatt aaatcgtcct gaattaattg gaaatgaaac acgtccatgg aacatttctt   1620

taaactacat aattaaggta aaagaatgac agatattgta ctgaatgact taccattcgt   1680

tgacggccct cctgcagagg gccagagccg catttcctgg attaaaaacg gcgaagaaat   1740

attaggagct gacacacagt atggaagtga aggttcaatg aatagaccta cagtttctgt   1800

actaagaaat gttgaagttc ttgataaaaa cattggaata ctcaaaacat ctttagaaac   1860
```

```
cgcaaatagt gatattaaaa caattcaggg catcttagat gtatctggtg atattgaagc   1920
tttggcccaa ataagtatca ataaaaagga tatttctgac cttaaaacgc taaccagtga   1980
acatacagaa atattaaatg ggactaatag tacggttgac agcattcttg ctgatattgg   2040
tccatttaac tccgaggcca actctgtata cagaacaatc agaaatgatt tactgtggat   2100
aaagcgtgaa cttggacaat acacaggtca agatattaat ggtcttcctg ttgtaggaaa   2160
tcctagtaca ggaatgaagc atcgcattat taataatact gatgtcatta cttcacaggg   2220
aatacgttta agcgaattag aaacaaaatt tattgaatct gatgtaggtt ctttgactat   2280
tgaagttggt aatcttcgcg aagagcttgg accaaaacca ccgtcatttt cacagaacgt   2340
ttacagtcgt ttaaatgaaa ttgacactaa acagacaaca gttaagtctg acattagtgc   2400
tattaagacc tcaataggat atccaggaaa taattcgatt atcacgagtg ttaatacaaa   2460
cactgataat attgcatcta ttaatttaga gctaaatcaa agtggaggta ttaaacagcg   2520
tttaaccgtt attgaaactt ctattggctc agacgatatt ccttcgagta ttaaaggcca   2580
aattaaagat aatacgactt caatcgaatc gctaaatgga atcgtcggtg aaaacacttc   2640
atctggttta agagcgaatg tttcatggtt aaaccaaatt gttggaactg attctagcgg   2700
tggacaacct tctcctcctg ggtctctttt aaaccgagtt tctacaattg aaacttctgt   2760
ttcaggcttg aataatgatg ttcaaaacct acaagtagag attgggaata acagcacagg   2820
aattaaagga caagttgtag cgttaaatac tttagtaaat ggaactaatc caaacggccc   2880
aactgttgaa gaacgcggat taaccaattc aataaaagct aacgaaacca acattgcatc   2940
agttacacaa gaagtgaata cagccaaagg caatatatct tctttacaag gtaatgttca   3000
agctctccaa gaagccggtt atattcctga agctccaaga gatgggcaag cttacgttcg   3060
taaagacggc gaatgggtat tgctttctac ctttttatca ccagcataac atggggccgc   3120
aaggccccaa aggattttaa atgtcaggat ataattctca gaatccaaag gaactcaaag   3180
atgtcattct aagacgttta ggggctccaa ttattaatgt tgagttaaca cccgatcaaa   3240
tctatgattg catccagcgt gccctagaat tatacggtga ataccatttt gatggactta   3300
acaaaggttt tcatgttttt tatgtagggg atgacgaaga aaagtacaag actggagtct   3360
tcgatttaag aggttctaac gtatttgcag taacccgcat tttacgcaca aatattgggt   3420
caataacatc tatggatgga aatgctacat atccatggtt tactgacttt cttttaggaa   3480
tggctggtat taatggtggc atggggactt cttgcaatag attttatgga ccaaatgcct   3540
ttggagctga tttagggtat tttacccagc ttaccagtta catgggaatg atgcaagata   3600
tgctttcgcc tattccagac ttttggttta attcagcaaa tgaacagctc aaagtcatgg   3660
gaaacttcca aaaatatgat ttaattatcg tagaaagctg gactaaatca tatattgata   3720
ctaataaaat ggttggaaat acagtaggat atggaacagt cggtccacaa gatagctggt   3780
cattatctga acgatataat aacccagacc acaatttagt cggtcgcgtt gttggtcaag   3840
acccaaatgt taagcaaggc gcttataata atcgttgggt gaaagactat gctacagctt   3900
tagctaaaga attaaatggc caaattttag cacgtcacca aggcatgatg cttcctggcg   3960
gtgttacaat                                                          3970
```

<210> SEQ ID NO 12
<211> LENGTH: 952
<212> TYPE: DNA
<213> ORGANISM: Artificial Sequence
<220> FEATURE:

<223> OTHER INFORMATION: partial sequences of Bacteriophage EK88P-1

<400> SEQUENCE: 12
ttttggtagg ttaatatggc tacttatgat aaaaatcttt ttgctaaatt agaaaatcgc 60
actggttatt ctcagactaa tgaaactgaa atactaaatc cttatgtaaa tttcaatcat 120
tataaaaaca gccaaatatt agctgatgta ttagtggctg aaagcattca aatgcgaggt 180
gtagaatgct attatgttcc aagagagtat gtttcccctg atttgatatt cggcgaagac 240
ttaaaaaata aatttactaa agcttggaaa ttcgccgcat atttaaattc atttgaagga 300
tatgaaggag ctaaatcgtt ctttagtaat tttggtatgc aagtacagga tgaagttact 360
ttatccatta atccaaactt gtttaaacat caagtaaacg gaaaagaacc taaggaaggc 420
gatttgatat attttcctat ggataacagc ttattcgaaa ttaactgggt tgaaccatat 480
gatccatttt atcaattagg ccaaaatgct attcgtaaaa ttacggcagg taagttcatt 540
tattccggtg aagaaattaa tccagttcta cagaaaaatg aaggaattaa cattccagaa 600
tttagtgaat tagaattaaa tcctgttcgc aatcttaatg gcattcatga tattaatatt 660
gatcagtatg ctgaagtaga tcaaattaat tctgaagcta aagaatatgt tgaaccttat 720
gttgttgtca ataatagagg caaatctttc gaatctagcc catttgataa tgatttcatg 780
gattaataaa tattataaac taattaaagc ccagattagg agaaatcatg tttggttatt 840
tttataattc gtcttttaga cgatatgcta ccttgatggg cgatttgttt tcaaatatcc 900
aaatcaaacg tcagttagaa tctggtgata agtttatacg tgttcctatt ac 952

<210> SEQ ID NO 13
<211> LENGTH: 1887
<212> TYPE: DNA
<213> ORGANISM: Artificial Sequence
<220> FEATURE:
<223> OTHER INFORMATION: partial sequences of Bacteriophage EK88P-1

<400> SEQUENCE: 13
aatttacgag cggctacgag gtcgtttgat ttaatagctt caattaaacc ttccattaaa 60
aatcctcttg ttcttggtcg gggtcttgga aacgagcctc tttagactct tcttcaattt 120
gcttggcttc ttgttctatt tcttcatcag tcatctgcaa aatatctttc atagcagttc 180
tgtgagaaat atatttacca ataaatggtt ctgccatggt tagcatatta attcttcgtt 240
ccaaaatttc tgcttctttg agctcagcaa agtagctatc ccgatgaaat tctatcttaa 300
tattatttat ttcatcattc cactcatctt ctgtgattat acctttaagc aaaagatttg 360
ttttaagcgg atctaggaaa acttcttcaa atttatgctg aagctcacga ataaatttag 420
caaacgttaa ttcatcacgt gtagtgctag ttccagaatc aaacattaca ccgccttgtt 480
ggtcttgcgg aatgcgtgaa agaggaacac gtaatgccat ataaagagct tgtctaaacc 540
aacgaatatc ttccatattg ccagtattat cagcaccagg aagagtatca acttctgtca 600
cagctttacc atcacggcgc tgcaaccaat agtcttcggt catagacata ttatgctgtt 660
gattttttat tttacctgtt gatgcatcat atactacacg gtttttcatc gtgttcatga 720
catgttgcat gtgctcggca gctttacgag caggcatatt acctgtatct acataccaaa 780
cacgacggtc aggagcacga gtaatgcgat aaatgactac agcatcttct aataatttta 840
attggttagc aggtttaaca gcacgatgta aatacccgat gatattttta ccgcaacaat 900
cgactaatcc agaatgggca taaactacgg cagctttagg aatttttatt tttgtgccag 960
cttcatacat tctaccatca catgcatatg actcatgggc agtatcatat ataaaatatt 1020
ctttgtaacc tttaactatt tttgtgccag cttcagtttc tgttataatt tcacgaacat 1080
actgaacttg gcgagggtct aatctacgta attcttttat gccttctttt ggacgtttta 1140
gatcaatgat tttatgaaag aaaattcttg aatcaacata ccaacgtcta aaatgatcag 1200 aacctttcg ttgaaacgat agatgattta atacatcgct aaattcatct aacatcatat 1260
ttttaatttt tgggctaaat ttagatttat ccaaatttaa cgctacgact tcagtatcat 1320
cttcatagac gatagcgtct gaaacgattt ctgaaactgc attatctact tcatagttat 1380
tcatgagatt acgatatgta tcaataagct cacgagtagt tttcattcct ggttcatatg 1440
aaccaaaaat tgtttggaat gcagcattat aaggagaagc agcttcgttc gagcttactt 1500
caaattctct tgctccatca tcaagctttg gggctgtaat ggaaacaaga tcttcttttt 1560
cttggtcttt aaaatttcgt tcgtccattt tagcccatgg agcaaacaaa cttaatacat 1620
taaatttcat tgtattctcc aaatgggaat tatagttata tttataatgg acttctctgc 1680
tttaagcagg atggggattt ctccccattc attttattcc caataatcga gagcgagagt 1740
tacttcaaag gtttggattt cattgtttga atcccaatct aattgaagtt cacccacgtt 1800
agtaggccac agacctttaa tttcaatttc ttttgttact gttttagcgt cacgagcata 1860
ttggcgaaca atagcgctct ttttata 1887

<210> SEQ ID NO 14
<211> LENGTH: 823
<212> TYPE: DNA
<213> ORGANISM: Artificial Sequence
<220> FEATURE:
<223> OTHER INFORMATION: partial sequences of Bacteriophage EK88P-1

<400> SEQUENCE: 14
gtaatttcgt ttccttgccc agcagcaatg ctttgccagt caacaaactt ctgacgtgca 60
tcatgcgcct cgtcattcat tactgtaata gtccagtcat cgaatgtacg atcgcctgct 120
acgttaattt tacggttcat aaatccgact ggaatttttt ctacaatacc agccggtaaa 180
gcagtggctt tacattgaaa cgtaaaattt tgtccaagat aagaaatttc tacttggaat 240
aagttaggtc gagcaaaatc accagattca aacgctcgtg ttacatcatc tacaaacata 300
ttagcctctg tagtatttat atccctatgt ttaacctagg gcatatagaa ttaaagaatt 360
aaggatatag tgtatttata tggcctgccg aaacaggcct ttagaatgca ccgtattaac 420
ctgcaagacc agttaactca tcgaaatctg caccagtagc agttgctacg aagtttaagg 480
taatgtagtt aatgcttcta gccggttgga tgtagaatgt tgcaacaaac tcatttctat 540
caattactga cggagtgtta tttgttgtat cgcaaactac acgatattca taaattccac 600
cgagagcttt aattccctgc aagtactggg aagtttctgt gcggaacgat gaacgagtaa 660
acgcgttgtt taattcgaac aaacgatatt ttgaactacg tccgatattc gttttcaaca 720
tattaaacag acgacgaacg ttaatacgat caaatggaga aggaacagaa gtagctgttt 780
tatcaccata caatacgtaa ccatcaccac ctgtaccagt tac 823

<210> SEQ ID NO 15
<211> LENGTH: 2893
<212> TYPE: DNA
<213> ORGANISM: Artificial Sequence
<220> FEATURE:
<223> OTHER INFORMATION: partial sequences of Bacteriophage EK88P-1

<400> SEQUENCE: 15

```
taggcatttt gtgaaagata tttgtcatct tctggtttat gttttaacca acctgatgca     60
gcaagaatcg cagcggcacg agctgaagca acacagaacg ttgcagtata agttgattct    120
ttttggatat gcgaaaccat ttcacatacc attcggtata atgaacgacc agcttcaggt    180
gcagatgcat aactcaaatc aatgaatcca gtatcagtaa ttcctgtaac tttatagcgt    240
tttgacactg taatcaaaga ctgcagaata tctttattga tttcatccgc catttcagtt    300
gcaagcaaat cttccaagaa attaggagca tcgaatccat ttgcttctaa atcttgtgct    360
aattcaactg tgatgccagt tttaagttta cgagatttaa ctgcggtttg ccatttatta    420
atctggaatc tagcatccgc aatttcacta tcagagcttt caaatttgct tgttactgca    480
gcatcagaaa atagacgaac ctttaaaaga acgattgcaa tctgaagagc taattctaaa    540
tcgctttctt caatatcagc aaatggtgta tcttctaata ctttataaac gatattatta    600
tatttgaata aatcgccttt attgagagtt aatttagact cttctgttaa ttctgtgatt    660
tgttctcggt ctacgtatcc agcttcgccg gcgtaagtag caccagtttt aaatgtaaat    720
tcgttatctg ggttaaggta tttgatacca taaaaagcag caacaggttg attagttctt    780
tgcgttgcta caatgtcaga atatattaat ttagtggtag cgcgagtcaa agcaacgaga    840
tttgggcgac cgattgagtt gctattcgtt gtggttgatt cgcgcagaag ttcgttgatt    900
ttagccattg cgctttcctt ttggtttata tgatttattt ataccataaa aacaactaaa    960
gggacccgaa ggtcccttaa atcgtcaaag attagatacc tttaacatat acacggcgga   1020
agtaagcgtt tttaccaagg ctattcagaa tagaaggcat accgctctgg atgcgagaag   1080
ccggagcctg agcagcggat tctgcaaatg ggttgatacc gataccgtaa cgagttttga   1140
atcccattac tggttggaag ttcttcggat cggaaccacg cagcggagtc agagctacat   1200
atggagcgta gtaaatacca gcatccattt cgttcggacc tttataacct acagtgaaat   1260
aatcctgttt agcatactgg tcgatatata cacggtattt accacccaga acaccagcaa   1320
atactgactt ggtagtatca gtgttaaagc cggtagccag accctgtgca gcataagaaa   1380
tgccagtatc aactgaagcc agaacgttaa ctacgttacg ggaagcgata atgaagttac   1440
cttcaccacg accggtctga cgagcaattt caactgcttc tttgtcaatc tggaacaaca   1500
gagctttaaa ggattcacct gcccagcgag caccacgaat gtcaattgga tcctggaagt   1560
cgaatacgcc agctttagaa cccggagtca gggtcatacc agatttacca acctgagctg   1620
agtagttaat ccaatcaaca acttcacggt tgatttccag cataatttct gtagccagaa   1680
tgccagacag ttcagcatca gcatccatac cgtgaacagc gcggaggtct tgtgctaatt   1740
caatagagta agcagctttc agctggcgag atttagcttc gataacttgt ttatcgatac   1800
ggaagcccat ttcattccat gggttatcgg tagaaccgtt gaaaccttcc tggagttcag   1860
cgatagaagt agccatacct tcagcgattt ctaccagtgc accagcttcc atttgtttct   1920
taatttcagc atctaattta tctgcatcag ttgcgcttga actaattgtt actacagcgg   1980
aagcttgcag atacacagta ccagtgtcct ggaagaagtg agtatagata tcacctgctg   2040
tggtttgtgt gctagcagcc agagctggga atttcttagc agcaccctga ccagagaaca   2100
ttgcatctgg accatacatt gggtggaatg cttctttagc accagaagcg accgggtctt   2160
taccgtatac tgcacgcagt gcgaatacct ggccagtcgg gctgttcatc ggctgaacac   2220
cacaaatatc gaaagcaatc aggttaggaa tagcacgacg taccataccc ataacagctg   2280
ggccaatctg agttactgcg ccagaagtct gacctgcagc gatgttggta gcattgtaac   2340
cgtggtcacc accgatttca gcttctgtta agaaagaacc gaatgcctga gcaatttttt   2400
```

cgtctttata ttccggagct gtctggaaat ctttttcctg gttttcaaag attttagcga 2460
taatcgcttg tttgctatta gcaatttccg gtaaaccttc accttccagt aatggcttcc 2520
atttgttcaa aagttcagct ttagttttga tagtcatttg tgttaacctt taaaattaga 2580
aacgagatgc gactttcgca tatacactta caatatcttc tgcaccctgt gcagctttat 2640
cttctacagc ttcagtgacg aaattcagtc cggctgcttc agtatcagga gtatttatac 2700
cctcagtaat agtgctttca tctttattag acttcttcac catttctacg attgcactca 2760
atttacttga gaatgcatct gaataatcca taccttcgac cagagcagag actttttctt 2820
tttgagactc agtcagatct ttagtacttt cgctcaatgc cacttcacgc tgcacataat 2880
tgatatatgc gtc 2893

<210> SEQ ID NO 16
<211> LENGTH: 728
<212> TYPE: DNA
<213> ORGANISM: Artificial Sequence
<220> FEATURE:
<223> OTHER INFORMATION: partial sequences of Bacteriophage EK88P-1

<400> SEQUENCE: 16
atgaatttag aagcttgctc agcgattttc ttctcagctt tttcttcggc ttcttcttta 60 ttttttttcta cttcttcttc tgctttttca gcaattttag cgatatgaga ttcagctaat 120
ttaacggcgt gctgcttgac ggtagcttcg aatacagtgc cgaaagtttc ttttgcttcc 180
ggagaaatat taactgattc gaaaatacta tcaagagcaa cggaagcatc aattttctgc 240
gcttcggcaa tcagttgttc tttaagcatt ttgtagtcct gttgtttaga taataatatt 300
tataacgctt ttttcatggc ctctgcgaga gccatatagg cgtcatcggc acttgtatcg 360
gcttccgccg tctgtgattc ggtaatttcc ttaggagtta cccatgcatc tggagcactt 420
ggaccccata ctgcatcaac acctacagtt aatttgaatc cttcgtttac gatacgataa 480
cctttatttg tgtcagtcaa tgaacctaat ccacgagaag aaactcctgg aatccatccg 540
gcacgaatat tagctgctaa tttatctcca ggaccatggt caccttcaat aacacgagct 600
cgtccgtata cgtcatttcc tttccaccac atatcttcta taatgatagc ggcttgcatc 660
gggtcaacat tagcgcgtgg aggatgattt aattctccga gagcttgttt agttaaaact 720
tgctcatt 728

<210> SEQ ID NO 17
<211> LENGTH: 3865
<212> TYPE: DNA
<213> ORGANISM: Artificial Sequence
<220> FEATURE:
<223> OTHER INFORMATION: partial sequences of Bacteriophage EK88P-1

<400> SEQUENCE: 17
gtaataaata tatctatatt tatactgagg aaatattatg atagataaag attatattgc 60
agagctgaag gctcttgatg ataataaaga agctaaagct aaattagctg aatatgctga 120
acagtttggt ataaaggtca aaaagaataa atcttttgat aatatcgtta atgatattga 180
agaagccctc cagaagctcg ctagtgaacc tatgccagag actgatgggt tatctattaa 240
agacttaatt aatgctgctg atgctgcaga gggattaaaa tatgacgatg aagaagtcaa 300
tccagaggca gcacttctga ttgattctcc ggttaaatct gacattaaaa ttgaagtagt 360
agaaacggat aaaattcccg aaaataccga tgttttgatt gaagatactc cttttgttga 420

-continued

```
agaaaaattt gaacaggctg tagctgagat tattgaatct gaaaagccgt ctgtatttac    480
tcttccggaa aactttagtc cgaatcttca gctgattgga aaaaatccag gattctgcac    540
tgttccttgg tggatttatc aatggatagc tgaaactccg gattggaaat ctcacccaac    600
tagttttgaa cacgcgtcag cacaccaaac tttatttagc ttaatttact acattaaccg    660
tgacggatca gttttaattc gtgaaacacg caattcttct ttcgtaacat taaaataagg    720
ataacttatg acttttacgg ttgataactc ctaaaacacc tactggagtt atagatcaga    780
ctcagcagtt tactgctaca cccagtggtc aaactggaga tggacctatt acatatgctt    840
ggagcgtaga taatgttcca caagatggag ctgaagcaac ttttaattat gtattaaaag    900
gacctgctgg aacaaaaaca attaaagttg ttgcaacaaa tcaagttgcc gatagtagtc    960
ccgaaacagc agaaattact acgactatca cggttaaaaa taaaactcag tcaactacgt   1020
tggcagtaac tcctgatagc cctgacgctg gagtaatctg aaccccagtt caatttactg   1080
ctgccttagc ttctcaacct gatggagcat ctgctacgta tcagtggtat gtagatgatt   1140
ctcctgtgga cgaagcaact agcgctacat tcaattacat tcctaccaca agcggagtta   1200
aaaaaatcaa gtgtgtagct caagtaaccg cgacagatta tgatgcacta agcgttactt   1260
ctaatgaagt atcattaacg gttaataaga agacaatgaa tccacaggtt acattgactc   1320
ctccttctat taacgttcag caagatgctt cggctacatt taccgctaat gttactgatg   1380
ctccagaaga agcgcaaatt acttattcat ggaagaaaga ttcttctcct gtagaagggt   1440
caactaatgt atatactgtc gatacctcat ctgttggaag tcaaactatt gaagttactg   1500
ctgtcgttac agcaactgat tatgatagca aaacagttaa aacaacaggt caagttcagg   1560
taactgataa agttgctcca gaaccagaag gtgaattacc ttatgttcat cctcttccac   1620
atcgtacttc agcttatatc tggtgcggtt ggtgggttat ggatgaaatc caaaaaatga   1680
ccgaagaagg taaagattgg aaaactgacg atccagatag taagtactac ttgcatcgtt   1740
acactctcca gaagatgatg aaagattatc cagaagttga tgtccaagaa tcgcgtaatg   1800
gatacatcat tcataaaact gctttagaaa ctggtatcat ctatacctat ccataatcat   1860
aaggggcttc ggcccctttc ttcattttga aagcacacaa aacacaatca gaaaatgatg   1920
tatataatgg caccaactcg ataacatgag attgattatg agaactgagg ttgtggtgtt   1980
tactcttcat gagtctggaa agtcattcat tgaaattgct cgtgaattaa acttacaggc   2040
aaaggaagtg gctgtattat gggctcgagc tatgactgct aagaataaat ttgagactcg   2100
agaaaaagtt gtctatagaa aaagacatat caataaaaag gtgaaaaatg gaacagtatg   2160
atctttatga aaatgaatct tttgctaatc aattgcgaga aaaagcactt aaaagtaaac   2220
agtttaagct agagtgtttt attaaagatt tttcggaact tgctaataaa gcagctgaac   2280
aaggtaaaac acattttaat tattattgta ttgctcgtga taaattgatt actgaagaaa   2340
ttggtgattg gctgagaaaa gaaggattta gctttaaagt caatagtgat cagcgtgatg   2400
gtgattggtt agaaattaca ttttgaggat taattatgtt taaaaagtat agcagtcttg   2460
aaaatcatta caactctaaa tttattgaaa aactttataa cctgggattg actggcggcg   2520
aatgggtagc tcgtgaaaag attcatggaa caaacttttc gttgattatt gagcgtgata   2580
aagtaacttg cgctaaacgt actggtccta ttcttcctgc tgaagatttc tttgggtatg   2640
aaattattct aaagaattac gctgattcca ttaaagcagt acaagatatt atggaaacct   2700
cagcggttgt atcttatcaa gtctttggcg aattcgctgg acctggcatt cagaagaatg   2760
ttgattatgg cgataaagat tttatgtat ttgacattat tgtcactacc gaaagtggtg   2820
```

atgtaactta tgttgatgat tacatgatgg aatcgttttg taattcattc gggtttaaaa 2880
tcgctccact tttgggtcgt ggtaaatttg aagatcttat taaacttcca aatgatttgg 2940
attctgttgt tccgtcttat aattttaccg tagataatgc aggtttaatt gacgctaaca 3000
aatgtgtttg gaaagctgaa gtaaaaggcg aagtatttac cgctgaagga tatgtattga 3060
aaccttgtta tccttcttgg ctgcctaatc gcaatcgtgt agccatcaaa tgcaagaatt 3120
ctaaatttag tgaaaagaaa aagtctgata agcctattaa agctaaagtt gaactgtcag 3180
aagctgataa caaattggtg ggattttag cttgttacgt tacactgaac cgagtaaata 3240
acgttatttc taaaattggc gaaattggtc ctaaagattt tggaaaggtg atgggactaa 3300
ctgttcaaga tattttggaa gaaacttctc gtgaaggtat tactctgact caagcggata 3360
atccttcttt gattaagaag gaattagtta aaatggtaca agatgtactt cgtccggctt 3420
ggattgagtt ggtgagctaa ataaaaaggg accgaaaggt ccctttgttt tattcatcaa 3480
cgataatttt tggtagctta acacctaata aaacagacaa atctgaacga cccgccattt 3540
tatccatgtc tccaccgtca attattcttg cttctttttc atcttttgct acggtataag 3600
gatttgctga taaagcatat ctaactaata aaccgataga tggttgtaag ctttctggat 3660
caacaacaac tttaaatgcg cctacatgtt cagggtcatc taagtcgaga ccttctgtat 3720
acggagcata gaaaattgat ccaacaattt ctttttcacc gatattttct actacaccaa 3780
cgattacata atctaatggg ctgttagtat cgcaataaag cggtaaacca ttagctaaga 3840
acccgtaggc attttgtgaa agata 3865

<210> SEQ ID NO 18
<211> LENGTH: 12358
<212> TYPE: DNA
<213> ORGANISM: Artificial Sequence
<220> FEATURE:
<223> OTHER INFORMATION: partial sequences of Bacteriophage EK88P-1

<400> SEQUENCE: 18
ttcaaaaagg caaaagagaa atataacgta atttgttata ttgacgatct cgctcaccac 60
tgcgatcacg cgagtgaaat attaaatgtt cctgtttatt ggatggctcg aggggaacgt 120
gacagtattc caaaaactgc tcagcgagtt tatacatgga acgatgtaga gaataagctt 180
ttttcaccaa aggaaaataa agaaagtttt gatagtgaaa aagctataaa agatgtaatt 240
gaaaagatga ttaaaaacga ttcttttcct tggaacacta cctggagaac tcctggattt 300
aatccttata atccatatca tccatattat acacactcac atcagatgca tccattccat 360
acgtggagtt atattaagcc tggcgatgca gggtatttta atagacttac tagtggtagt 420
gatgataata ttttccaagg agcattttaa tgtttgttgt tcacactatt tatgaaaatg 480
aaggtaatac tacacgtgat tacggtcacg taaatcaatt ttttagatgc aatccagaat 540
tccgagctca aaaagacgaa cgaattttta aaaaaatgtg taaagcaagg tttcatttac 600
gtcaagcact gggtgcaagg aaataaagtt agaaccacgt accacaggtc tttgactgag 660
cttaatgatg tattgattta taatagagct gtaaaccaaa ctctaaagga tgaacaatga 720
ttcttaaaat tctgaacgaa atagcatcta ttggttcaac taagcagaag caagcaattc 780
ttgaaaaaaa taaagataat gaattgctta aacgagtata tcgtctaact tattctcgtg 840
ggttgcagta ttatatcaag aaatggccta aacctggtat tgctacccag agttttggaa 900
tgttgactct taccgatatg cttgacttca ttgaattcac attagctact cggaaattga 960

-continued

```
ctggaaatgc ggcaattgaa gaattaactg gatatatcac cgatggtaaa aaagatgatg   1020
ttgaagtttt gcgtcgggtg atgatgcgag accttgaatg cggtgcttca gtatctattg   1080
cgaacaaagt ttggccaggt ttaattcctg aacaacctca aatgcttgca agttcttatg   1140
atgaaaaagg cattaataag aatatcaaat ttccagcctt tgcccagtta aaagctgatg   1200
gagctcggtg ttttgctgaa gtcagaggtg atgaattaga tgatgttcgt cttttatcac   1260
gagctggtaa tgaatatcta ggattagatc ttcttaagga agagttaatc aaaatgacta   1320
cagaagctcg ccagattcat ccagaaggtg tgttaattga tggcgaattg gtataccatg   1380
agcaagttaa aaaggagcca gaaggcctag attttctttt tgatgctcat cctgaaaaca   1440
gtaaagttaa agaattcgcc gaagtagctg aatcacgtac tgcttctaat ggaatcgcta   1500
ataaatcttt aaagggaact atttcagaaa aagaagctca atgtatgaag tttcaggtct   1560
gggattatgt tccgttagta gaaatatacg gtcttcctgc atttcgtttg aaatatgatg   1620
tacgtttttc taaactagaa caaatgacat caggttatga taaagtaatt ttaattgaaa   1680
accaggtagt aaataaccta gatgaagcta aggtaattta caaaaagtat attgatcaag   1740
gtcttgaagg tattattctc aaaaatatcg atggattatg ggaaaatgct cgttcaaaaa   1800
atctttataa atttaaagaa gtaattgatg ttgatttaaa aattgtagga atttatcctc   1860
accgtaaaga ccctactaaa gcaggtggat ttattcttga gtcagagtgt ggaaaaatta   1920
aggtaaatgc tggttcaggc ttaaaagata aagccggtgt aaaatcgcat gaacttgacc   1980
gtactcgcat tatggaaaac caaaattatt atattggaaa aattctagag tgcgaatgca   2040
acggttggtt aaaatctgat ggccgcactg attacgttaa attatttctt ccgattgcga   2100
ttcgtttacg cgaagataaa actaaagcta atacgttcga agatgtattt ggcgattttc   2160
atgaggtaac tggtctatga aagcttactt agaaacaatt gtcattgctc aaaaagaagg   2220
tggagatgtt tctacttctg tatcacaagt cattctcgaa tttgtagatg cgtatgctta   2280
taataaattt acagaaacat ttgatgccta tgaaaaaggt ccaaagtttg aaatatatcg   2340
tactctctta ccactagatt attaaaggcc ttcgggcctt taattttata aatagaataa   2400
acactagaga ggatatgatg gaactaatta cagaattatt tgacgaagat actactcttc   2460
cgattacaaa cttaaatcca aagaagaaaa taccgcaaat tttttcagtt catgttgatg   2520
acgcaattga acaaccgggc tttcgtttat gtacctatac atctggaggt gatactaacc   2580
gtgatttaaa gatgggcgac aaaatgatgc atattgttcc ttttacatta actgctaaag   2640
gttcaattgc taaattgaaa ggtcttgggc caagcccaat taattatatc aattcagttt   2700
ttactgttgc aatgcaaaca atgcgtcaat ataaaattga tgcttgtatg ctccgtattc   2760
ttaagtctaa aaccgctggt caagctcgac aaattcaagt tattgctgat agacttatcc   2820
gtagtcgttc aggtggcaga tacgtccttc ttaaggaact ctgggactat gataaaaagt   2880
atgcatatat tcttatacat cgcaaaaatg tatcactaga agacattcca ggagttccgg   2940
aaattagtac tgagctcttt actaaagttg aatcgaaggt cggtgatgtt tatatcaata   3000
aagatactgg agctcaagta actaaaaatg aggcaattgc agcatctatt gcgcaagaaa   3060
acgataaacg ttctgaccaa gctgtaatcg ttaaagttaa aatttcccgt agagcaattg   3120
cacaaagtca gtcattggaa tcttatcgta atgaaagtga attattccag aagtatgaat   3180
ctactgcagc taatttcaat aaacctgcta ccgctccttt aattcctgaa gcagaagaaa   3240
tgaagcttgg aattaattca ttagcttcta aaactaaggc agcaaaaatt attgccgaag   3300
gaactacaag tgaacttcgc tattactata aattcgtttc aaaaagtgag gttgatgagg   3360
```

```
tttctgaaaa aattaaagat gtaattctta atgcgatcaa aaatgaacca actacttcaa   3420
taaaatgttt agagaaatac gcagcagctg ttaatcaatt ctttgaagaa tataaagata   3480
aatggcttga tacacataat aaaacccgca aaggacagcc agatgaagtc tgggaagaaa   3540
taactaaaaa ttgctggaac gcagcaaaaa ctgtattcct caaacgaatg atttatagtt   3600
tttctggaat tggtgcaggt ccaatgattg atattactat tgcccgtgat ggttctaaat   3660
ataccccatc acaaaagcgt ggcattagag agtattgtgg ttcaggatat actgacatca   3720
ataatcttct tttgggtcgt tacaatccag aacgatatga tgtaatgagt gaaaaagaaa   3780
ttgaatctgc cataaataac ttagattcag cttttgaaaa tggtgaccgt ataccggaag   3840
gcattacagt ttatcgtgct caaagtatga ctgctcctat atacgaagca ctagttaaaa   3900
ataaagtgtt ctatttcaga aattttgtat ctacttcttt aactcctatc atttttggac   3960
gttttggaat tacacatgct ggtattggtc ttttagaacc agaagttcgt aatgaattga   4020
cagttgataa aaatgaagaa ggaataacta ttaatccaaa cgaaataaga gcgtataaag   4080
aaaatcctga atacgttaaa gttcaaatag gatgggcaat tgatggagct cataaagtta   4140
atgttgtata tccaggaagt ctaggaatag caacagaagc tgaagtaatt ctaccgcgcg   4200
gattgatggt caaagttaat aaaataactg atgcttctaa taatgacgga acaacatcta   4260
ataacacaaa actcattcaa gctgaagtta tgactacgga agaactcacc gaatcggtaa   4320
tttatgacgg tgaccgtcta atggaaactg gtgaagtagt tgcaatgaca ggtgatattg   4380
aaatagaaga cagagttgac tttgcatcat ttgtttcatc aaatgttaaa caaaaagtag   4440
aatcatctct tggaattatt gcatcttgca tagatattgc aaacatgcct tacaagttcg   4500
ttcaaggata aatcatggaa cttattacag aattatttga cggcgcttcg gcgccggttg   4560
ttaacttaaa tcctaagcat aaaatacctc aaatttttgc tattcaagcc ggtgaagaaa   4620
gcgtgcttcc tggatttaga ttttgtacat acacctctgg cggtgataca aataaaaacg   4680
ttaagccagg cgataaaatg atgcatgtcg taatgatagg tgttaatgag aaactatcat   4740
tagttaagct taaaaacttg ggtggaaatc caattggtgt cattaatgct gtttttgata   4800
ctgctcttca aacaatgaaa cagtataaaa tcgacgcatg cctattacgc gtactaaaaa   4860
gttcaaaatg tagtttacaa gtccctcgtg ttgtgttata gtagtcttac tgacataaca   4920
tgaggaacac aaaatgaact cttctttacg ctttttaggt caagaacttg tagttgaagg   4980
cgttattcct gctgataatg cttttaacga agcggtttac gatgaattta ttaaaatttt   5040
tggaacagat aaaaagttca gaatttttcc ttctgaaaat ttttcaaagc cagaacagac   5100
tgaaagtatt tttcagggtg tagtaacagg taaatttgag tcagaagctc cggtaaaaat   5160
tgaagtttat attgaagaca gtttagttgc ttcagtttct gctttcattt cattccgcaa   5220
ataaaaatat ggggaccgaa aggtccccgt tgttatattg ctcctaatat tttactctgc   5280
gaattgacaa tccctgtcat agtatactaa tatttgaaat gcttcctgag gttcctccta   5340
gtctactaag tcgtgaaagc gaattagata gtccagtgac acctccacta tttccgagaa   5400
cgctttgaat accatttata gcagcagatt caagccattc aagcgcagct tgcctatcaa   5460
ccgctccagc ctgcatcact ctatacgcaa aagtaacatc aaatgtagtt atttggttat   5520
ctccatcata tgataactca ggagcgctca ctgatattgg aatgcatcca gtgaacatca   5580
ccgcagtatg aggcaatcca ttgcgagaat gaagattaac ctgaatatct gcctcgacat   5640
cttgcggcaa agcacgcagt ccagttactg ggtcttgaac agagttaacc cagtcttgca   5700
```

-continued

```
ttgcacgata gttacaagct tctgaatcca ttctaaatga aataaccaaa gggtctaatt   5760
ctctcccagt tatacgaata ttaggagaat tatagttcca gtcagtttca taggataatc   5820
tattctctgg catttttaca gagtatatca tcaatccaga tgagttatat gccatgttaa   5880
agaagtcaat taaatatgta ccaactgtaa atgagcctaa taaactctgg acagtacgtt   5940
gactcatggc accaataaga tatttactaa cccctgattt tcttatcagt tttgtgtgc    6000
cagctgtaat tagcgtggta attccctgat taatatcacc ttgagttaat cctaaccaat   6060
ttgaatttag gcccaagtta ttataagaaa agttgctaat tgaacttatc aacgaagagc   6120
ttttagttga tggagttgtt gcaaaaaacgc agctaaacat attattacgt tggaaatctg  6180
cgtttattgc ttgattatta aattcctcta aagaatacat taaaaagtcc ccgcatataa   6240
agaagcacgg tttaacgtga taatttctct catagtaatc tcgagagtaa atgtactagg   6300
gaggtttgga gcaatagcta atccgttaaa gttaccatta ggtgttttat caaatctaat   6360
gctctgtatt tggcatggac caaatatttc cgtttttcca tcaaacttag atgttgcacc   6420
aaagtttttc accatccaaa ctgtcgggtt tgaaactaca agaacgttcg ttaaacttgc   6480
tgtcattttc tcaaatagtg ttttattttt agctgcgtct tccggagata aaggttcaat   6540
taacgtagaa cgataccaat catctaaata cccctttatt tcagcagcgt attgagattt   6600
acctgtttca ccataagaaa aatagttaaa atattgatag atattaataa tagccattaa   6660
atcttctgtt gaacgtggag tcaaatccca tgtaaacact ttagttctat tttcagcacc   6720
accatacata cttctggctg tcgtataaat ctgttcatta ttatcagcca ttataccttg   6780
tgttatactt tccagtgccc caaatactgc ggttgaagca acattactta gcacaccagt   6840
agcagtacct ccgcctctac tgataaggct ttcttgaaca tcattaaatc tatgtgatga   6900
tgtgtcaaca tcagatttag atctcggtaa aagaatgttt gcgacaggag ctttacttat   6960
tgttcctgaa ttattatttg atattaatcc atttgatagt tttgatactg tactactaat   7020
agtgtttcta gctgtactta aaatactcga agatgaagaa gagtagttag atctcatcga   7080
tctaagactt ccagaatccc tagatgacat attgtatgca gtaaataata atccattctt   7140
atatagatct gttacctgga agtcccctgt agtgtcatta ccactagcac gcccagttgg   7200
aaactgggca gtgtatgttt tagttactac ttctgattta gtgctctgtc cggctgaaat   7260
tttctcaccg gactttttaa ttaaatcagt agtcatttct ttaacaattg ccatattatt   7320
ccttaattaa ctccagtcgc atcaaataca ccaggagcag ttgtgcttgt gacaggtgtc   7380
atattatgaa cgacagtatt tttcttaata acattattag tattattgat tgaaggagat   7440
gcttgctgaa caggagcttg ctgtgctttg ttcttttcaa taacctggac ctgtttcgct   7500
tctggcgatt tagcagaagt ttcaggtttg gcattaggct gatttttctt gagctcttga   7560
taagtagcat caattttaga aaatctagca gcaagttctt ttttaactgc cggtgaattg   7620
tttaaatccg ggtcatccat ccgtttttta aggtcttcat aggcagattc aactgattta   7680
accgttgagt ctttactcat atcagctgaa tcagcatatt tttcaaaacg aatcatcgcg   7740
gcacgtgctt cattagcctt cattaaagca ttttttcttt cttcaggtga aagctgcttt   7800
aatttttctt cttctgctgc acgttcttcg tcggtagtta gtgcttcttt attatcaaca   7860
ccgcgaatcc aattagatgc acgagttttc cagttcgcaa ttttatctaa tccttttgct   7920
atcggaccaa ggtctccgtt cattcgttta tcttgataat ttgcaacttt ttcttggtct   7980
tctttattga gagatgctcc agtagaattt tggaaatttt ctaatgctct tccttctact   8040
tcatcagcgg tatccttcat accaggaatg actcgaagaa ttgcagcaga taatttagcc   8100
```

atacctaatt gaataagttc tcctaaatta taaagaacct ttccaagccc ttcaacaata 8160
gctactgtca atccacccca atctcccgct tcccagaact ttttaatttc atcaatagaa 8220
ctaaagatgc tctgtaataa aggaccccaa gttccggttt cgctagagaa tttagtaaag 8280
tcagtactaa acaaatccca agcctgcgaa aatttatctg accaatattt aaagtgaacc 8340
atcagaagat ctattccaac aacaacagcc aatatcattg cagtcatttt agcggcttca 8400
atagcagcac tgacggtgta cttaaatagc atgcttgata ttttatcagt aattgaaata 8460
gatttcttaa atccaaaatc aactgtcttt gttaatttat ctaaagcttg agataatttt 8520
aagttaaatg cttctttttt ctgtttttct tctggtgatt cttgtttggg ttcaactggt 8580
tgaggggtag ggaaaaaatc agcgtcagga tcattattaa ctgcttcggg agctggtaat 8640
aaaggaccca cagattcagc agtatcatcc tcaacgactt taacaggaat agcgctttca 8700
accgtggcta aactagtccc agtctgttga attccagctg tctgaatttt ttgttctaat 8760
aaactcgtta atttatctaa tttgcttccg agtgattcac caatttcttt attaatattg 8820
ttgccaattt cgacagtttc agcaattaac tcagaaccgg cagtagtatc actcactgcg 8880
ctttctacgt tatcaattgc tccaattatt tcattcgatt tttcttcgac agtttgagct 8940
attaattcag aggcagcttg agcatcatcc aatttcgtag atatatcatt aagtccagat 9000
aaagtattag aagcggattt agccgcttcc tgtgttggtt tattatctga aataactttt 9060
ctacgcatcg tttgcatttc ttgtggcttt ttcattcaaa taatccaata atattgccaa 9120
ttccagttat tggaccatta gggccaggaa ttgctaaagt tgtaaaaata tcatttgccc 9180
attttaaaac gaatgctggc atctcaagaa aattaatttc tttaacttca tcattgacct 9240
taagcaagca tttagataac atatcgctca ccgttaaaaa ttgttcaaat tttccaggag 9300
gtctaaaata aaatgtattt ccttggtatt gaaattctaa tctttggcat acatagacat 9360
cattaatgtc ataagtatag ccatctattt ctttacgaga tttaatcttt ccattaaatt 9420
ccaataaatg aatagaaacg aaatcaactt ctgccggtga taaattcgga caaatagaat 9480
caataagaag ttttaaattt tcatcaggac ctttaacatc ctttaaaatg ttataatgtt 9540
taagacccat tttaggaata gaaacttctt tattacttat tggaagaact actttcttca 9600
gtggtagtat cagatttaaa ttcattttta accttaactg ggtctattgt ttccagtttc 9660
gttgcattag tgaacatata tagatgagtt actgaattat tattggataa ttcatggatg 9720
acttcatcaa cgtaaaattc tgttttaaat tggtttttac tatcattaaa aataatttta 9780
acgccaggtg tcaagttaaa attaccgaca gtagaacatt tagcatagcc atcatattgc 9840
gccatagttt gaagacgaat agcttcttca tagccatttc tataagtcat ttcagaataa 9900
gcacctgacc ttgacactac aatagagttt tcaccctttc ctgtagtaat cattggcagt 9960
gaagaatcta aaaacgaatg agcatagata gtagcatttt tcattgggtc acgtttgtga 10020
ggattcgatt tagtcaacca aacgaaatca tatgctaatg gatattttaa ttcttggacg 10080
aattgaccta ttaaagttgg ctcacctaca atcattggat atggttcttg atttatcatc 10140
atatcatagt ccatcatgtt aactcccatg atgtcttgcc atacaaatac aaatttgtcg 10200
cttcctacag ctagagcaac ttctcttaca tatgacaaat agttttcaaa tgtgctagtc 10260
catggaatat caggaacata agcatttata gcatttattg gtggagttaa taatgtgcga 10320
tcctgataaa ttacgccaag catttccttt atagattcac cggcatcagg gaaaaatggt 10380
ctaccaaatt taagattttc tatagaatga atagttccta attcaatagc aatgatgtta 10440

-continued tcacctttg aatctactga cacggaaaaa tgcttacatc cataaattcg tgttttaaca 10500
ttattaatat catttgcatt agctacagaa atctgaatta tttcatttcc atccattttt 10560
gtatggatgt ttttagaatc ataaaactgc agcattcctt catttcgacc ataaagagaa 10620
tcacgcatag ttaatgtagt aatagtagca gctaattcaa caaatctatt attactccaa 10680
gcatcgtaac tctcaaataa tttaacgctg agatttggat atccggggcg ttgcaacata 10740
ctcattattg tttatccttc tcaatcagtt ttaatacgaa tccgcgctcg gcaggaatca 10800
ttttcattat tgaatttaag ctataattac tttttacaag cgtgtgatta atttgataaa 10860
aagtaaatat ctcatctgga ttaactaata gcttaaacac atctactata tcagtgtatt 10920
ttttaatgta cttatcacaa cacgacatgt gcaatgttaa attaatagga ttcattgcat 10980
cgagaatttt ttctaatgtt tctatctcga tggcgtcaac aagttctatt tgacttgatt 11040
cactaatttc cttccaatca taccacattt catctacttg aacagaatga atattttcag 11100
taatcatctt tgctttattt tcataaaact cagaaggaaa ctttaattta attttaacat 11160
tagctacatc aaaaacaggt tcctttaatt ctttttgata tatttcaaat ggaactgtct 11220 tttcttttt acattttgga catacgaatg tgactggtac ttttgtttta cctattgacc 11280
ctacaaatac ctgcaaaaat ataaatggtt gccaagtctt tggatagtct ccaaaataat 11340
cagcaattaa atcagcaatt acttcttttt gttcttgtgg tgaccgatgt tctatatcgt 11400
ttcgaactaa caaaaaatct cgataatctt ctaccgtaaa tggtttaaaa cgatgaacac 11460
catctggtaa tttacaacga ataatgtttg ccatagatgc tccttttatt ctatttataa 11520
atatgataaa taaaggagct aaatatgtat gaatacaaat ttgatgtgag agttggttct 11580
aaaataatca actgtcgcgc atttactctt aaagaatatc tagaacttat tactgctaaa 11640
aagaacggtt cagtagaaga gatcgttaaa aagctaatca aagaatgcac aaatgcaaaa 11700
gatttaaacc gccaagaatc agaactatta ctgattcatt tatgggcaca ttctcttgga 11760
gaagttaatc acgaaaactc ctggaagtgc acctgcggaa ctgaaatacc aacccatata 11820
aatctattac atacacaaat agatgcacca gaagacctct ggtatacact gggtgacatt 11880
aaaattaaat tccattaccc taaaattttt gatgataaaa atatagccca catgatagta 11940
tcatgcatag aaacgattta tgctaacggg gaaagcattc cagttgaaga cttaaatgaa 12000
aaggaactag aagatttata ttctatcatc acagagtcag atattgtagc tataaaagat 12060
atgcttttaa aacctaccgt ttatttggct gttccaatta agtgtccaga gtgtggaaaa 12120
acccatgctc atgtaataag aggcctcaaa gagttctttg agttactata atggcaaata 12180
ttaataagct ttattctgac attgacccag aaatgaaaat ggattggaac aaagatgttt 12240
ccagatcact tggattaaga tcaattaaaa acagtctttt gggaattatt acaacaagaa 12300
aaggttcaag accgtttgac cctgaatttg gatgtgattt atcagaccag ctttttga 12358

<210> SEQ ID NO 19
<211> LENGTH: 3307
<212> TYPE: DNA
<213> ORGANISM: Artificial Sequence
<220> FEATURE:
<223> OTHER INFORMATION: partial sequences of Bacteriophage EK88P-1

<400> SEQUENCE: 19
agagtataat gcttcacgta taaacgtggt ataatgaatc taagtccatc caataacaat 60
tgaatagaga acaatatgag attagaagat cttcaagaag aattgaagaa agatgtgttt 120
atagattcga ctaaattaca gtatgaagca gctaataatg tgatgttata tagtaaatgg 180

```
cttaataagc attcaagtat taaaaaggaa atgcttagaa ttgacgcaca gaaaaaagtt    240
gctcttaaag ctagattaga ctactactcg ggacgaggag atggtgatga atttagtatg    300
gatcgttacg agaaatcaga aatgaaaaca gttctatcag ctgataagga tgttttaaag    360
gttgatacct cgttacagta ttgggggatt ttattagatt tctgtagcgg agctcttgat    420
gctattaaat cacgtggatt tgctattaag catattcaag acatgcgagc atttgaggct    480
ggaaaataat gagatatagc attgatgatg cttttaatta tgaagaagaa tttgaaacgg    540
aaattcaatt cttaatgaaa aagtataatc ttaagcgtca ggatattcgt atcctggccg    600
atcactcgtg tggtgaagat gtcctttata ttaaaggaaa atttgccgga tatcttgatg    660
aatattttta ttctaaagat atgggcattg atatgcatat gagagttgta taaatagata    720
tataattcag aggagacaat catgtcagat aagatttgtg ttgtctgtaa aactccaatc    780
gattctgcat tggttgttga aacagacaaa ggtcctgtac atcctgggcc ttgttataat    840
tacattaaag aactaccagt ttcagaaagt tcggaagaac aattaaatga aacacaactt    900
ttgctatagt gtgaccttta gtctatagtt ttggcccttc ctttttggtt gggccttttt    960
taatttaaaa gctttcttct acttcatcgt ctgaatcttc taattcagct ctttttcctg   1020
ccaaagcatc tctcacagag atgtcatcag tatcttttaa ttcagtttct ttgactcttt   1080
tcttgtaata agcttcaagt tcttctaaac cttctaatgt ttgacaagag gcaattttac   1140
ccataaattc atcaatagaa gcttcataaa gaaattgttt aaatcctagt aacatctttt   1200
tctccaaagg gccgaagccc ttataaatta actgtttttc taagtattct tagtttgtac   1260
attgataatc cagtagcttt agaagcatct ttcatacatt tatatttaac accatttact   1320
tctataggtt tagcagctgg gttattagct cctgaattat ctggcatgtt atctttaatt   1380
ttctgaatag atttagcaga atgtttcctt ccatacatgc cgttattttt acccgattga   1440
ttgattgaat gtaatctttt agcttcttca gtccatttcg ttgggttcat tcttttagtt   1500
ttactaattt tatttcccca tgtaattgga cgacttttca tgagttttga catatattgt   1560
ttatgttctt ccgtatggtg ttttccgtaa aatggattac cttcgccgga ttgaagttct   1620
gccattttac gacgttccca tgcgtaagat ttattaacgt gtctttcatg agtatttgaa   1680
ttcatcccca tacatataac agctttaatt ataccgtaat ggtttggatg aattttagct   1740
aaaagtttat gggctataaa atgttcttca gccgttagtt ctactaaatt acacttatca   1800
tttgtaccac ccatacatct aggaattata tgatgtgttt cagtgtatcc attaaggcga   1860
gcccgattct gggctctatt aattaaatta tcatatatta atttataatt caaagtttaa   1920
cctctttcat cacataatta aacttttcat cagcataacg ctgaatacga tcaagtccat   1980
gttttaaaag atagtttaaa tgcgagtatt ttttagaaga tgtttttgat ttagaaacta   2040
cgcccgcgtc atctatgagg tcccagactg ttgcgattgt tttagaacca tgcttacgta   2100
atacacgacc gattgtttgt aatacaataa tttttgattt aacgccgtgc gctaaaacaa   2160
catgatgcag atttttaact gaaataccag tagaaaatac accataactc gctactataa   2220
ttattccttt accattttca gctaaggttt tcattacgtt gcgggtttcg gtatcaactt   2280
cccctgatac gtaataaact ttatcgtatt catttttaat taaatcgaaa atagctttac   2340
catgtgatac atgtttaaac atgacaaaag cgttttcatc tttttgcgca agcttaatag   2400
ctaatttagc gatccattta tttcttttac taagccccgt aataattttt atttcttctt   2460
gataagtttt tccctttaat ttagtagtga actcatcggg atagcgaaga aaaatactat   2520
```

```
taatttttaa ctcagttact tgtccatctt ccattaattt agaggtcgtt actggcttaa   2580
atatttcacc gaacattcca acatactgca tgatattggc tttgccatca cgtaatgaac   2640
cagacaaacc aaatttaaac atacagttat ttaaacctga tatgatagat gaaatacttt   2700
ttcctgtggc aagatggcat tcatcattca tcatcattcc aaactgtgag aaccattctt   2760
ttggctgttt tactacagtt tgccatgtac caacaacgac tggtgcatca tttttatatt   2820
tatcatcttt tgatgctccg ccaccaattt tctttatcat tgcatgactg aataaacgat   2880
agtcaacaaa gtcatcagcc atctgagttg tcagagcagt tgttggaaca atgataagaa   2940
ttttaccttc ataattttcc aaataatacc gagcgagcaa agcttgaatt aaagatttac   3000
ctgcggatgt tggaagatta agaattctac gacgattaac taatccttcg aacactgcat   3060
ctttttgata ccaatgcggt tcaattcttt tatttcctga atagatttct aatttagaaa   3120
gccattcatc aaaatctttt cttgataatt cttctttttc gttaatttgt gggtcaatcc   3180
aggctttata gccaaagtta tcacagaact ttttaatttg cccaactaag ccgaacggaa   3240
gaaggcgatt ataatctaaa agacggattc gtccatccca gttgccatat ctgaagcgag   3300
gattaaa                                                             3307
```

```
<210> SEQ ID NO 20
<211> LENGTH: 2793
<212> TYPE: DNA
<213> ORGANISM: Artificial Sequence
<220> FEATURE:
<223> OTHER INFORMATION: partial sequences of Bacteriophage EK88P-1

<400> SEQUENCE: 20

aacttaaata tgctaagcct ttggcttctg ctgcacgaaa agcagttcgt cactttgtgg     60
taacactgaa gtaattcatt ggagattcac tgccttagtg tgagctaaaa tcgaggagcc    120
gtcgaactgt ctgattaatg atttgcgaat cattatagtt ttaagacccc ggcagtttta    180
cggtgtacct cttgaatgtg aatgatgacg ggtttatggt tatcctggtc gttaaatatc    240
caaaaaccta tgttcccctt gagggcttgc gcaggcaatg ccaataagtc ctgcattttc    300
atttaaaaga gaatttataa tggcaaaaca agctaaagca aagaaagcag ttgaaaagaa    360
agttggtgat tctaaacgcg ctggctacaa gcgtgggtcg aactctcgta tcaatcaaac    420
tgttgagaag atcatgcgcc gagcacgtgc ggttcttcga gatgatgctt ctcgttttgg    480
taagcagaaa gcataagtta aggactcctt cgggagtcct tttttatttt ccaaagattg    540
cacaaagttg tttacagtat ggttcctttg tgatagtatt atcttacaca aacaaaggag    600
aataaaatga aaacgattaa tctgaacgct acagttaaaa ctaaatgctt caatggtaaa    660
tatgatgaaa ctatgtggtt cttaatggca gttgaaggtg atattattga agtagaaaca    720
acagaaggta tgggaacaga tttcaccttt acaattcaag ttcataattt ctttactggt    780
tggatttatg aattgaatac agtaatcgtt ggaaaaaattg aacaaaatga attaggtgaa    840
tggtattatg ttacagctcg ccaacgtgcc gaacgcttaa ttgagaagat gaaaaaagtt    900
ggtaaacttg acatgcagca ttggaaagta gtaaaataat tgtttacttt ggtacaggat    960
atgatattat atacctgtac cgcaattaaa catctcggag aataaaatga actacatcaa   1020
ctttgaacgt aaatatgttt ctaacggtat tgcaggttct attgatacta tttgcctttg   1080
gaaacatcaa aatggatcag tatgcgaaat tgaacagtat atgactccta actacgttta   1140
tatgcgattt gaaaatggca ttacggtttc aatcacgaaa gaaggttctt cttttaaaat   1200
cgcattagat gatgattttc gtcaacgtga tttagggact catccttgct ggaatggcgt   1260
```

```
taatcgtaag cttctggtta aaacttggat tcgtcatatt ctgagtaata gagctaaacc   1320

tgagcatctt gaagcaatct ttgatgtagt tcttaacgaa tttgatattt aaaataaaat   1380

gaggggcttc ggccccttac tgaggaaaat actatgttta tgactactta ttttgatacc   1440

cgcaaaaatt tctgtgaagt ggttttctct aaggcaccta aagaccttcc tgctcatttg   1500

cagcctacta gtgaatcgat taaaaattac gttaatgcag tctgcccttt agagttccgt   1560

actgtaaatg gacgcgatac tttagctatc actaaactca atcgtgaaat tgacattgac   1620

ccttcaattg cgcgcgaaat taacatttct gatatcggcg gcggtaatgt taaatcacac   1680

ggttttcaga tgagatttta ataaaatgtt taagaaatta atccagaaat tactgggcac   1740

ggaaatggtc gaagttactt atcgtgtgac tgatgtctct ccgctcactg aagaccattt   1800

agagccatat attatgacaa ttaaaatgct taaacatgat ggcggattat ctattgaaga   1860

ccgtttacca agttatggtc attgggctga tattgaaatt ataagtatta aagatgtctg   1920

agttagagat tagaagcaat tttagatggc catcatgtgc attaagtaat ttcgcccaat   1980

ggccttttgt tatggacggt atccaatttg gaggtctcga aggattcctc caaggatgca   2040

aggtgaaaaa tgttgaacaa cagcgtcgta tatttgggtt atccgggctt gccgcccaac   2100

aagctggacg agcttatgct agagctcagg accgtggcac gttgttctgg cttggaactc   2160

cgttttcaag atattccgaa gcatggaaag aattatacac aaatgcatat tttgaagcag   2220

cgatccaaaa caggggcttt cgcgatgcat tacaagcctc gaaaggaaaa gttttgaagc   2280

acagcatggc tagtggtcta acaaaagatg atacaatact aaccgaagct gaatttattg   2340

atgtgttaaa tctattaaga gactctctat gaagcctact attttgactg atattgatgg   2400

agtatgttta agctggcaat caggccttcc ttattttgct cagaaatata atcttccgtt   2460

agaacatatt ttaaaaatga tccaagatga gaaatttatt tctccaggta aactatttaa   2520

ttgtgatgaa gaacttggcg tcaagttaat tgaaaaatac aatcgttcgg attttattcg   2580

ttacttgtct ccatataaag atgccctgtg tgtgattaac aaattaaaag aagattataa   2640

ttttgtagct gttacagcat tgggtgattc tattgacgct ctgttgaatc gtcaatttaa   2700

tttgaatgct ctttttcctg gtgccttctc agaagtaatg atgtgtggtc atgattcttc   2760

aaaagaagag ttattcaaaa aggcaaaaga gaa                                2793
```

```
<210> SEQ ID NO 21
<211> LENGTH: 455
<212> TYPE: DNA
<213> ORGANISM: Artificial Sequence
<220> FEATURE:
<223> OTHER INFORMATION: partial sequences of Bacteriophage EK88P-1

<400> SEQUENCE: 21

ttactgacat aacatgagga ctttatgatg gatttgcagc ttattactac tgagatggtc     60

gttgaagcat acggtgatac tacagatggg atttctgtat ttaaaggaaa tcgtcgagtt    120

ggatatatca ccgatcttaa gaaagattta gctaagcaag tcaagcggaa aacgaccatt    180

aaagaatatc gaaatcgtcg tcttgagcaa gcccgtgata tgcttcctga tgcggttgag    240

gagatgaaag tctttttaga aaatcagctt gcgaaatatg attgtgatgt gttcattaat    300

cagactcaac ctaatgttca tattaacaac tgtaaatgct atatcatcgt taatcctttg    360

acgggaaaac atcgtcttgg aatcagtaat ccaaatcgta gcgcatcgga tatggcagaa    420

gatgttgagg catgctttaa aatttctaaa tctcc                               455
```

-continued

<210> SEQ ID NO 22
<211> LENGTH: 4455
<212> TYPE: DNA
<213> ORGANISM: Artificial Sequence
<220> FEATURE:
<223> OTHER INFORMATION: partial sequences of Bacteriophage EK88P-1

<400> SEQUENCE: 22

```
aattcagtat aattatattg atgcgatgaa taataaaaat cgtgaggcaa ttgctgctat     60
tgagcgtgaa aatgaaaaac tgcgcaaaga cgcaaagaag gcggatgtgg tggctcataa    120
gccaggattg gttgaaaaac aaatcaacaa ctccttcaac aagttcgcag aagacatcca    180
ggacctttct aaatgattaa attatcagca gtaatattat ctattggtct tctagttggt    240
tgttcgacaa agcctctaga agtaaagaaa gaaacagttc atcctaattg gcctgtacaa    300
ataaagtcat atgacgaagc taaattatct tggcaagtta aagttattga tggtaaagct    360
tgggttggta tgccatttga agattctcag gaatttcgta tttggcttaa tgatgtaaaa    420
cgatatgtac atgaccaaaa aactatgata tgttattatc gtcaagagtt aaaagaggat    480
aaatgtaaat gatttcatgg catcaatttg aacatctcaa aggattgatt tatgaatccg    540
agatggctgc aatgatttat ggacgccaga ttcagcggtt agaatcttta cctccaacta    600
atgatgtttt attagctcaa tcacgtgcta atctcaaaaa tgaatatcaa aataagtggg    660
gtaaagcatc taaagaccta catgattata ttcaatcact ggttgagaaa aaataaatga    720
aaaagattat tttgactatt ggctgtcctg gttctggtaa gagtacctgg gctcgtgaat    780
ttattgctaa gaatcccggg ttttataata tcaatcgtga tgattatcgt caatccatca    840
tgggtcatga agaacgcgat gagtataagt ataccaaaaa gaaagaaggt atcgtaactg    900
gtatgcagtt tgatacagct aaaagtattc tgtacggtgg tgattctatt aagggcgtaa    960
tcatttcaga tactaacttg aatcctgaac gtcgcctagc atgggaaact tttgccaaag   1020
aatacggctg gaaagttgaa cataaagtgt ttgatgttcc ttggactgaa ttggttaaac   1080
gtaactcaaa acgcggaact aaagcagtac caattgatgt tttacgctca atgtataaaa   1140
gcatgcggga atatctcggt cttccagtat ataatgggac tcctggtaaa ccaaaagcag   1200
ttatttttga tgttgatggc acgttagcaa aaatgaatgg tcgtggtcct tatgaccttg   1260
aaaaatgcga taccgatatt attaatccaa tggtcgttga actagctaag atgtacgata   1320
agcaaggata ttacattgta gtcgtttcag gccgtgaaag tggaactaaa gaagacccaa   1380
cgaaatatta tcgtatgacc cgtaaatggg ttgaggacat tgctggcgtt ccattagtta   1440
tgcaatgtca gcgcgaacaa ggcgatactc gtaaagacga tgtagttaaa gaagaaattt   1500
tctggaaaca catcgcaccg cattttgatg tgaaattagc tattgatgac cgaactcaag   1560
tagtagaaat gtggcggcgc atcggtgttg aatgctggca agtcgcttcg ggagattttt   1620
aatggcttgg caccatgaaa ctttgtctat tattgattgg cttgaagaaa attatgtgag   1680
gtaaatatgt ttccgactta ctctaaaatc gtagaagtag tgtttagcca aattatcgct   1740
aataatatgt ttgaaaaact tgataatgca gctgagcttc gaatccatgc tcaagtgact   1800
catgtattga atactttgct tccagaccag gtggattctg ttgccatcac gttgtatcca   1860
ggttccgcgc atatcattgt cgtatttggt cttgatgctg agctagttat tacaggcgat   1920
attcgctttg aatcacagac atcagaattc aaagcaattt aacagtttac tttacggtag   1980
agttgtgata ttatagctct accaaacaaa tgaggaaaac aaaatgctgc taagtgaaaa   2040
accaattact gttaaagaat tccaagaaaa agttaaacta tttgcacagg aattagtaaa   2100
```

-continued

```
taaggtttct gaacgatttc ctgaaacatc ggttcgtgtt attaccgaaa ctcctcgttc   2160
agtattagta attgtgaatc caggtgatgg cgatcaaata tcgcatctta aactggattt   2220
tgatggatta gttgaagcac aaagggtgta tggcgtacta tgatgaattt aactgatata   2280
attgataatt gtcttgaaaa tgatactggt gatcatagag cgcttgattc tgaaacagca   2340
aagttcatta gaataacttt aatgaatgat actctagtga atagtattca tccttctgtg   2400
tatgatgcta ttattgtgac gaagtatcca gttgagcttc acaaaaagat gactggcgca   2460
gtttttattg ataagaaaaa ccgctttaaa gatgggcaga atataattag ttctgttatt   2520
aaaagtataa ctaaacttcg tcacgaaatt tatcgtgttg aaactgctaa atctgcttat   2580
ctggtgatta tgaaatgaaa gcgagtacag tacttcaaat tgcatattta gtatcgcagg   2640
aatcaaaatg ttgctcctgg aaggtaggag cagtaattga aaagaatgga cgtattattt   2700
ctactgggta taatggttca cccgcagggg gagtgaactg ttgtgattat gctgctgagc   2760
aaggttggtt gttgaataag cctaaacata ctatcattca aggtcataag cctgaatgcg   2820
tatcatttgg ttcaactgat cgttttgtct tggcgaaaga acatcgtagt gctcactcgg   2880
aatggtcatc taaaaatgaa attcatgctg aactaaatgc aattttgttt gctgcacgaa   2940
atagttcttc aattgaaggt gctactatgt atgtaacact ttctccttgc ccagattgtg   3000
caaaagtgat agctcaatct ggaattaaaa agttggttta ttgtgaaaca tacgataaaa   3060
ataaacctgg ctgggatgat attctgcgaa atgcgggtat tgaagtgttt aatgttccta   3120
agaaaaactt gaataagtta aattgggaaa atatcaacga attctgtggt gaataatgaa   3180
atttcgtttg gtacaactca cagcaattag ttcttattct aatgagaata tttcatttgc   3240
tgtagagtat aagaaatatt ttttctctaa atggaagcag tattataagt cagaatgggt   3300
ttgtattgat agaccatata gttggaaatc tgatttagaa aaatgccaaa aattgctttc   3360
cactcttaaa gaacgtggaa caactcatat taaaactgta ataggtaaat aaatgaaact   3420
gacaactgaa cagaaagtag caattcgtga aattttgaaa actaaattgt ccatgggtat   3480
ttcaaacgta gtttttgaaa agtctgatgg tactattcgt actatgaaag gtactcgtga   3540
tgcagacttt atgccaacca tgcaaaccgg taaattgact gaatctactc ggaaagaatc   3600
tactgacatg attccagtat ttgatgttga gcttggtgca tggcgaggtt tttctattga   3660
caaattgatt tctgttaatg gtatgaaagt tgagcatttg cttcaattta ttggtaaata   3720
aatgctttaa gaattatttg ttattattaa ttcatctgtt aacaaaaagg aaaaacgatg   3780
tctgaagtac aacagctacc aattcgtgct gtcggtgaat atgttatttt agtttctgaa   3840
cctgcacaag ccggtgatga agaagttaca gaatcaggac ttattatcgg taaacgtgtt   3900
caaggtgaag ttcctgaatt gtgtgtaatt cactctgtcg gtcctgatgt tcctgaaggt   3960
ttctgcgaag ttggtgattt gacttctctc ccagttggtc aaattcgaaa tgttccgcat   4020
ccttttgtag ctctgggtct taaacagcca aaagaaatta aacaaaaatt tgttacctgt   4080
cactataaag ctattccgtg tctttataag tgatataaat aataatatga attgggtgtc   4140
ggaataataa gttaaccgaa caattctatg tggtagtcta caactgagag atctgtcgaa   4200
agaagatgaa attcagaaga acgtgactac cgagttttaa tctctaacga gaatttttaa   4260
atgattaaac aactacaaca cgctcttgaa ctgcaacgaa acgcatggaa taatggtcac   4320
gaaaactatg gcgcatctat tgatgttgaa gccgaagctc ttgaaatcct gcgttatttc   4380
aaacatctga atcctgctca aactgcatta gctgctgagc ttcaggaaaa agatgaactt   4440
```

aaatatgcta agcct 4455

<210> SEQ ID NO 23
<211> LENGTH: 14383
<212> TYPE: DNA
<213> ORGANISM: Artificial Sequence
<220> FEATURE:
<223> OTHER INFORMATION: partial sequences of Bacteriophage EK88P-1

<400> SEQUENCE: 23
tataattcat ataaattacc accgcgtggc aaaatttatt catattttgt aaaagcgggt 60
ctttctaaat taactaatag cattaatgaa ttttgaggtg aataatggct aaaaaagaaa 120
tggttgaatt tgatgaagct atccatggcg aagacttggc taaatttatt aaagaagcat 180
ctgatcataa actgaaaatt tctggttata atgaattgat taaagatatt cgaattcgtg 240
ccaaagatga acttggtgtt gatggcaaga tgtttaatcg tctgttagct ttgtatcata 300
aagataatcg tgatgtgttt gaagctgaaa ctgaagaggt agttgaactt tatgacacag 360
ttttctctaa atgatattcg tccggtcgat gagaccggtc tttcagaaaa agaactttca 420
attaagaaag aaaaggatga aattgcaaag cttcttgacc gccaagaaaa tggatttatt 480
attgaaaaaa tggtagaaga gtttggaatg agttatcttg aagctacaac agcattctta 540
gaagaaaatt ctattcctga aactcaattt gctaaattta ttccttcggg tataattgaa 600
aaaattcagt cagaagctat tgacgaaaat cttttacgcc cttctgttgt tcgttgtgaa 660
aaaactaata cattagattt tctattatga ttaaactccg catgcctgct ggtggtgaaa 720
gatatattga tggtaaatca gtttataaat tatacttaat gataaaacaa catatgaatg 780
gaaagtatga tgtaattaag tataattggt gcatgcgggt gtctgatgcc gcttatcaaa 840
agcgaaggga taagtatttt ttccagaagt tatcagaaaa atataaatta aaggaacttg 900
ctttaatctt tataagcaat cttgttgcta accaagatgc ttggattggt gacatctctg 960
acgctgatgc acttgtgttt tatcgtgaat atatcggacg cttaaagcaa attaaattta 1020
agtttgaaga agatattcgc aacatttatt attttagtaa aaaagttgaa gtttctgctt 1080
ttaaagaaat ctttgaatat aatccaaagg ttcaatcaag ttatattttt aaactgcttc 1140
agtcgaatat aatttcgttt gaaacgttta tcttgcttga ttcgttttta aatataattg 1200
ataaacatga tgaacagact gataatttag tctggaataa ttattctata aagttaaagg 1260
cttatagaaa aattttaaat attgattcac agaaagctaa aaatgttttt attgaaactg 1320
tgaaatcttg caagtattaa ttgcttatta taaatagatt ataattatct cactgaccag 1380
ctatgaggtc atacatcgtc atagcaccaa ctgttaatta aattaaaaag gaaataaaaa 1440
tgtttaaacg taaatctact gctgaactcg ctgcacaaat ggctaaactg gctggaaata 1500
aaggtggttt ttcttctgaa gataaaggcg agtggaaact gaaactcgac aatgcgggta 1560
acggtcaagc agtaattcgt tttcttccgt ctaaaaatga tgaacaagca ccattcgcaa 1620
ttcttgtaaa tcacggtttc aagaaaaatg gtaaatggta tatcgaaaac tgttcatcta 1680
cccacggtga ttacgattct tgtccagtat gtcagtacat cagtaaaaat gatttgtata 1740
acactgacaa taaagagtac ggtcttgtta aacgtaaaac ttcttactgg gctaacattc 1800
ttgtagtaaa agacccagct gctccagaaa atgaaggtaa agtatttaaa taccgtttcg 1860
gtaagaaaat ctgggataaa atcaatgcaa tgattgcagt tgatgttgaa atgggtgaaa 1920
ctccagttga tgtaacttgt ccgtgggaag gtgctaactt tgtactgaaa gttaaacaag 1980
tttctggatt tagtaactac gatgaatcta aattcctgaa tcaatctgcg attccaaaca 2040

```
ttgacgatga atctttccag aaagaactgt tcgaacaaat ggttgacctt tctgaaatga   2100
cttctaaaga taaattcaaa tcatttgaag aacttagcac taagttcagt caagttatgg   2160
gaactgctat tatgggtggt gctgcggcaa cagctgctaa gaaagccgat aaagttgctg   2220
atgatttgga tgcattcaat gttgatgact tcaaaacaaa aactgaagat gattttatga   2280
gctcaagttc tggcagttca tctagtgctg atgacacgga cctagatgat cttttgaatg   2340
acctttaata gattatatta ctaattaatc ggggacccta gaggtcccct tttttatttc   2400
aaaaaatttt ttcacaaaac ggtttacatc cttgtccttc catggtacta tacaactatc   2460
ggcaatactg ctgatgatta aagaggaaaa taatatggct aaagttgata ttgacatcgt   2520
tgattttgaa tatattgaag agattattcg taatcgttat cctgaactta gtatcacaag   2580
cgcgcaagat tctaagtttt ggagtattca aatcgttatt gaaggtcctc ttgaagacct   2640
cacccgcttt atggctaatg aatattgtga tggtatggat tctgaagacg cagaatttta   2700
catgggattg attgaacaat aattatcaag ggttatcaa gcccctatta aaatgaggaa   2760
aatcaaaaat ggaaatcggc aaaaaaatatg agttaaatcc acaccgtatt aaatctttca   2820
ttgatattag ttcatcaaat gctaatatgg tcggcatcat tcaagaaaat ggtggttggt   2880
ttgaagttaa atcaatatca agtttagatg gatttgatta tgtaaccgaa atcatttgcg   2940
ccaatggtga aatctataat gatgatggta tgggtgatga ttattttgaa cttagtgaag   3000
aagagtttta ttgttttcgt gagtataaag aaccgacttc tgaagaagat gaaatcgaag   3060
acaaggtttc tggcgtaaca aaaattcact gcattgttga cgaaaacaat gtagatgaaa   3120
tcattgaact tttgcgaaaa actttcaaaa agtagtttac agaagggtag tagtgtgata   3180
ctattaccct atcaactaag gagaataaaa tgagattaca acgtcagagc atcaaagatt   3240
cagaagttag aggtaaatgg tattttaata tcatcggtaa agattctgaa cttgttgaaa   3300
aagctgaaca tcttttacgt gatatgggat gggaagatga atgcgatgga tgtcctcttt   3360
atgaagacgg agaaagcgca ggattctgga tttatcattc tgacgttgaa cagtttaaag   3420
ctgattggaa aattgtgaaa aagtctgttt aaggaaaata atatgatttt tgtatttgaa   3480
tttatgaatg atgaattcga ttatgcaatt tttaacgcat tgcataatcc tgatttaagt   3540
gaatttaatg aaatgttttc tgacgctttg agtatgtcag aagaatactg tggagagtgt   3600
caacgtgttt gtgtgacagt ctttgaaaac aaagaaaaga catatgaaga attattcttt   3660
gatgctaata aagccactga atggtttatt gaaagggggt ttgcgtaatg attaaattgg   3720
tattcgctta ttctccaacc aaaacggtcg aaggctttaa tgaattagca ttcggtttag   3780
gtgatggttt accatgggga cgagttaaaa aggacctcca gaattttaaa gctcgtactg   3840
aaggtacaat tatgattatg ggtgctaaaa cgttccagtc attgtctaca ttacttcctg   3900
gtcgtagcca tattgtagtg tgtgaccttg cgcgtgatta tcctgtaact aaagatggcg   3960
atttagcaca tttctatatt acatgggaac agtatataac ttacatttct ggcggcgaaa   4020
ttcaagtgtc aagccctaac gcaccattcg agactatgct tgatcagaat tccaaagtaa   4080
gtgtaattgg cgggcctgct ctgttatatg ctgcgttacc ttatgcagat gaagtagttg   4140
tttctcgcat cgttaaaagg catcgtgtta attcaacggt tcaattagac gcaagttttc   4200
ttgatgatat aagcaagcgt gaaatggttg aaacgcattg gtataaaata gatgaagtaa   4260
caacccttgc ggaatcagta tataaatgaa acaataccaa gatttaatta aaaacatcct   4320
tgaaaatggt tatgaaaccg atgatcgtac aggcacagga acaattgctt tgttcggtac   4380
```

-continued

```
taaattgcgt tgggatttaa ccaaaggttt tcctgcagta acaactaaga agctcgcctg   4440
gaaagcttgc attgctgagc tactttggtt cttatcagga agtactaacg taaatgattt   4500
gcgattaatt cagcatgatt cattaattca aggcaaaaca gtctgggatg aaaattacga   4560
aaatcaagca aaagatttag gataccatag cggtgaactt ggtccaattt atggaaaaca   4620
atggcgtgat tttggtggtg tagaccaaat tgtagaagtt attgatcgta ttaaaaaact   4680
accaagtgat aggcgtcaaa ttgtgtcggc gtggaatcca gctgaactta aatatatggc   4740
attaccgcct tgtcatatgt tctatcagtt taatgtgcgt aatggctatt tggatttgca   4800
gtggtatcaa cgctcagtag atgtttttctt gggttaattg aggcctgagt ataaggtgac   4860
ttatacttgt aatctatcta aacggggaac ctctctagta gacaatcccg tgctaaattg   4920
taggactgcc ctttaataaa tacttctata ttcaaagagg tatttatgaa aagcggaatt   4980
tatcagatta aaaatacttt aaacaataaa gtatatgtag gaagtgctaa agattttgaa   5040
aagagatgga agaggcattt taaagattta gaaaaaggat gtcattcttc tataaaactt   5100
cagaggtctt ttaacaaaca tggtaatgtg tttgaatgtt ctattttgga agaaattcca   5160
tatgagaaag atttgattat tgaacgagaa aatttttgga ttaaagagct taattctaaa   5220
attaatggat acaatattgc tgatgcaacg tttggtgata catgttctac acatccatta   5280
aaagaagaaa ttattaagaa acgttctaaa actgttaaag ctaagatgct taaacttgga   5340
cctgatggtc ggaaagctct ttacagtaaa cccggaagta aaaatgggcg ttggaatcca   5400
gaaacccata agttttgtaa gtgcggtgtt cgcatacaaa cttctgctta tacttgtagt   5460
aaatgcagaa atcgttcagg tgaaaataat tcattcttta atcataagca ttcagacata   5520
actaaatcta aaatatcaga aaagatgaaa ggtaaaaagc ctagtaatat taaaaagatt   5580
tcatgtgatg ggctatttt tgaatgtgca gtagatgcag ctagacattt taaaatttcg   5640
tctggattag ttacttatcg tgtaaaatct gataaatgga attggttcta cataaatgcc   5700
taacgactat ccctttgggg agtagggtca agtgactcga aacgatagac aacttgcttt   5760
aacaagttgg agatatagtc tgctctgcat ggtgacatgc agctggatta taattccggg   5820
gtaagattaa cgaccttatc tgaacataat gctaccattt aatattgcat catatgctac   5880
gttagttcat attgtagcta agatgtgtaa tcttattcca ggagatttga tattttctgg   5940
tggtaatact catatctata tgaatcacgt agaacaatgt aaagaaattt tgaggcgtga   6000
acctaaagag ctttgtgagt tggtaataag tggtctacct tataaattcc gatatctttc   6060
tactaaagaa caattaaaat atgttcttaa acttagacct aaagatttcg ttcttaacaa   6120
ctatgtatct cacccgccaa ttaaaggaaa gatggcgata taattttaat ttaattgcga   6180
ggatatatga ttttacgatt taaagatact tctggtgtcg ttctttttac acttcctaac   6240
ccaagtgagt tagaagttcc aggaccaaat cagcctattg tcatttatgg caaaaaatat   6300
tatactcata aaatgactcg tgagtatttt gataataaaa tttctacagt taaaacttct   6360
tcagattgtt actatgatat tactgtatta acggaaaaac aatatgaaga atgtagaact   6420
ttagcagtat aaatatgatt cccaacaatc tagagcacat cttttagata taagttttct   6480
gcttattccg gtttgacgca cagcttctgc tattgttgga tattctaccc catctatact   6540
tactcttaga tggggtttct ttttacctct ttgtgagtca gaaattcgtt ttctaacttc   6600
attggtatgt gtctgtccat aatatggatt attgatgcct ttcatattaa gcgcagcgtt   6660
tctttcttgg aactttttgc ttagttctat agcacgatct aacccatagt gttcttctat   6720
agttttacct ttgatatctt taggtctacc atgtttttgc ttaagttctt ctggtgataa   6780
```

-continued

```
ttttgaatta ttatttttaa ttgcatttga aattttatta aggatttctt gctttcttgg   6840
gtgatgagat aaggtatccc caaacgatgc gtctgctata ttatacccat tttcctttga   6900
gtcatattca tgtatccaat aattttcacg ttcaataatg atagattttt cgtatggaag   6960
ttcttctatg attttacata cgaaagcatc tttcccatgc ttattataag aacgctgcag   7020
ctttattgaa tgatgatttc cattatctaa atctttaaag tgtcgtttcc atcgttcttc   7080
aaaattaatt gcacttccta tatagtgctt attggtttta gtgtttataa tagcatatat   7140
tccagatttc attatattct cctatataaa attatattta tatggggtaa cttactacag   7200
aggacttatg caattaatta atgttatcaa aagtagtggt gtttctcaga gctttgaccc   7260
acaaaaaatt attaaagttt tatcttgggc agctgaggga acatcagtag atccttatga   7320
attatatgaa aatattaaat catatctccg tgatggaatg acaactgatg atattcagac   7380
tattgtcatt aaggccgctg cgaattctat ttcggttgaa gaacctgatt atcaatatgt   7440
agctgcccgc tgtttaatgt ttgctcttcg taagcatgtt tatgggcagt atgaaccacg   7500
ttcatttatt gaccatattt cttactgtgt aaatgaaggt aaatatgacc ctgaattatt   7560
gtcaaaatat tcagcagaag aaattacatt tttagaatca aaaattaagc acgaacggga   7620
tatggaattt acttattccg ggcgatgca attaaaagaa aaatatctag ttaaagataa   7680
aaccactggt caaatttatg aaactccaca gtttgcattt atgactattg gaatggcact   7740
gcatcaagat gaacctgttg atagattaaa acatgttatt cgtttttatg aagcagtatc   7800
tactcgacag atttcattgc caactcctat tatggctggt tgtcgtactc cgactcgaca   7860
gtttagttca tgcgttgtta ttgaggcagg tgattcatta aagtctatca ataaggcttc   7920
cgcttcaatt gttgaatata tctctaaacg cgctggaatt ggtattaacg ttggtatgat   7980
tcgtgccgaa ggttctaaga ttggcatggg tgaagtacgc catactggtg ttattccttt   8040
ttggaaacat tttcagactg ctgttaaatc atgctcacag ggtggaattc gtggcggcgc   8100
tgctactgct tattatccta tttggcattt ggaagttgaa aatcttctcg ttttgaaaaa   8160
taacaaaggc gtagaagaaa accgcatccg tcatatggat tatggtgttc agctgaatga   8220
tttgatgatg gaacgattcg gaaagaacga ttacattact ttgttcagtc cgcatgaaat   8280
gggtggcgag ctttattatt cttattttaa agatcaagac cgtttccgtg aattatacga   8340
agcagcagaa aaagacccta atattcgtaa aaagcgtatt aaagcccgtg aactatttga   8400
attgctcatg actgaacgtt caggaacagc aaggatttat gtacagttca ttgataatac   8460
gaataactat actccgttta ttcgtgaaaa ggcacctatt cgtcagagta acttgtgctg   8520
tgaaattgct attccaacaa atgatgtgaa tagccaacaa acccgtttaa tcaaaattaa   8580
gaagtcggat gtagctaagt tttatgaagc taatcctggc ggtataattc aaagcaaata   8640
aagtacacag accgttaata aataatccat aacaagagga aaagttatgg attattctaa   8700
aatttacaat aaccttattt ctaaagctaa gaacagaaaa ttagattgct ataccgaatc   8760
acaccatatt atacctctgt gtattggtgg ttctgataca aaggaaaacc tggtagattt   8820
gacacccgaa gagcattaca tagctcatca attattagta aagatatatc cagataatca   8880
taaattggta tttgccgcta atatgatgtg tgtttattct gaagataata ttgaacgaaa   8940
gaacaccaat aaacgccatg ggtggcttag aagaaaattg gctatttctg tatctgaaaa   9000
taataaaggc aaaccagctt ggaacaaagg tattcctatg tctccagaag ttaaatctcg   9060
acttcaaaca tcttgggtgt ttacatttcc ggatggtcat gaggaaattc atcgaggtct   9120
```

```
taacgaattt tgtaaagagc ataatttaaa tccatctgca atgtcagccg tttgtaaagg   9180
taaacgggcg catcacaaag gatttaagtg taagaaattg gataagattt cagagcttga   9240
taatttagtt ttcgtcagta aacctcatcc aaagggatta aaaccccata acttaattgc   9300
tgtaaaaata aacggtatag aatatcaatc aatacatcga gcatctaaag ctttaggaat   9360
tactagaaaa aaggtagaag aattaaatga atattgatta tgaatttgta gatgaatttt   9420
acgaagatga tgagtatact acaataaaag ttattgaaaa cagaggagaa gtggggcttt   9480
gtactctctc tgcattcgta ctagataatt ttgactggca agaccaagat aaaattaatg   9540
aattagcaga agttcaagtt cgcgctcttg ataatctttt ggattaccaa ggatatccag   9600
ttcctgaagc agaaaaagct aaaaagcgtc gtaaccttgg tgtaggtgtt actaactatg   9660
cagcttggct ggcaagtaat tttgcttctt atgaagatgc taacgattta acacatgaac   9720
tgtttgagag attacaatat ggccttatcc gagcatcaat caagctcgcc aaagaaaaag   9780
gaccttgcga atattattca gacactcgtt gggctcgagg cgaattacct atcgactggt   9840
acaataaaaa gattgaccaa atcgcagctc cgaactacgt ttgtgactgg gcgcagttgc   9900
gggaagacct ggttgaacat ggcatccgta atagcacatt atcagcactt atgccttgtg   9960
agtcatcttc ccaagtttct aacagtacaa acggtatcga gcctccacgt ggaccagtct  10020
ctgttaaaga atcaaaagag ggctccttta atcaagtcgt gcccaatatt gagcataaca  10080
tagacctcta tgattataca tggaaattag ctaagaaagg taataaacct tatcttacgc  10140
aagtagctat tatgctgaaa tgggtatgtc aatcagcttc agcgaataca tattatgacc  10200
cgcagatttt tccaaaagga aaggttccaa tgtcaataat gattgatgac atgttatacg  10260
gatggtatta tggcattaaa aacttctatt atcataatac tcgtgatggt tctggtactg  10320
atgattacga aatagaaact ccaaaagccg atgattgcgc agcgtgtaaa ttgtaatgaa  10380
ttatcaaaaa atctataacg acctaatttc ccgagctcag gctcgggaat ctttatcaga  10440
atataaagag acacatcata taatccctag atgtatggga ggttctgatg ataaggaaaa  10500
tttagttgaa ttaacagcca gagaacattt tatagctcat ttactactat gtaagataaa  10560
tgaaggccat tttgggcttg cctctgcgtt aacgttaatg gcaacagata aagctggcaa  10620
tagaattaat aacagattgt acagcttaca cagaaaatta tttgctaaag ctaattctga  10680
gttctttaag aaatattgga aaaataatcc tcatcctaaa ggaatgttag gcaagcacca  10740
taaaaacgaa actaaacagc atgtatcaaa agtgaataga tacgcatgcc catctataga  10800
aatacataaa ttctcattag atggggattt catagaaacc tttcactcta ttgcggcagc  10860
gtcccggtca gttaatggaa acgggtcaaa tatcaaatat tgtgccgagg gtaaatttca  10920
atatgcttat ggatttagat ggtcatatca acttgatgca aagtttgaca aaataaaacc  10980
aagagattat aaaggaatcc gcggtaagaa atggattaat aatggaagtg aatgcacgct  11040
tataggtaaa gatgatatta taccgccagg ttggaaacac ggcagaattt taaagaggaa  11100
aattaatgtc tacagttttt aatacaaatc cagttgatgt tttaacagaa cctatgttct  11160
tcggttcagg tcttggaatt gcacgttatg atattcaacg acataaggta tttgaagaac  11220
ttattgaacg tcagctctcg tttttctggc ggcctgaaga agtaaactta atgatggatg  11280
ctgcacaatt taacaagctc ccagaacatc aaaaatctat atttatcaat aacttaaaat  11340
accagtcatt gttagactcc atccaggggc gtgcaccatc tgcggtactt atgccattgc  11400
tttcagatcc ttcattagat acatgggttg ctacatggac ttttagtgaa actgttcaca  11460
gtcgttcata tactcatatc atgcgtaact tgttcaatga ccctgctaag gtatttgatg  11520
```

agattgtatt agacgaagct attatgaaac gtgctgaatc tattggtcgc tattacgatg 11580
atgttcttaa gaagacccgt gaatgggaaa atgctaaaga atttgtagaa ctagctaaag 11640
aatctcctga tgctgatttt cgtttaaatc gagctattaa gcaagaagcc gaagctaaac 11700
gtgctttaat gaagtctctt tacctctgtt tacacgttat taatgcctta gaagctattc 11760
gtttttatgt atcttttgcg taaaatgcgc ctttaaacgg taacgtttat cgaaaactcc 11820
tttaattgct ggaaagtcct ttataggaaa actagcagcc aaggttttgc ttgcaccttt 11880
aattagtata atataaatat gattatactt ttaagaggat gcacaattga actatagaaa 11940
aatttggata gatgctaacg gacctatacc taaagattct gatggaagaa catacgaaat 12000
ccatcataaa gacggtaacc gtgaaaataa tgatttagat aatttgatgt gcctttctat 12060
acaggaacat tatgatatac atttagctca aaaagattac caggcttgtc atgctataaa 12120
gcttagaatg aaatattctc ctgaagaaat ttctgaatta gcttctaaag ccgcaaaatc 12180
tagagaaatc cagattttta atatccctga agtacgagct aaaaatattg cctctattaa 12240
atctaagata gaaaatggta catttcatct tttagacggt gaaatacagc gtaaatctaa 12300
tttaaataga gttgcattag gtatacataa ttttcaacaa gctgagcata ttgcaaaagt 12360
taaagaacgc aatattgcag ctataaaaga aggtactcat gtattttgcg gtggtaaaat 12420
gcagtcagaa actcaatcaa aacgggtaaa tgacggttca catcatttct tgtcagaaga 12480
ccataagaaa agaacatcag caaaaacatt agaaatggtt aagaacggga cccatcctgc 12540
acaaaaagaa atcacatgtg atttctgcgg tcacattggt aaaggtcctg gattttatct 12600
aaaacataat gacagatgta aattaaatcc aaatagaatt caattgaatt gtccatattg 12660
tgataagaaa gatttatcac catcaacata taaacgatgg cacggcgaca attgcaaagc 12720
aaggttcaac gactagtctt cggacgtagg gtcaagcgac tcgaaatggg gagaatccct 12780
ctgggattgt gatatagtct ggtctgcata gtaatatgta gcagttcata agagaacggg 12840
ttgagaatta gcgagctcaa tcgaacataa cggtaccttt aacttccata agaacatgga 12900
aatcatggaa ggtaatgcca agattatgaa gttcattgca cgcgatgaac agcttcacct 12960
taaaggcact caatatatta ttcgtcagct tcaatccggt actgatggcg atgaatgggt 13020
taaaattgct caagagtgtg aacaagaagc agttgatatt ttcatggaag ttaaccgcca 13080
agaaaaagat tgggcagttc atttatttaa agatggtgat gttcctggat taaatacaaa 13140
tagcatgtgg agctttattg attacttaac tgtatctcgt atgaaacagt gtggtcttcc 13200
atgcccaatt accgatgctc cggttaaaca tccatatcct tggattcgtg aatatcttaa 13260
ttctgataat gttcaatccg cgccacaaga agtagaactg tcatcttatc ttgttgcaca 13320
gattgataat gatgttgatg ataaagttat gatgagtttt aaaaaatact tttaaggagt 13380
gggccgcaag gcccatttta ttatgaaaga aattgcaaca gaatattcat ttattaaata 13440
tactgagtta gaattagacg acaacggaag tataaaacaa ttatctattc caaacaagta 13500
taacgtaatt tatgctattg ctataaatga tgagcttgtt tatattggaa aaactaaaaa 13560
tttacgtaaa agaataaatt attatagaac tgctattaac cgtaaagaca aaacgtctga 13620
ttctactaaa tctgcattaa ttcatgctgc gctaaaggaa ggaagcaaag ttgaatttta 13680
cgcccgccaa tgttttaatc tttctatgac aaatgagtta ggtacaatga caatcgcaac 13740
gattgatcta gaggagccac tattcattaa gctgtttaac ccgccttgga atattcaaca 13800
caagaaaaaa tgatgcttcc acatggagtg tggtactata ttcaaaacac aaaagaggat 13860

-continued

```
acacaatgca agaacttttt aacaatttaa tggaactatg taaggactca cagcgtaagt  13920

tttttactc ggatgatgta agtgcatctg gaagaactta cagaattttc tcatataatt  13980

acgcatctta ttctgattgg ttacttccag acgcattaga atgtcgtgga attatgtttg  14040

aaatggatgg agaaaaacca gtaagaattg cttctcgtcc tatggaaaag tttttaact  14100

tgaatgaaaa tccattcacg atgaatatcg atttaaatga tgttgattac attctaacaa  14160

aagaagatgg gtctttggta tcaacttatt tagatggtga tgaaattctg ttcaaatcaa  14220

agggttcaat caaatccgaa caggctttaa tggctaatgg aattttgatg aatattaatc  14280

atcaccagtt gcgcgacaga cttaaagaat tagctgaaga tggatttact gctaacttcg  14340

aattcgtcgc tccaactaat agaatcgttc ttgcttatca aga                    14383
```

<210> SEQ ID NO 24
<211> LENGTH: 28630
<212> TYPE: DNA
<213> ORGANISM: Artificial Sequence
<220> FEATURE:
<223> OTHER INFORMATION: partial sequences of Bacteriophage EK88P-1

<400> SEQUENCE: 24

```
gataataatg aaggaaatat tcattgttat aactgtaact atcatgcacc aatcggaata     60

tatttaaagg agtttgaacc tgatttatat cgtgagtata tctttgaaat aagaaaagaa    120

aaaggtaaaa gtcgtccagt agaaaaacct aaagaacttc ctaaacaacc tgagaagaaa    180

ataattaaat ctcttccgtc atgtgttaga ttagataaac tggcggaaga ccatccaatt    240

ataaaatatg taaaagctcg ttgtattcca aaggataaat ggaaatatct ttggtttaca    300

accgaatggc ctaaattggt taatagcata gcaccgggaa catataaaaa ggaaatttct    360

gagcctcgtc ttgttattcc aatttataat gctaatggaa aagctgagtc gtttcaagga    420

cgtgcattaa agaaagatgc tcctcaaaaa tatatcacca tcaaagctta tcctgaagca    480

acaaaaatct atggagtcga acgagttaaa gatggtgatg tatatgttct agaaggacct    540

atagattcac tttttattga aaatggtata gctattacgg gtggtcaatt agacctagaa    600

gttgttccat ttaaagatag acgagtgtgg gttttagata atgaacctcg tcaccctgac    660

actattaaac gaatgactaa attagttgat gcaggagaaa gggttatgtt ttgggataaa    720

tctccctgga aatcaaaaga tgttaatgat atgattagaa aggaaggtgc aacccctgaa    780

caaattatgg aatatatgaa aaataatatt gcccaggggt taatggctaa aatgcggcta    840

tctaaatatg ctaagattta aattaaccca actaaagcaa atgctaaatc tacgaatgta    900

tcaagagtaa ttactggaat attaacacca tgagcaatag caactggcga taaaacaaaa    960

ttccaaagta aaattcctat catagcagaa atagtaaaag ctatacgttt cttattacct   1020

tttatggcat taacaagtgc cattaatttt tgtaccatat gtcctccttt aaattaatat   1080

ttatcataaa tttgtttact ttctcagctt gttatggtat tataaaataa attgttgagg   1140

atgatataat gattaataaa attgtgcatg aaatggcttt aaacggagat tcatataaaa   1200

tatctgccgt agttgaaaat ttcatactta ataaagtaaa agaatatttc actgattgtt   1260

cagttagtta tcaagaaaaa atggttttaa ccgatgatac tgaaaaatca aataatttgt   1320

tttgctctaa ttttataact aagaagcgta ctagaagatt tgatattgtt atttctcgca   1380

acggtaaaaa gcatataatt gaaattaaac atcaagttgg tggaggtaca gctattgatt   1440

cggttggaat atatttagaa gataaagaga aattaaaaga atacacaaaa actgaaaacc   1500

ccgtgtcatt gatgatatta gattttttgc catgcggata ttatccacgt aataaatgga   1560
```

caaaaagaga atcatttact gataatccaa ctatccaagc aaggtttaat gaatatgcta 1620
aatcacaaaa cgtgttagta ttactatcaa atacatatga tgaagaatta tataattcgt 1680
tttttgctgc aataaatgag agaatataat gctaggagct atcgcgtata caggtaataa 1740
acaatcatta ttacctgaac ttaagcctca ctttccaaaa tatgacagat tcgtggattt 1800
attttgtgga ggtttatcag tgtctttgaa cgtcaatggt cctgtattgg ctaatgatat 1860
tcaagaacca attattgaaa tgtataagcg tcttattaat gtatcatggg atgacgtttt 1920
aaaagtaata aagcaataca aattatcaaa aacatcaaaa gaagagtttt tgaaattacg 1980
tgaagattat aataaaacta gagatcctct tttactttat gttcttcatt ttcatggatt 2040
tagtaatatg attcgtataa acgataaagg aaattttact actccgtttg gaaaaagaac 2100
tataaacaaa aatagtgaaa aacgctttaa tcactttaag caaaattgtg ataaaataat 2160
ctttagttca ttgcatttta aagatgtcaa aattctagac ggcgattttg tatatgtaga 2220
tcctccgtat ctcataacag ttgctgatta taataaattt tggtcagaag aagaagaaaa 2280
agacctttta aatcttttag attctttaaa tgacagagga ataaaatttg ggctgtcgaa 2340
tgttttagag catcacggaa aggaaaacac tcttcttaaa gaatggtcta aaaaatataa 2400
tgttaagcat cttaataaaa aatacgtctt taacatatat cattccaaag aaaagaatgg 2460
aactgatgaa gtatatattt ttaattaatt gcttacacac tcaaatgata taattattta 2520
acttattaat gaattgaaag gatatatgtg aattaccaaa aaatttactc ggctttaatt 2580
acaaaagcta aatgccggca tcttgatgga tataaagaac gccatcatat aattcctaga 2640
tgtatgggag gagcagatga caaaaacaat cttgttgagt taactgcgcg tgagcatttt 2700
atagctcata gattattaac taaaatatat ccagatgtga gaggattgca ttatgctgta 2760
aatttaatgc gatataataa aggtgttaaa ttaacaagta gattaataga aacccttaaa 2820
atccaaaact ctgttctttt ctcgggtgaa aataatccta gatatggcaa gccgtcatgg 2880
attaaaggca aaaagactcc agaagaaact aaagccaaaa tgcgtctagc tcataaaggt 2940
aaaattatat ccgatgaagc caaggctaat atgagtaaag cccgaaaagg aagatttagc 3000
ggtaaaaatt cgcctcgata tggtttacca aatcctaggc gaggggaaat atggaatagt 3060
tatgatgcgc tttatgaatt atgggtttat aataatagac ctaagcgcac aaaatttaat 3120
aaaatagctg tcaaggcagg ttatcctaat atctgctata gacatatgat agaaaacttc 3180
ataagaaagg aaaaataaca tgccacattt caacgaatgt agtcaactga ttgaaggcgc 3240
ggataaagct caaaatgaat actgggatat tcttggtgat gaaaaagacc cgctgcaggt 3300
aatgcttgac atgcagaaat ctctgcagat tcgtttagca aatgaccgcg aatactgcta 3360
tcatccagat aaattagaaa ctgccggtga tgttgtttct tggatgcgtg aacaaaaaga 3420
ctgtattgat gatgaattcc gtgaacttct gacttctctt ggtgaaatgt cacgtggtga 3480
aaaagatgca tcggcagttt ggaaaaaatg gaaagcacgt tatattgaag cgcaagaaaa 3540
acgcattgat gaaatgtcac cagaagatca gctcgaaatt aaatttgagc ttgtggatat 3600
atttcatttc gtattaaata tgtttgctgg ccttggaatg tcagctgaag aaatctttaa 3660
actttattat ctgaaaaatg ctgaaaattt cgctcgtcaa gaccgaggtt attgatggct 3720
cgtttaaaat aaacgccaac tcaagaaagc ccgcaagaaa cgtattgacc agctatttaa 3780
agattatgac aaggagctca catatgagct cttatctaat cagcttcgta tggttgattg 3840
ggttgcagaa gaaggccctg acgaaatttt tgtaagtgaa gaagccttaa aattaattat 3900

-continued agagcattca aaatgaaaat atccaaagaa gaatttatta gacgtcaaaa agctttaatt 3960
aatttacatg agtggtatgc ttatcaactt aaagtagata gctctaacat aaatgctgta 4020
atggctttat ataaacaaat tcaagatgag catgaattcc tggcacaagt tttcattgaa 4080
gattgatata aatacatctg taattaaaca ataaaggagt ttattatggg tggtttcgtt 4140
aacatcaaga cctttactca tccagcgggt gaaggcaaag aagttaaagg tatggaagtt 4200
tctgtagcat ttgatgtata ttcaaatgaa caccgtattg cagattctca ttatcaaatc 4260
tttccgtcag aaaaagcagc ttattctgat gtagtttccg atgcagcaac ttggaaaact 4320
aagaatgctg caatgtttac gcctacaaca ataggcggtt aataattcaa ggactccttc 4380
gggagtcctt tttttcattt tatggtttac tttccaaaat gagtgtggta taatagaatt 4440
atcttataga ggagagcact atgttaaatc gttggattaa accaaatgaa gaccttcaga 4500
aggttcttga taaagctatc tctgataaat ggggtatgaa aagctgggat tgtgatgtcg 4560
tcacgcattc attcatgatg catgcagatg gttcagtcga gttcaatgct gaaatgcgat 4620
atactgactg ggtggatttt caaagagtcg aatttcaaag aggctttttg taatgtttat 4680
ctttaattgg tttaaaagtt tctttacgga ttttttctct acaactcccg gagaaggtgt 4740
agttcctatt tcaaatgact accttccttt aactgtagtt gagtatgttt atatgggaga 4800
tggaacagta gaagcagtta ctatgactta tgaagaagcc caagaatatt ataaaaatcc 4860
ttggcgctgg tcaacaccta ctacatcatc taatacgcag aatacacagt ctagttctga 4920
ttcatatgat actaatgttc ctgttcatgt atggacgggc gattcatgcg gaagttcttg 4980
tgattctggt tgttcatcta catcttgtga ttgaggaaaa ttatggaagc gattttattt 5040
gaaatgtata ttagcagtaa tagcatgtcg tttgctaaag atgttccaat tactgtagcc 5100
gtagtgattg ataagggtta ttgcaaccct atgtatctcg tagaaaattt cgtttcaatg 5160
ccagttccag aagatgttga aataaaactt aaaaagatcg gaattattga aactgtgcca 5220
aatagtccgt ttagagcaat tgaagcattt actaaatccg aatacattaa tgttagcgca 5280
gaacaatata atggtaatcc tttatctttt tattcgtacg attcagtata tgactggaaa 5340
ataaatgaag gaaataaatt tataattgcg agtgaagatg ctttatcata ctttatttat 5400
tatgtatgga ataatttaaa tccaaaattg ctaaaaattc atgaatttga cgatgctcct 5460
actattgttt taggtaaaac aaatgaaagt tctgaagaaa atgcttgaat ggttcaatag 5520
accaaactca atgtatattg atgatggctg ggttgaacaa gcaaataaag aaatgcagaa 5580
cgaatcagaa gaatggatga aatcaatgat tagtgctgag aaagaaaaga aattagaacg 5640
ctcagcgctt aaattgatga gagatatcta tggggataaa tcatgaacag agatatgacg 5700
ctagaagagg ccaaggctaa agcaaatgaa gcactggatt tgcttcttaa aattggtagt 5760
aaaatgatgg aagaaaatga gaaatacatt caggaaaaca aaattcctga cggcccatta 5820
gtaggcaaga ggaaatcaca tgattgaagt agcaaaacat tattcaatag aatttatgtc 5880
taaagaaggt aaatcagtaa atacacttga taaaaagtgc tcattaatta ttcctttagc 5940
agaaaatccg gatattttaa ttaaagatat aaaagaaaga aaatatccag aaaatgttat 6000
tctaattata aagcatactg aagatatttt gcagaataca gattcaccat tttcttcttc 6060
tgaagcttta actattaaag gctataaaag agctcatgaa tatggtcttt ttgacatgtt 6120
tgaagatgat aaggttaaat tagcgagtca accttctaaa agtaaaacat tcattattga 6180
agatattaaa gatataaatg catttgttaa gatggtctgg gctcattttg atgttggact 6240
acgttggaga atgtccgaag aagaaagaaa gattattgaa gctaatcgtc aatttggttt 6300

-continued

```
ttatcgctag gaattagtat ggatttattt gagatgttag aagataatca ttctacgaat   6360
atccagaatg attccagtga ttataagaaa gaataccgta tagtattaca gaattatgga   6420
attgaagccc cagatgctct tctagaagaa ctagcttcat accatcttga ccctccgcct   6480
tgggctccct gggcaaaata attcaaaaag ttgtttactt tcctttctaa cgatgatatg   6540
atagcttctg aagtatatgg aggctatcat gattattaat cttgcagatg ttgaacagtt   6600
atctataaaa gctgaaagcg ttgattttca atatgatatg tataaaaaaa gtctgtgaaa   6660
aatttactga ctttgagcag tctgttcttt ggcaatgtat ggaagccaaa aagaatgaag   6720
ctcttcatcg gcagttgaat aaaatcatta aaaagcattt aactaaatca ccttatcagt   6780
tatatcgtgg tatatcaaaa tcaacagaag aacttattaa agatttacaa gttggagaag   6840
tgttttcaac gaacagggta gattcattta ctactagttt actcatagca tgttcttttt   6900
cttatgctga atattttact aaaataatat tccgcttaaa aactgataaa gcttttaatt   6960
attctgacca tatcagcgat attatacttt cttctcctaa tactgagttt aagtatacat   7020
atgaagatac tgatgggcta gattcagagc gtactgataa cttaatgatg attgtgcgtg   7080
aacaagaatg gatgattcca attggaaagt atagaataac ttctatttca aaagaaaaat   7140
tacacgattc atttggaaca tttaaagttt atgatattga ggtagttgaa tgaaataccc   7200
agtaatgcaa ctaaaagatt ttaaaataaa atcaatggat gcatcggtgc gtgcttctat   7260
tcgtgaagaa ttactttctg aagggtttaa tttatctgaa attgaacttt taattcattg   7320
tattactaat aagccagatg accatacttg gttaaatgaa ataatcaaat ctcgtttggt   7380
tccaaacgat aaacctcttt ggagaggtgt tccagctgag actaagcaag tattaaatca   7440
aggaattgat attattacat ttgataaagt cgtatcagct tcatatgata aaaatatagc   7500
tctacatttt gcttccggtt tagagtataa cacacaagtt atttttgaat tcaaagctcc   7560
tatggtattc aatttccagg agtatgctat aaaagctcta cgctgtaaag aatacaatca   7620
aaactttaag tttccggata gccatcgtta tcgtaatatg gaattagttt cagatgaaca   7680
agaagtaatg ataccagctg gaagtgtatt tagaattgca gatagatatg agtacaaaaa   7740
gtattcaaca tacactatct atactcttga ttttgaagga tttaatctat aatggaagga   7800
cttagattca ttataccatg aaagttttaa agcatttttc ataaagttgt ttacaagtta   7860
aagtaaaaat gttatagtat aagtaattaa ccgtccgtaa gatgtgagaa aaatatgaag   7920
ctgtctaata atcaaattcg taaaattaaa cgtcgtctag agcatactca ggcatctgca   7980
aaaagacgtt ctaaagattt taacttagac ttcaattaca ttaagaacat tttagaccaa   8040
aaagtttgcg cttactcggg agaacctttt gataatcgta ttgaaggaga gaaattatca   8100
ttagaacgtt ttgataataa cgttggatac attaaaggga atgttattgc agtaaagaaa   8160
aagtataata catttcgttc tgattatact ttagaagagt tgattgaaaa gcgtgattta   8220
tttgctttgc gaattggtcg ttcatctgcg aaaaaagttc ataaactaaa tttagatgaa   8280
aagaaatggg ctaaaatcaa aaagacttat aatcaaatta aagctataca gaaaaaacgt   8340
gaaaaccgaa ttgaacacat ttctcagctt tctaaatcaa aacaaacttc tgacgttaag   8400
ctaacgatta tagcactcaa agctcgtatt gatggttctc gtatagcaga aggcgctgaa   8460
gttgttaaat tgaacgttct tcttaaaggc tcggattgga aaactgtgaa aaagttgtca   8520
gaagcagaaa tgcaatatga tatgtgtgat aaaattattc aaggtgtaga gcggtatcaa   8580
aacttgtctt ttattgataa acttaaactg aaaagaggat acccgctaaa ttgttcaatt   8640
```

```
tttaaactta tccgaggata atatgtttta tgtatatgcg atagtttacc gagacaaaga   8700
cggatttacg gcgccagttc ctcttgatga acatcgtcct gctgtatttt ttgaaaggga   8760
gattgctgat aaagtattta ctactcttaa agagcagtat cgactagctt taggtatggg   8820
aattccgaga ttagttgaga ctccacgcaa gttttggttt aataaaatag aagttaaaca   8880
tgttaagcct gacgtagaca cacaaagatt atatcagcga attttagata ctgggcgtat   8940
tgttagtatt ccaattgcag ggactttccg atgacatttg atgatttgac cgaaggccag   9000
aaaaatgcct ttaacatcgt tatgagggct atcaaagaaa agaaacatca tgtaactatt   9060
aatggacctg ctggtaccgg taagactact cttactaagt tcatcattga agctttaata   9120
tctacgggtg aaactggtat tattttagca gctcctacac atgcagctaa aaagattctt   9180
tcaaaactat cagggaaaga agcgagtact attcatagta ttcttaaaat taacccagta   9240
acatatgaag aaaatgtcct ctttgagcag aaggaagtac cagatttagc taaatgcagg   9300
gtattaatct gcgatgaagt gtcaatgtat gatagaaagc tatttaaaat tctgctttca   9360
actatcccgc catggtgtac tataattgga ataggcgata ataagcaaat tagacctgtt   9420
gacccaggag aaaatactgc ttatatcagt ccattcttta cacacaaaga tttttatcag   9480
tgtgaactta ctgaagttaa acgcagtaat gctcctatta ttgatgtagc tactgatgtt   9540
cgtaacggta agtggattta tgataaaatt gttgacggtc atggagtacg tggatttact   9600
ggtgataccg ctttacgcga ttttatggta aattattttt caatcgtcaa atctttagat   9660
gatttgtttg aaaatcgtgt aatggcattt acgaataaat ctgttgataa gttaaatagc   9720
attattcgta aaaagatttt tgaaactgat aaagatttta ttgtcggtga aattattgta   9780
atgcaggaac cattaattaa aacatataaa attgatggaa agcctgtgtc agaaattatt   9840
tttaataacg gacaattagt tcgtattata gaagcagagt atacatcaac atttgttaaa   9900
gctcgtggtg tttctggaga atatctaatt cgtcattggg atttaacagt agaaacttac   9960
ggcgatgatg aatattatcg tgaaaagatt aaaataattt catctgatga agagctgtat  10020
aagtttaact tatttttagg taaaactgca gaaacttaca aaaattggaa taaaggtgga  10080
aaagctccgt ggagtgattt ttgggatgct aaatcacagt ttagtaaagt gaaagcactt  10140
cctgcatcaa cattccataa agctcagggt atgtctgtag accgtgcttt catctatacg  10200
ccttgcattc attatgcaga cgctgaattg gcccaacaac ttctttatgt tggtgtcacc  10260
cgtggtcgct atgatgtatt ttatgtatga ttaaatttga ggaagctatt cgtggaaata  10320
actaaagaac agttttatct tcttcaggat aaagttagcg aaatttatga aattgcttat  10380
ggtaaaaatc gtaaaactgt aaaaattgaa tctagtaagt tgatgcttca attagaagaa  10440
attgaacgag atttaattgc gttagaattc ttttgcggtg aagtgaaaac tgttacaatt  10500
aatgattatg ttttaggcga aattagctat ctttatgagg cgattattaa tgattgagtt  10560
gagttggtac cagtttaaat ctcttatggc aaatgttaaa gctgtcattg aggaaaatcc  10620
aggacctgat aatgttacta ttcgcgaaaa agcttcaaag atagtataca gtcttgaaga  10680
gatacaaaaa gatattgaat ctatagcaaa atttattgat gagcccatta ataaagttta  10740
tatccaagat tatactgtag gtcaaattcg cgatttagcg aggaaaattt aatgtttgat  10800
tttattatag attttgaaac aatgggaagc ggtgaaaagg cagctgttat tgatttggct  10860
gttattgcct ttgaccctaa tccagaagta gttgaaacat ttgatgaatt agtttcgcgc  10920
ggcattaaaa tcaagtttga tttaaaaagc caaaaaggac atcgtctttt tactaaaagc  10980
actatcgaat ggtggaaaaa tcaatctcct gaagctcgaa aaaatattgc accatcagat  11040
```

```
gaagatgtaa gcactatcga cggtattgcg aaatttaacg attacatcaa tgcacataat  11100
atcgatcctt ggaaatctca aggctggtgc cgtggaatgt cgtttgattt tccaatttta  11160
gtcgatctca ttcgcgatat tcaacgtctt aacggcgttt ccgagaatga gcttgataca  11220
tttaagttag aaccgtgtaa attttggaat cagcgtgata ttcgtaccag aattgaagca  11280
cttctgcttg ttcgtgatat gaccacatgt cctcttccaa agggaacttt agatggattc  11340
gttgcgcata attctattca tgactgtgcg aaagacatcc tgatgatgaa gtatgctttg  11400
cgatacgcta tgggtcttga agatgctcca tcagaggaag agtgcgatcc tctgtctctt  11460
ccaacaaaac gataaaaaat tgtttacttc ctcggttagt tgtggtatta taacatcata  11520
gctactgagg ataataaaat gaaaatttat cgtgttgaat catcgtttag tattcttaat  11580
tatgaagatg ctataacaat acgtcgaaat ctttgtgttc aaataacgcc atacaggagt  11640
ataatagatt catggagcga agagtggcta ttacacgtag gttatgacag acctaatttt  11700
atgcatcata gcgataataa taaaagaatt cctttaccac acgaagataa actattagtt  11760
aaaaacgcta atatagtaat taatactaag ttcaagaaag attatgttgg agtagaatat  11820
catattccag ggtggtttat aggtctttat cattttgctt tcgctagtga atatgatatg  11880
atgagatggt tcacacgaga agagcgggaa gaattatctt ctaaaggatt ttatctcgct  11940
gtatacgaag ttcctgaaga tgaagttatc attggtgggc accaagtaat gttccgcaaa  12000
tcgcatgctg aactcgtaga ttttattgaa atgagataat tatgaaattt aattataatc  12060
ctgaatacac accgaatccg gtagctaaac tgattgattt tgatgttgta agcacttatg  12120
tatgccctgt taaaccactg gaaattaagg aacctactat gactaccgct attgaaatcg  12180
gcaaaaccta caaactggtt gaacctaaaa ttaaaactaa tgccttgatt tctggtcata  12240
aaactctgac tgatgttttt ggcgaaggcg aatttattgt tgaagaattt gccaaaagtg  12300
agtggtttga caaatcttac gtcatccacg gtcgccggtt agataataac aaaataaaga  12360
aaaacctggt ttatgaagat gagttcatcc tgttccaaga agttgaagaa caagacccta  12420
cagacctgtt gtgtgctgct gtgtctatcc gtcgtccttt tgataatcct atctgtggtt  12480
gggtaacaga ccagtgggta gaagatggtg ttgaacttct gaacgttgtt catgcaggtg  12540
attttagcgt agtacctcgt agtgcggtgg tagctatttt gaattaatag tttacaaact  12600
cttgggacca gagtataatg gtcctgtgga gtataaaatc tttttaacaa gtgagagata  12660
actatgatta ttaatattgg tgaaattgct cgtgtatctg ataaatcccg ctctaaagca  12720
gcaggaaaat tggtcgaaat tgtaagcatt cagcttaaac acggcgttaa agatgaagat  12780
tctgaagtaa aagtgcgtat cattcctaaa gatggaaagt ctaaacctca gtttggttat  12840
gttcgcgcga aatttcttga atctgcgttt ttgaaagctg ttcccgctaa aggaattgaa  12900
acgattgata cttcgcatgt aggtgtagac tttaagtgga aactcggtca agctattaag  12960
ttcattgctc cttatgaatt cgaatttact gaagatgagg aaggggttgt tcaaaaacgc  13020
cgtactcgtg ctatgtgcgc atacattact gatcaatggg tagaagatgg tgttaagtta  13080
tacaacgcgg tatttttagg aacatacaaa gtcattcctg aaagttggat taaacactac  13140
agcaaagctc gctatgcata aagtttaaaa ttttttcata aaactatata catcagtagt  13200
tgattatggt actatatcaa tatcaactac tgatacagaa aacaacttgg agaataaaat  13260
ggaaattcgc taaaggtgct gatactcttc tgaaacgcat cgctccaatg tttaattaat  13320
gaggaaattg taatgaaacg taaaattgtt cagaattgca ctaatgatga atttgaagat  13380
```

```
gtattatttg atccaaattt ggtagtagtt caaaaggaac atactagcaa gtttattcac  13440
ttgacttctg tttatgtgta tgagaaagtc ggtgataaac aaccaattta tggtgtattt  13500
cgtgaaatta ctgaaaatgg cacaacttat tggaaggaaa tttattaatg gctattaaat  13560
ttgaagttaa taaatggtat caattcaaaa ataaacaagc tcaagaaaaa tttattaaat  13620
atcatactga aaacggaatt tatgcacgac gtttaggtat ggaacctttt aaagttatag  13680
atattgacta tcttggtcgt cctactaaaa ttgtgacatc tactggaaga ttggcattat  13740
cctccggtaa agatattttg gatgaagatt ttatttggct ttctactagc gaagctgaat  13800
tctttgatga agttgaaaat ccataccagg cagctgaaga gcaagagcag gaagagaaag  13860
agcaagaaca aatagaagat ttcacagaat ttcctgtcat gaaagttact attgaaaata  13920
atgaacaggc atggtccttg tatcaaatgc tgaaagcaca ctttaaggaa taattatgcc  13980
aatgtatgat tataaatgcc aatccgaaga ctgtgcaaaa gaatacgaaa aaatcaagaa  14040
aatttctgaa agggatactg atgtatgtcc tgattgtcat cggattgcta ttcggttagt  14100
ttccgctcct aagcatgtga acggtggatt ttacgactta cttaaagggt aattatgaaa  14160
tatgttaatc gttctatcgc agcattagta ttagcagtgt ctttagtagg atgtactgat  14220
gctgataatg caaccaaagt tttgtcttca agtggtttta ctaatattga aatcactgga  14280
tataactggt tcggttgctc tgaaaatgat ttccaacaca ctggatttcg tgctgttgga  14340
cctactgggc agaaagtaga aggaacagta tgttctggtc tattcttcaa ggattcgact  14400
atccgtttta aataaaaggc cttcgggcct ttagctttat gattaccgga gtataatatt  14460
cccgaaacca aacgaggata agtgatgatt aagaatgaaa ttaaaattct gagcgatatt  14520
gaacatatca aaaagcgtag cggcatgtac attggctctt ctgctaatga aatgcatgag  14580
cgctttctgt ttggtaaatg ggaaagtgtt cagtatgtac ctggtcttgt taagcttatt  14640
gatgaaatta tcgataactc agtagatgaa ggtattcgta ctaagtttaa attcgcaaat  14700
aaaattaatg ttactattaa aaacaatcaa gtaacagttg aagataacgg tcgtggtatt  14760
ccacaagcga tggttaaaac acctactggt gaagaaattc ctggtccagt tgctgcatgg  14820
actattccaa aagcaggtgg taactttggt gatgataaag aacgcgtcac cggtggtatg  14880
aacggtgttg gttctagttt gacaaacatt ttttctgtga tgtttgttgg tgaaactggc  14940
gatggtcaaa ataatattgt agttcgttgt tcaaatggca tggaaaataa atcatgggaa  15000
gatattcctg gaaaatggaa aggaacccgt gttactttca ttcctgattt tatgtcattt  15060
gaaactaatg agctgtccca agtttatctt gacattacac tagatcgtct ccagacactt  15120
gctgttgttt atcctgatat tcaatttacc tttaatggta aaaaggttca gggcaatttt  15180
aagaaatatg cacgacagta tgatgaacat gctattgttc aagaacaaga aaattgttct  15240
attgcggttg gtcgttcacc tgatggtttt cgtcagttga cgtacgtcaa taacattcat  15300
actaagaatg gtggccatca cattgactgt gttatggatg atatttgtga agaccttatt  15360
ccacaaatca aacgtaagtt caaaattgat gtaactaaag cgcgtgttaa agaatgtttg  15420
actatcgtta tgtttgttcg tgatatgaaa aacatgcgat ttgattctca aactaaagaa  15480
cgacttactt ctccttttgg tgaaatccgt agtcatattc agcttgatgc taaaaagatt  15540
tcacgcgcta ttctaaataa tgaagcaatt ctgatgccga ttattgaagc tgctttggct  15600
cgtaaattgg cggcagaaaa agcagcagaa acaaaggcag ctaaaaaggc ttctaaagct  15660
aaggttcata aacatattaa agcgaacctt tgcggtaaag atgctgacac tacattattc  15720
ttaactgagg gtgattcggc tatcggatat cttattgatg ttcgtgataa agaacttcac  15780
```

ggcggttatc cattgcgtgg taaagttctt aatagctggg gtatgtcata tgctgatatg 15840
cttaaaaaca aagaactatt tgatatttgc gcaatcactg gattagttct tggtgaaaag 15900
gcgtttgaag aaaaagaaga tggcgagtgg tttactttcg aactaaatgg cgatacaatt 15960
atcgtaaatg aaaatgatga agtacagatt aatggtaaat ggataacagt aggtgaatta 16020
cgaaaaaatc tataatgact taataatgcg gggtaaaacc cgcgtttcta aatttaaggg 16080
tgaaattcat catatccttc caagatcaat gggaggttct gatgataaag aaaatttggt 16140
gaaactgact tttcgtgaac actttttagc acattttcta ctatataaaa ttcatcgtaa 16200
tcgtgaaatg gcatatgcga tgaatagaat gttaaacact gaaaaatatt tacgttctag 16260
taaattatat gaaattgcta gaatttacca tcaaagagca gtatctgaat ggtcaaaaaa 16320
ctttatgaaa gataaagttt taatgagaag tattaaatcg ggtaaatgcg ccttattaat 16380
taaaggatca tttaacccaa aggaatggtg cggtgttaat aaaggtgtta agcttcctgg 16440
aattaaaggc atgacatgct ttaaaaatga aaaaggcgaa gtttttcgtc ttcatgttaa 16500
tgatccacgc attaaagctg aaaaattagt tggtattgga aatactgttg ctgctactgc 16560
aaaagcagct gaacttgaaa aagcgaaacc atggtataat aaatcagcga caaatccaga 16620
ggctgtaaaa ttaataccaa atttatatga atggtacgtc acgaaatatg accccgatca 16680
ttataaacga acgggagttg ctaaatggaa atcagttaat aatataactg tgaattcaaa 16740
attattcggc cgagcattta atgaatttaa acgcggctgg attcctgatg aaaagttcta 16800
cgaggtgtat aatgaaattt gtaaaaattg attcttctag cattgatatg aaaaaatata 16860
aatcgcagaa caatgtccgt cgttctatta aatcctcttc aatgaactat gcgaatgtcg 16920
ctattatgac agacgcagat cacgatggat agccttcggg ctatccattg aaatacctca 16980
taattaagag attattggat taggttctat ttatccttct ctgctcggat tttttagtaa 17040
ttggccagaa ctgtttgaac aaggaagaat tcgctttgtc aaaactcctg taatcatcgc 17100
tcaggtcggt aaaaaacaag aatggtttta tacagtcgct gaatatgaga gtgccaaaga 17160
tgctctacct aaacatagca tccgttatat taagggactt ggctctttgg aaaaatctga 17220
atatcgtgag atgattcaaa atccggtata tgatgttgtt aaacttcctg agaactggaa 17280
agagcttttt gaaatgctca tgggagataa tgctgacctt cgtaaagaat ggatgagcca 17340
atagtttact ttaccacaag gatgtggtat aattaattgg gcaaatgagg atattgaaat 17400
gaaatcatat aaagtaaatt tagaactttt tgataaagca gttcatcgag aatatagaat 17460
cattcaacgc tttttcgata tgggagaagc agaagaattt aaaaaccgct ttaaagatat 17520
tagagataaa attcaatccg acactgcaac taaagatgaa ctactagaag ttgctgaagt 17580
tattaagcgt aatatgaatt aatgaggaaa ttatgattat caccactgaa aaagaaacaa 17640
ttcttggtaa tggttctaaa tcaaaagcat ttagcatcac agcatctcct aaagtattta 17700
aaattctgtc atctgatttg tatacaaaca agattcgcgc agtagtccgt gaattgatta 17760
ctaacatgat tgatgcccat gctctcaatg gaaatcctga aaaatttatc attcaagttc 17820
ctggacgttt agatccacga tttgtttgtc gagattttgg tccaggtatg agcgattttg 17880
atattcaagg tgatgataat tctcctggtc tgtataattc atacttcagt tcatctaagg 17940
ctgaatctaa cgatttcatt ggcggatttg gtttaggttc taaatctcca tttagttata 18000
ctgatacatt tagtattact tcgtatcata aaggtgaaat tcgtggttat gtagcttaca 18060
tggatggtga cggtccgcag attaaaccta cattcgtaaa agaaatgggt ccaaacgata 18120

-continued

```
aaactggtat tgaaatcgta gttccagttg aagaaaaaga ctttagaaac tttgcttatg  18180
aagtttctta tatcatgcga ccattcaaag atttggctat cattaatggt cttgaccgcg  18240
aaattgatta ttttccggat ttcgatgact attacggcgt aaatccagaa agatattggc  18300
cagatcgtgg tggattatat gctatctatg gcggtattgt ttatcctatt gatggtgtta  18360
ttagagaccg caactggtta agcattcgca atgaagtgaa ttacattaag tttccaatgg  18420
gttcacttga tattgctcca tctcgcgaag ctctttcatt agatgatcgt actcgtaaaa  18480
atattattga gcgcgtcaaa gagcttagtg agaaggcatt taatgaagat gtaaaacgat  18540
ttaaagaatc tacatctcct cgtcatacat atcgcgaatt aatgaagatg ggatattctg  18600
ctcgagatta tatgattagt aattcagtca aattcacgac taaaaatctg tcatataaaa  18660
agatgcagag tatgtttgaa cctgacagta agttatgcaa tgcaggagtt gtgtatgaag  18720
taaatcttga ccctcgactg aaacgcatta agcaaagtca tgaaacttca gccgttgcat  18780
caagttatcg tctgttcggt attaatacaa caaaaattaa tatcgttatt gataatatta  18840
aaaatcgtgt taatattgtc cgtggattag cgcatgcgtt agatgataaa gaatttaata  18900
acactttgaa tattcatcat aatgagcgtc ttctgtttat taatccggaa gtagaatcgc  18960
agattgattt actccctgat attattgcaa tgtttgaaag tgatgaagtt aacattcatt  19020
atttgtcaga aattgaagct ttagttaaaa gttatattcc aaaggcagtt aaaagtaaag  19080
ctcctcgtcc taaagctgct actgcattta agtttgaaat taaagacggg cgctgggaaa  19140
aagaggaact gtttacactt acgtcagaag cagatgaaat tactggttat gtagcataca  19200
tgcatcgttc tgatattttc tctatggatg gtactacatc gctctgtaat ccgtctacga  19260
gtattttgac tcgtatggct aatcttattg gcattaatga attttatgtt attcgtccac  19320
ttttgcagaa aaaggtaaaa gaacttggtc agtgccaatg tatttttgaa actctacgtg  19380
atttatatgt agatgctttt gatgatgtag attatgataa gtatgtaggt tattcaagtt  19440
cagctaaacg atatattgat aaaattatca agtatcctga gttagatttt atgatgaagt  19500
acttcagtgt agatgaagtt tccgaagaat atacacgact cgctaatatg gttagttcat  19560
tacagggtgt atatttcaac ggtggaaaag ataccatcgg tcatgacatc tggacagtaa  19620
ctaatctttt tgatgtatta tcaaacaatg cttcaaaaaa cagtgataaa atggttgctg  19680
agtttactaa gaaattccgt attgtttccg acttcatcgg ttatcgcaac tctttgagtg  19740
atgatgaagt ttcccaaatc gctaaaacta tgaaggccct tgcggcctaa taaggaaaat  19800
tatgtacaat attaaatgcc tgaccaaaaa cgaacaagct gaaattgtca aactgtattc  19860
aagtggtaat tacacccaac aggaattggc tgattggcaa ggtgtatcgg ttgacacaat  19920
ccgtcgtgtt ttgaaaaatg ctgaagaagc taaacgccct aaagttacta ttagtggtga  19980
tattacagtt aaagttaata gcgatgcagt tattgctcca gttgctaaat ctgacattat  20040
ttggaatgca tctaaaaaat tcatttcaat tactgttgac ggtgtaactt ataacgcaac  20100
tcctaatact cattcaaact tccaggaaat tcttaatctg cttgtagcgg ataagctgga  20160
agaagctgcg caaaaaatta acgttcgtcg cgctgttgaa aaatatattt ccggtgatgt  20220
tcgaattgaa ggtggaagct tgttctatca aaatattgaa ttgcggtctg gtttggttga  20280
tcgtattctc gattcgatgg aaaaaggtga aaactttgaa ttttattttc cgttcttgga  20340
aaatctgttg gaaaacccaa gccaaaaagc ggtatctcga ctctttgatt tcttggtagc  20400
aaacgatatt gaaatcaccg aagatggtta cttctatgct tggaaagtag ttcgtgacaa  20460
ctactttgac tgtcactcaa acacctttga taacagtcct ggtaaagtag ttaaaatgcc  20520
```

-continued

```
acgtactcgt gtgaatgacg atgatacaca aacttgttct cgtggtctgc atgtgtgttc  20580
taaatcttat attcgtcact ttggcagttc aaccagccga gttgtaaaag ttaaagtaca  20640
tccgcgtgat gtagtatcaa ttccgattga ttacaacgat gctaaaatgc gtacctgcca  20700
atacgaagta gttgaagacg ttactgaaca atttaaataa gggcttcggc ccttttgttt  20760
taagagaaat tatgattccg acataaagga aagtttaaat gcagaaaacg aatccgggtt  20820
tacagagact atttcagatt ccgacattta ccctatcgaa cagcgattta accaatgaaa  20880
tgaaggtcaa aattgctgat actgcaagat actctttaaa acaaaatccg aatcaggata  20940
aggcagaagt tatcgaaaga tgccgtatcg ctgtgtacgc agagtttttt gtagcagatt  21000
ggctgagcgg gtatgttaac aaaggtcaag aagatgtcga tgatccgtac acgtatgcat  21060
gggatgtttt agcacatcca aaatactgcg ggctccgtgt agaagttaag acacatcaaa  21120
ctgactcgcg ttggatttcg gtaacaacgg gatgcagcgg agaatatcca tatggttctg  21180
gaataaatct agggcccatt ctaaatcacc aggtcgcgga ctgtataatt atattcaaca  21240
ctaaagaaat tcatccaggt gtcatccagt acactccgaa gttcatcggt gacagagaag  21300
accttcgtaa ggttgtaaga aaaagcaact acaatggatg gtatctttcc atttaaaaag  21360
ttttcacaaa acagtttaca taccacaagg accgtggtac tatacaacta tcaactgata  21420
cggatttgga gaatgaaatg aaaatcgctg agactgagct atgagttcat tatggtggtg  21480
ttttgtttgg ttaattagta ttccattgat ttgtttaaca tttacttttg tgatgaggtt  21540
attatgaaaa tttttaattc tgtacttatt gcttgtgcgt ggtgggttgc gcaagtttcg  21600
gcagtagtga ttggtattca catttattac gaatattttt aaaaaagttg tttacaagac  21660
tgttcctctg tggtattatt accctatcaa ctacggagga acagaaaatg aaaaagattg  21720
ttaaagctat atggaatgta gttataatac taatagtttt gagtatattc ccaatcgttt  21780
taatgattga tatattaaac gcttactttg gatttatgtg aggaaaatat gaagcgtaaa  21840
cgcagtgctt ttacatttat tgaatgattt ttcgataata tttttccggc tttattcatt  21900
ttcatgctga ttttcgcctt gggttcagtt gtagttggaa tctatttgat ggcagttgtc  21960
ggaatggaca ttcatcaaaa tggtttaaaa tccgtagttg aaacaatttg gaatggcgta  22020
aaatgatgaa tttgctgagt ggttggtttt atattcttat gttttacatt ggtgcaaatt  22080
tcccatattg gatgggatgg tcaacaactg cgtttggatt ttatactcct tgaggtgaat  22140
tatgaaaagt tttaaagatg taaaagttgg tgaaattttc tgtttagata atggtgatca  22200
gttaattcgt atttcacctc ttaagagcac tagcgagaaa ccgacagtta atgctacttt  22260
agcaaataac agtaatgaac gtttctgtat tgaaaatgat actgaaactt ataccgtaga  22320
agagttttgg gaattgagcg tcgactgcga cgattaattt aatggccgtg tgtattcatg  22380
cggccttgga gtagaaaata atttagagga aattaatatg aaatatatga ctgttaccga  22440
tctgaacaac gcaggcgcta ctgttattgg tacaattaag ggtggtgaat ggtttttagg  22500
aactccgcat aaagatattt tatctaaacc tggattttac tttttagtga gtaaattaga  22560
tggtcgtcca tttagtaatc catgcgtatc tgcacgattt tatgtaggta atcagcgttc  22620
taagcaagga ttcagcgcag ttctaagtca tattcgtcaa cgccggtctc aacttgcgcg  22680
tactattgca aataacaatg ttccatacac agtattttat ctgcctgctt ctaagatgaa  22740
acctctgacg acaggatttg gtaaaggtca gttagctttg gcgtttactc gtaatcatca  22800
ttctgagtat caaacacttg aagaaatgaa ccgtatgttg gctgataact ttaaattcgt  22860
```

```
tttgcaggca tattaatgag taatttccac aacgaacatg tgatgcagtt ttatcgtaac  22920
aatcttaaaa ctaaaggcgt cttcggacgc cagtgaggaa aatatgaata tcgcaaaatt  22980
attaggagtt atttcattta tttgttggat agtagcatgt gttttaacta tctgtatcga  23040
tgctagcagt gtgttttcac aagctttagc ccagggtatg tgtgcatatt taacatttgt  23100
gttgttatct aatgattaag aaaatcttgg gctattcact agcccttgct actttattgg  23160
tagcgttata ttacggaata atgttcggat taattcaagt tgtgcttttc atttctgatg  23220
ttattatggc actacattca ctagtatggt aaatttatgc aactgaataa tcgcgattta  23280
aaaagtatca ttgataatga agcattggct tatgctatgt acacggttga aaatcgtgct  23340
atcccaaata tgattgacgg atttaagcca gttcaacgat ttgttattgc tcgagctctt  23400
gatttggcac gaggaaataa agataagttt cacaaacttg cttctattgc aggcggtgta  23460
gcggaccttg gatatcatca tggtgaaaac tctgcacaag atgcgggggc tttgatggct  23520
aacacttgga ataataactt tcctctgtta gatggtcaag gaaactttgg ttctcgtacc  23580
gttcaaaaag cagcagcaag tcgttatatt tttgctcgtg taagtaaaaa tttctataac  23640
gtatataaag atactgaata tgctccggta catcaagata aagaacacat tccgcctgct  23700
ttctatttgc ctattattcc tactgttctt cttaatggcg tttccggtat tgcaactggt  23760
tatgcaactt acattcttcc tcatagtgtt tcttctgtta agaaagctgt attacaagct  23820
cttcaaggaa agaaagtaac taaacctaag gtagaattcc cagaatttcg cggtgaagtc  23880
gttgagattg acggtcaata tgaaattcgt ggaacatata agtttacttc acgaactcaa  23940
atgcatatca ctgagattcc gtataagtat gatcgtgaaa cttacgtgag taaaatttta  24000
gacccgcttg aagataaagg cttcattacg tgggatgatg cttgcggtga gcacggtttt  24060
ggcttcaaag ttaaattccg taaagaatac tctttgagtg ataacgaaga agaacgccac  24120
gcaaaaatta tgaaagactt cggcttgatt gagcgtcgtt cccagaatat taccgttatt  24180
aatgagaaag gaaagctaca agtttacgat aacgtagttg atttaatcaa agacttcgtt  24240
gaagttcgta aaacttatgt ccaaaaacga attgataaca aaatcaaaga aactgaatcg  24300
gcatttcgtt tagcctttgc caaggcacat ttcattaaga aagtaatttc aggtgaaatt  24360
gttgtacaag gtaaaactcg taaagaactg acagaagaac tttctaaaat tgatatgtat  24420
tcttcttatg ttgataaact agttggaatg aatatttttc atatgacttc cgacgaagca  24480
aagaaacttg ctgaagaagc taaagctaaa aaagaagaaa acgaatattg gaaaactact  24540
gatgtagtta cagaatacac caaagattta gaggaaatca aatgagtcca tttataggta  24600
tcacaagcgc tgcattagta tctggtagca ttttactggc gggtttaggt gttgttccag  24660
ccgtagcagg aggtcttctt gcgttcggaa ttcaacgtgt tatcatgaca gttatcacag  24720
tcatgcagta attttaggga gagctgaggc tctccctttt ttatttcaaa aatttttca   24780
caaaacggtt tacaaccaaa gcatactgtg gtactataca actatcaact actgatacag  24840
aattacggag attagaaaat gtctaaagta acttacatca tcaaagcttc taacgatgtt  24900
ctgaatgaaa aaactgctgc gattttaatt actgttgcta agaaagattt cattacagct  24960
gcagaagttc gtgaggtgca tccagattta ggtaacgcag tagttaatag taatattggg  25020
gtattgatta aaaaaggcct ggtggagaaa tctggtgatg gattaatcat tacaggcgaa  25080
gctcaggata ttatttcaaa tgcagcaact ttatacgcac aggaaaatgc tcctgaactg  25140
ttgaaaaaac gagcaactcg taaagcttct gatatggaag aagataaaga cttcatgtta  25200
aaacttttag atgaaaatgg atttgttctt aaaaaggttg aaacttaccg cagtaactat  25260
```

cttgctattt tagaaaaacg cactcacgga attcgtaatt ttgaaattaa taacaatgga 25320
aatatgcgaa tttttggata caaaatgatg gaacatcata ttcagaaatt tactgacatt 25380
ggtatgtcat gcaaaatcgc taaaaatggt aatgtgtatc ttgacattaa acgctcggca 25440
gaaaacattg aagcagtaat caccgtagca tctgaactgt gaggaataaa taatgaacaa 25500
gttagaaatt atcaatgaac ttcgtcgttg tgcagaaccc actcaagagg ggtgggacat 25560
ctggtatcat ggagcttatc ttggaactat cgtaaagatt aagactggta aatacatgat 25620
tattcgtgaa agtaaagatg ctccagtagg tattcgcaat aattttatgg cagcgataag 25680
ttcatttacg gatgcagctt acgaaattta ccttgttgat tataaagaat tccaggaatc 25740
tcaaccagtt attcgttcaa ttggtgttaa caaagctcaa cagaaaactt tgtggcagcg 25800
tattaaagga tggtttaaat gaaaactttt aaagaacgtt tagctctgtt agataaagct 25860
ttgtcgcgtg agactccgga aagtctggct gctaaattag cttctcacgg tggtgaatat 25920
acagaacaaa atgttttaga tgaagttcct gaaatttgtt ggcagactgc gtactgggat 25980
gaaaaccaaa agtatcaacg acgaattgtc tgtgcagcca accgttttaa attaaaagat 26040
ggacgaactc ttattattcc aggtgctcgt cattattcta aagatatggc agaagtttta 26100
gatgtagtta aatctcaatt agttactcag caagtttgtg atgatgacca agggtttatt 26160
gaccaatata gtaattattg gacacgtgaa gaagcaatga ttattgcaac ttacgctgga 26220
caagtacgta ttgaacgtgg tggtagtgaa aaagaacttt actctgagga cctttactaa 26280
tgaatattaa acagtttcaa attgatggaa ttatgaatca aatccaggcg ctggaatatg 26340
ctaataaaat gatgtcaacc aaatggggaa tttatgccaa tgaaccggca tttcagttct 26400
gtaatatgga attcactaaa aagctcgtag gaaaagatta tgtgtgccca tttagttctc 26460
cagtaaatgg aatgctaaaa cctgctttac gcgatcttta tattgcgatg aacgaagaaa 26520
tgataaaaga attaaaacgt caactgaagg tgattcaatt tggccaggga aattaattca 26580
aaatctgatt attttaattc tctcaatgat aaagataaaa atctaataag gcattttatt 26640
gttgagatgg gatatactga tacacgtgat ttaagagaac atatatttga atgtggtgta 26700
gctaaaaagt tttcattcac atgcaaatgt ttaagagagg taattcagca ctatgaacaa 26760
tttagtcgca aaacataatt ttaataaagc ttctgttcat aaagataaga agaaagcgtt 26820
taaagaatct aatcgcaaac agaaacataa ggggaaggtc tatgattatt gattctcaat 26880
ctgtggttca atatacaatc aaaattgata ttctagaaaa gctatataag tttctaccaa 26940
atttatacca ctcaatttgg aacttataaa gacctctcaa aagcaggata tttctatgta 27000
attccagctc caggaaaaag tattgatgat gtattaaaaa ctataatgat ttatgttctt 27060
gattatgaaa ttgaagatta tttcgaatga gtcataatct tgaaaaggta atcgagcata 27120
atgtagctca ggaacgtgag tcgttcaaag aattcgtaga aaaaattttt gaagaaaata 27180
acacagacca gtttacaaat caagtgtctg atgatattat aataaagtca actaattgag 27240
tggtatagtt aatgaataaa aacattgata cagttcgtga aattattact gttgcgtcta 27300
ttttgattaa attttccaga gaagatattg ttgagaatcg tgctaatttt attgcatttc 27360
tgaatgagat tggagtaacg catgaaggta gaaaattaaa tcagaattca ttccgtaaaa 27420
ttgtttctga attaactcaa gaagataaga aaaccctcat cgacgaattc aacgagggtt 27480
ttgagggtgt atatcgatat ctagagatgt atacgaacaa ataattattt agcccttcct 27540
aatattcttg ccgcctgagc acatattgat tcaaggcggt cattacttat atgatcattt 27600

```
ctataccagt acatggttat tgttccagca tagatattat ccaaattgaa atatggacaa  27660
ctgtacatgt aatttatttc gggagtaggc tttttggttg gtaaaaaagc aaattttgag  27720
ttggaataat aatgacgtcc atttaaatga actgcatatt catccatagt tttatcaaca  27780
ggatatcctc caagtgattt ttcacttatt gttgaaggta attttccttc atatgctata  27840
atatcaacaa aatagtttaa gtttttaggg cggaaagaat acaccgcact aaagtctgcc  27900
tcagatgata tatgaactat ctggagttgt tccagggcga cagattcaaa gcgtgcattt  27960
ctttcctttt caataatttc actgtatgtt tcatactttg attgcttata gtactcaaat  28020
aaactatctc ccctatacca aacaatcgcc attataaaca aaagaattac gacagctacc  28080
cgggaagcaa gaactttccc ggtagcgtta tctttgaaca agcgatctag aacaccaaac  28140
agaatatcag agggcgaaaa tgatattcta ggtgctgcca tagaccctcc ttttaaggat  28200
atttattcaa aattatactc ttgaaccata tattgtacca actttagtcc aagttggagc  28260
attaccagta acagctttac ctgctgcgcc gccgttatat tctgatcctc gaccgcgaat  28320
attacattta cctcctgcat caccaccatt cccaccattc ccaccattat agataccgtt  28380
gacagaccct ttaccgggtg cagaaatagt accagcggta gcaccttgtt tcatattagc  28440
agaaccacca gcagcgccaa atggacgacc gcctcctccg ccgaaagtca atttcattcg  28500
tgaaaaagga gagtagtatc cgccgccacc gccgccaccg cctcctgcga taacaccatt  28560
gttgttaata cgtaatctag ttccaattcc gttatttatt gcagttcccc ctgctccacc  28620
ggcagagtta                                                         28630
```

```
<210> SEQ ID NO 25
<211> LENGTH: 10309
<212> TYPE: DNA
<213> ORGANISM: Artificial Sequence
<220> FEATURE:
<223> OTHER INFORMATION: partial sequences of Bacteriophage EK88P-1

<400> SEQUENCE: 25

acgtatgcat tagttaatga gctaggaaaa tctaagcatg gaacaccagt agattgagaa     60
acaatatttc ctgtaatagt aataacaaca ggagtacttc cttgggcttt tatccaattt    120
attagtgtgt ctttattata agaattgcta gcaccaatgc tgtaatatac ttctttagat    180
tgtccggcca ttgagctcat ccaaccagga actgaaacac gaactgctct catcgcagca    240
tccatccaac gttgtccagt ttcattcacg gcagattcgc caatccagcc aggaacacct    300
acaattgcca ttaaaaatcc ttagagggcc gaagccctct tttacataag tttagattca    360
agttctttta cacgagaaga aagtgttttc acagcttcaa ccagaagagc aatctgggct    420
tgagaagaaa cagtgagtat tttattaccc ttaatatctt caacttcgcg aactgcttct    480
ggtaaaacat cttgcagtgt ttgagccaca atacccgctt cagtctgaac aatttcaccg    540
cctatatagt cagctttatc atagattaaa ccatcaagct gttcaacctt ttcaagagca    600
ttttcaatag gtctgaaatt agatttcaaa cgaatatcag aacgaatata aacgtttggg    660
gcatttatat tcatgtcaga ataagtgtca cccgtctgga atctcattcg gcggtcggag    720
ttagtaatga tatcaagaat tccgtcaccg gattgtttaa ttccagtatc attatcacca    780
aatgctatac tatttccacc aagtgcgtta ttgatattaa taccaaatga attcattcgg    840
ttaacaccat ctacagtagc attatttact acaaagcggt tagctccacc tggagttttt    900
tcaaagtaag caatatagtt agtttcatct gcaatttcaa tgcggttacc gcgagaagca    960
tcgccagcat gaaatattct catatttctc gggttagcac cagacttatc aaagttaatg   1020
```

-continued cttccattat ttttgatgtt aaggccattc caaaactctg ataccccaga aacgctcata 1080
gagtttgaaa tagttacttt accggaagca atattaatag aaaaaggtct caagctatta 1140
taagaacccg aggctttagt tttatcagta tcggtatttt tatctgttaa taatatgtgg 1200
aacgtagtac catcattata aaacagagca gctgcagagc cactttcgtc gccgttagat 1260
ttgtgacggt atcctatagt agtatttgcc acaaaagttg catttgtaga aatgttagaa 1320
ctacccgcgt caaaaacgcc tgagctatta ttaagaagtt taaaaacacg acctttaaca 1380
atatctacag gaagctcttc taccggcgat tgtgtaggtc catataatcc atgaactatc 1440
acagaagcat tttctgaagt gctatattct atagtaagtc tatttaaata agtgccacaa 1500
ctaatataaa catcatactc atcgcctgag gtattaatat acgcaatatc tttaatagca 1560
tctgtttcac gttgccataa aacaccgtta attcctttag gtgtattatt accagaacgt 1620
aatacaattt cattaattgt tgcttgtttg aaaataccaa cgttaaaacc ggaaccgcct 1680
gttattttaa attggaccgt agctacacct tgaggcatag ttactgttgc caatttatac 1740
caaccactta cagaagaata gttaatccag cccgtggtaa ctttgcggtc taaagtagta 1800
ttcaagttag caaagttacc agaaccaccg gtaatattac catcagtacc aagataaact 1860
ctgccgccag cggaaatacg tttaggagat acaaaatcac ccgatttagt aaattcccat 1920
ccgtaatcag caatctgagc accagtagaa ctaccgtctc cgccagcgtg ataatggaca 1980
cggaaattac cgttattcaa taaagtacca attgaataac agctattacc ctgaacatac 2040
cgctgtttaa tcattggaac ataagtgctg gtatcatcac ggtcaatatt catgtagaat 2100
ggtgctcgaa cgttttcgtt attctgggaa gcaaatgaac ctgcaccagc tgaacgacca 2160
tttgcatcca tcaaagcatt tatataagca ccgttttcta agtccatacg gaaattaggg 2220
ttaattttag aatgactgtt aaccgtaacc aggaatgcgt tggtatcaat atttaacagg 2280
ccattgccgc gagccgagtt gcctatcatt aaagaatggc ctatattaat tgaaccggta 2340
cctaattcaa tactaaacgg acgaaggttg cttattgcgc cattttcccc ttcatattgg 2400
ttggttggga taatatgcaa tgatgtttct gaacgacgga aaatggcacc ataccggtcg 2460
ttccaaattc tcaatgcatc gttaacaccg ccaattttaa cctgtcctgt tatattagag 2520
ccgcctctaa ttgttgcgcc gttttcaaaa gtaactccac ctttaaaagt acctttacct 2580
gatgtagtta tatcaccgag cccgacgata tgcccagttt ctacagttcc gttaaattta 2640
aagttaatcg gacctactgt ttgacctgat gcaggattag tacgttgagc gtagaaataa 2700
taaccttgtg aatctgaaac ttcgaataca gtttctctat tacctggagt tgagttaaat 2760
gagttacccc atgctttaat ggttacagta tttttattct gaccattacg agtgcctgca 2820
ccccagttaa tggtttttgt cccgtcaaca cctgtaggcg ctttaaataa caaagcattg 2880
gtattatcat cacctgataa aaataatcca gtacgcattg aaatacgttg ggttgagtca 2940
aatgtaccat ctgctctaat agcaactcta ttagacccag ttttaatgtc taaaatacct 3000
ggctcaacaa taagtccttc ggccatacca acagccatac gacctgtacc acggaaatag 3060
tgatacatct tggcattgct gctataacct atatgagtct gaccatcgcc gttattatta 3120
ccatcaatat cggtgcgtgc ggtaaacatt gcttggttgt tatttgggaa atcccaagta 3180
gaaccggaat ctcgactata accaaccatc aattttttag tactgttaat accgttattc 3240
aaaatagtcg cagaagaaat accgttagcc atcaggtcat aaacgccatc acggacccat 3300
ttaataccgg tgtcattatc accaattgca ataccgatag aaatggcaga atctaaagga 3360

-continued

```
taacgtccat ttgccccgtt atcaggaaga cctactgaaa tagatttacc tgcggtaata   3420
cgcccagtgg tatcaaacgc ccattggaaa gacgaaggcc ctacgccagt ccaccaagaa   3480
atttcttgcg gctttcctga acgacaatca actatttcat ggaaaatact agaagtattt   3540
gaagcccgca ttttacgcat gtagttcaat ccgtttgtat cacggtcaga accatctgct   3600
ggtggattat aaatccaagt aggtaaagaa acaatgtcat aacccgtgtc attattcggt   3660
ataaaggttt tagaactcag gttaatattt tttgtattga cgcgcggtgc agaaacaaat   3720
ccagttgccg agttaatatt acctgaagcc gaaatattac ctgcacggac ttcaatactg   3780
ccattattta caataaaact accgtttcga ttaaaagtcc aatattttga atcaccagat   3840
tcattgatat attgaatttt aaaacttcct tcgtttacta acgtaccaac agaaaaagtt   3900
ccatctttat agcgttgttt aattagcgga tggtattctg aagtagaagt agttgaactc   3960
aaatcggtaa agataggagc tttagtttta tgttggtttg cccaagcacc attaccagca   4020
gttttaggta aaaattcaat atattttcct gcataaacaa actggtttcc attaagatta   4080
tatgttccat tttgtaaata atcaccagtt tgagtgatat ttccactgat actaccgcca   4140
gcagaaatgc ttaagtcaat gatatttcct gaatcatctt tagtaaaaat tgttctatct   4200
tttaagttta tagccaattc accttcggct aatattgaag cagcaggacg tgcacctgcg   4260
gttttgcttc ttttaaattg tatttgtttt aaagtagcca taagtcctct taataatagc   4320
cgaaatcttg aacagaatcc ttaattacga tttggtcaaa tcgtggaaca tgtgaaggtt   4380
gagacgcagg attctgcgag aaaaagtttg gcgctgttaa attacctgtc atagtgtcac   4440
cagaacgcaa cactctagag ttcgcatttg ctgtaacagt atttattgct ccatcaacat   4500
agtcctttct agtaaggtca ttcgctgcta taggagcagc cgcattactt cttatttgac   4560
ctactgctgt cacaacgcct tttgtactaa tatcaccatt acgtgcatta attacaacag   4620
ttcggtctgc tgaaccttgc gatgatttaa aaccaatacc attccacgaa acgatgtcaa   4680
tacttgccat agcaaaagta gctgcatcac cgttacctgg ataaacaccg cactgttgac   4740
tactacctat agtaggaaca tgtactcctc cattaaatcg aacagtcgcg gcgtaagtac   4800
caccattagc tttagaaacg aaatcgttat cagcagcttg tggtttatta tattctgaat   4860
atattttaaa tgatttatag agtacatcgt caccggctgg attcaatgga aaatttcctt   4920
gatgccaaat gacagagcct ccggttgttg aacctacttt taaatcagcc attctatgcc   4980
cctttatttt aatagtattt ataaagaaaa agggaacccg aaggctccct caatttatac   5040
ttctctaaat tcttgcccaa atactttacc agctttagac gatgcttgcg taggaagtgc   5100
cattatatcc ggaggtgaag cagattcaca gatataatta acacgaatgc cgttgatacc   5160
aaattcagca ggtttcgaaa tacttccatt tcttgacact tccgaaaagc ttaaattcct   5220
catgccacct tgaccagctt gtgcagttct ttgcgcgtat atcgtaaatc ccacagcatt   5280
ttctggaaca actacataat cttcctttaa ttcccaagac ccagcttgtc cggtgaactc   5340
agcttgtgtc gaggaaatat atccatttga tgcgttataa aaacggatgg atatatttgt   5400
agttccaaga gcaagtaaat cggcatcagc atataactga gctttaagat aaagaacatc   5460
gccaggaatt aaattataat cagagagttt acttatggca gctgaagttg gtagacgtgc   5520
aatttcgtta ttagttccac caactgctga cataaattgc tcaacgcttt catacgttct   5580
tcttggaaac ccggtagctc cgacgtcttc taaactgtca aatacaacat ctaaaatagt   5640
ttgatagtca tctgtgcttt ttctattact tagtttaaca tgctctaatg caatagctct   5700
tttagaagaa gtgtaaaaag cagcatatga tacgtcaaat cttgacaata tagaatcaga   5760
```

-continued

```
tggaaaagca gacgttcctg cggttcttag ccaagatact acttcaggag gaaaattaac   5820
ttttccacta gttaatatag caacaagtct attattcgtc aaagaattca tgaaactaac   5880
aaaagcagct gatgtagtat catttgaagt agaaaaagca tatgacttac tatcaactaa   5940
tgctccggtg gaagggtcaa aaactcttag atgaagacct gcgctaaatg tttgatttcc   6000
gacaggatta tcttgaaatt taacatatgg tcctgctgta gaaagcgggc aagaacccgc   6060
tatacttatt ttgtatctta ctgaattact ttccgataaa aatggcgttt ggacatatcc   6120
ttgtccaaac tctgccataa atttttccat aatacctctt attcaatcca ttcaaattta   6180
acagatttat tcactgggtc aggaataatg cgaacattac caattcgtaa gaaatcacga   6240
atagtaagat tccccattgt agcattatca gatggtaaag caccgatatc agacggctga   6300
ggagggttac ctccatcaaa tacctgaaca aaacttgacc aagagttttt ggttttctgc   6360
catgtacgtg tccagcgagt ggtacgtgct tctggggtcg ttggataagt aatccaatct   6420
tggtaaagcg aatcaagtgt gttaccaaac tgagtcaatg taccaggaga tttaacctct   6480
tctccgcgtt ctaagtatgg aagtccagtc acttcattag tttttcaac catttaaaa   6540
taacctggga actggttata agtagctgaa tcattaatgt caattgacca gaatcctaca   6600
gtatcagatg ttggcgcacg ggtgtatagg tcagcagttt tagtgccctg agaacgaatt   6660
ctcgagttaa cagttaaacc acctgaattt atagtagcac ctttagcaat gattaagctt   6720
tcgccaatcg ttacttgacc ggatgcatta ttaatagcta aaggacgtaa tccattaaat   6780
ccgccagtct gatcacccga tgcagtgagc ataaaatatg tgcttccgcc atcattcctg   6840
ataaagaatc catgattacc atttattgct ctgaaagcat tcgatgattt actgataagt   6900
tcgccattag cagtaactga actaccaaat gttgcaacgc cgttcgcgtt caaagaaccc   6960
gaagcattga catttatcgg catcacagta ccattgatac taaacgttat attcccagct   7020
ttattacgct gagaataaaa gtgattagac gtttcatcac caacttcaaa tacagtagaa   7080
cgtgttgtat ctgaaccgcc gccaaactga tttccccaaa ctctgatagt catcgtctgt   7140
actgggttag ttccggtttg aggtcctttc tcaaaaatca gacgagttgc cgttccagta   7200
ttagaaatag ttaatgtact atttgccgaa actgatccac caaacgtagc agtactagat   7260
gatacaagag gggcactcag attcgtttgt tgggttaagg ttagtgaacc attaaccgtc   7320
tgcgcaatat ccctacgaat gaactgagat gaatctagac catctaataa attcgcgtca   7380
gcggcttttg cttttaatgg caaataattt gctaatacac ggtttaattc atatggtgat   7440
actgcatagc tatttttctc atataactct aagtcctgcg ttgaaccagc tgtatcatta   7500
ccaacgaatg taattgaacc agatgaagtt ttaacaaagc ctcttatcgc agtagtagct   7560
gcccaagtag gttcactctg tacaatccat tttaaatttt ttggagatac agcagtattt   7620
gctgacgttc cagttacagt ttcagactga gttgcaactt taataacacc ttcctgcgat   7680
tcggtagatt tagtacctaa aagcttttta ggagttatta aaacattatc taatgttcct   7740
gcagcagctt caacttgtgt agccacacga agtgtaccac gctgtgtctc atttgcttca   7800
agaatattaa gggtataatg gtcccagaga gttcctgatt caactaatcc agatagagca   7860
acaacagaag tacgatcagt actattaaat ctagttttaa tttttaatgg tgtagagata   7920
cgagtatcgt cgacgcctgc gtcgaattca acttgtgtag caatttcagc tataccactt   7980
aaactttcag ttgctttacg gtcatttaaa gttttaggag tgactgcgcg agtataatca   8040
gttcctgtat taacttcact ttgcgtagca atttcaatta aaccaattct tccatcagtt   8100
```

```
gatgtctttt tatgtaacgt ttctggcgtt acaaccgcat ttgcccatcc ttcttgactc   8160
tgtccagcaa ttacttcact ttcaactgct aaaattactg caccttgttg tgttggagta   8220
gctttatact gatccagagc tttaggcgaa acaactaaat tattaatgtt tttattataa   8280
acgtttgtac catttaattc acggctagaa gctggagtag cacctgcagt agatacaaaa   8340
gttacaatac cagataatga ttcagaacct tgacgagctt gaagcttttt aggagtaatg   8400
attgtagtat catcagtacc tgtattagtt tcttgctgcg tagcaatttc agcaacacct   8460
ctacgagttt ctgtagcagt tctttcattc agctttttag gagtaatgat aagatcatca   8520
gcaaaagaga atgtggtgtt ctgattcact tgagtagtag ttgctattct tgcaatacct   8580
ctacgagttt cagtagcagt acgattagct aacgtttctg gagtaattgc taattctttt   8640
tgcggagaat tttctaaatc gacattagct tgcgcttgtg tagctaaagc aatcacgcct   8700
aatcttgctc tagtagaatc atttaaagaa tcaactcttt ctacggttgg aacgttttgt   8760
tgtacaaccc agtattttcc atcagaatct tctatataag caagttgtaa aactggaaca   8820
taattagttt caccgttaaa aactaattct tgaacagtca cccattcagc ttcaggtgga   8880
tactctgaac gttttgggaa ttgcagcaat tgaactgaag aagcaatttt atcttcaccg   8940
gcagctttga ttttaactgt ttgtcctttt ctcatgtaat tcatggaaat tttaacagta   9000
tcaccaacag aaatattagt tggaagctga agctcaattg tttgagttgt tccattattc   9060
gcaccaaata ccataacttc ttcatttgga cgaatgtttg aattagttgt tatgatacgt   9120
aaacgtgctt tactgtcccc gtcaaataat ctccataatt tctcattatc atcatacatc   9180
aagaaaccgt caatcgatgt acggccttca atggaatgag ttccatcttc ttgcactgat   9240
gtcgtttcat catatgtagt aacaattgta tgataaagag ggtttaattt atccaaatcg   9300
acgaaattaa taatatcgcc gtgattagca aatctcggaa gtttaatatt tatcggtgca   9360
gcagaagtaa atctacgtac gataaaatcg ttggattgtg cttgataagt attcgctggt   9420
gttacaacta cagcttctct actataatca gctacataca tttgccacag acgattacta   9480
aaaattaaaa ctaactgtga ctttggatga gtcattagta ctgaacgtac ctgttcacct   9540
ctaaagttta caatactttg cactggagct acaattaaaa cttggttaac tccaggtttt   9600
cctccaatat cttggagaac gatagtatca ccatcaattg gagaagacgg taaagtaaac   9660
gtaatgtcat ttccagctgc agtgttaacc gaaatagctt caccggattt taattgatat   9720
gaaccagatg agactgtaat ccagttagca tcggtacgta atgctctcca gcgtccgcta   9780
ttaaaagttc ctgccggttt tggaatatca tttatagcag cccaaaagcg gttatcataa   9840
atgattacaa aatcttttaa atatccacga gttggatcgt attgttgaac tgtgttttct   9900
tgaattaggt aatcaacgtt aacaccgtca gttcctacgg cacgatcagc taaagctacg   9960
ttgattattt tatcgccacc tgcgtccaga ccatcttctg ctctgaactt tcttttaatc  10020
tcggccattc tcccgggctc ctattgtgtt ttcaataata agtatttata cttgtttact  10080
ttaagattcg gatggtatat aatagaaatc tcactaattg aacgaggttc atatggattt  10140
agaaatgatg ttggatgaag attacaaaga aggaatctgc ttaattgact ttagtcaaat  10200
tgcgctttca actgctctgg taaacttccc agataaagaa aaaattaatt tatcaatggt  10260
tcgtcatttg atattgaact caattaagtt taatgtcaaa aaagcaaaa              10309
```

<210> SEQ ID NO 26
<211> LENGTH: 20
<212> TYPE: DNA
<213> ORGANISM: Artificial Sequence
<220> FEATURE:
<223> OTHER INFORMATION: PCR primer sequences

<400> SEQUENCE: 26
tatcacccat gttccacgct 20

<210> SEQ ID NO 27
<211> LENGTH: 20
<212> TYPE: DNA
<213> ORGANISM: Artificial Sequence
<220> FEATURE:
<223> OTHER INFORMATION: PCR primer sequences

<400> SEQUENCE: 27
tggtattact cgtccgcagt 20

<210> SEQ ID NO 28
<211> LENGTH: 20
<212> TYPE: DNA
<213> ORGANISM: Artificial Sequence
<220> FEATURE:
<223> OTHER INFORMATION: PCR primer sequences

<400> SEQUENCE: 28
ccaagtgcca gtcctaaacg 20

<210> SEQ ID NO 29
<211> LENGTH: 20
<212> TYPE: DNA
<213> ORGANISM: Artificial Sequence
<220> FEATURE:
<223> OTHER INFORMATION: PCR primer sequences

<400> SEQUENCE: 29
atgggtcggg ttactggttc 20

<210> SEQ ID NO 30
<211> LENGTH: 22
<212> TYPE: DNA
<213> ORGANISM: Artificial Sequence
<220> FEATURE:
<223> OTHER INFORMATION: PCR primer sequences

<400> SEQUENCE: 30
acccaatctc ctattctgtc ca 22

<210> SEQ ID NO 31
<211> LENGTH: 22
<212> TYPE: DNA
<213> ORGANISM: Artificial Sequence
<220> FEATURE:
<223> OTHER INFORMATION: PCR primer sequences

<400> SEQUENCE: 31
tgactgatat tgattctggc ga 22

<210> SEQ ID NO 32
<211> LENGTH: 20
<212> TYPE: DNA
<213> ORGANISM: Artificial Sequence
<220> FEATURE:
<223> OTHER INFORMATION: PCR primer sequences

<400> SEQUENCE: 32
ggtttcaact cgagcaaggg 20

-continued

```
<210> SEQ ID NO 33
<211> LENGTH: 20
<212> TYPE: DNA
<213> ORGANISM: Artificial Sequence
<220> FEATURE:
<223> OTHER INFORMATION: PCR primer sequences

<400> SEQUENCE: 33

tcggttgtat cttgggctga                                            20


<210> SEQ ID NO 34
<211> LENGTH: 21
<212> TYPE: DNA
<213> ORGANISM: Artificial Sequence
<220> FEATURE:
<223> OTHER INFORMATION: PCR primer sequences

<400> SEQUENCE: 34

cggaatttgt acatcaccgc t                                          21


<210> SEQ ID NO 35
<211> LENGTH: 20
<212> TYPE: DNA
<213> ORGANISM: Artificial Sequence
<220> FEATURE:
<223> OTHER INFORMATION: PCR primer sequences

<400> SEQUENCE: 35

cttgatacgc aggaccaagc                                            20
```